United States Patent [19]
Bryan et al.

[11] Patent Number: 5,863,724
[45] Date of Patent: Jan. 26, 1999

[54] METHODS OF SCREENING FOR PERSISTENT HYPERINSULINEMIC HYPOGLYCEMIA OF INFANCY

[75] Inventors: Joseph Bryan, Houston, Tex.; Pamela Thomas, Ann Arbor, Mich.; Gilbert J. Cote, Houston, Tex.; Robert F. Gagel, Houston, Tex.; Lydia Aguilar-Bryan, Houston, Tex.; Daniel A. Nelson, Charlotte, N.C.

[73] Assignees: Baylor College of Medicine, Houston; The Board of Regents of the University of Texas, Austin, both of Tex.

[21] Appl. No.: 404,531

[22] Filed: Mar. 15, 1995

Related U.S. Application Data

[63] Continuation-in-part of Ser. No. 226,972, Apr. 13, 1994, abandoned.

[51] Int. Cl.$^6$ .............................. C12Q 1/68; C12P 19/34; C07H 21/04
[52] U.S. Cl. .......................... 435/6; 435/91.2; 435/810; 536/24.3; 536/24.33; 935/77; 935/78
[58] Field of Search ................. 435/6, 91.2, 174, 435/183, 810; 536/24.3, 24.33, 26.6, 23.1, 23.5, 25, 32; 935/77, 78

[56] References Cited

U.S. PATENT DOCUMENTS

| | | | |
|---|---|---|---|
| 4,237,224 | 12/1980 | Cohen et al. | 435/68 |
| 4,683,195 | 7/1987 | Mullis et al. | 435/6 |
| 4,683,202 | 7/1987 | Mullis | 435/91 |
| 4,800,159 | 1/1989 | Mullis et al. | 435/172.3 |
| 4,883,750 | 11/1989 | Whiteley et al. | 435/6 |
| 4,965,188 | 10/1990 | Mullis et al. | 435/6 |

FOREIGN PATENT DOCUMENTS

| | | |
|---|---|---|
| 0 329 822 A2 | 8/1988 | European Pat. Off. . |
| 2 202 328 | 3/1988 | Germany . |
| WO 87/06270 | 4/1987 | WIPO . |
| WO 88/10315 | 6/1988 | WIPO . |
| WO 89/06700 | 1/1989 | WIPO . |
| WO 89/09284 | 3/1989 | WIPO . |

OTHER PUBLICATIONS

Gregory et al. Expression and characterization of the cystic fibrosis transmembrane conductance regulator *Nature* 1990 347:382–386.

Ho et al. Cloning and Expression of an inwardly rectifying ATP–regulated Potassium Channel *Nature* 1993 362:31–38.

Hopkins et al. Two Sites for Adenine–Nucleotide Regulation of ATP–Sensitive Potassium Channels in Mouse Pancreatic β–Cells and HIT Cells *J. Membrane Biol.* 1992 129:287–295.

Hyde et al. Structural Model of ATP–Binding Proteins Associated with Cystic Fibrosis, multidrug resistance and bacterial transport *Nature* 1990 346:362–365.

(List continued on next page.)

*Primary Examiner*—W. Gary Jones
*Assistant Examiner*—Debra Shoemaker
*Attorney, Agent, or Firm*—Woodcock Washburn Kurtz Mackiewicz & Norris, LLP

[57] ABSTRACT

The present invention is directed to a method of detecting persistent hyperinsulinemic hypoglycemia of infancy comprising obtaining a sample comprising patient nucleic acids from a patient tissue sample; amplifying sulfonylurea receptor specific nucleic acids from said patient nucleic acids to produce a test fragment; obtaining a sample comprising control nucleic acids from a control tissue sample; amplifying control nucleic acids encoding wild type sulfonylurea receptor to produce a control fragment; comparing the test fragment with the control fragment to detect the presence of a sequence difference in the test fragment, wherein a difference in said test fragment indicates persistent hyperinsulinemic hypoglycemia of infancy. A diagnostic kit and primers for the detection of persistent hyperinsulinemic hypoglycemia of infancy are also within the scope of the present invention.

18 Claims, 12 Drawing Sheets

OTHER PUBLICATIONS

Kelly et al. Cloning and Expression of A Novel Inward Rectifier K+ Channel HRK1 From Human Hippocampus *Biophysical J*. 1994 66(2) :A109.

Khan et al. Dissociation of $K_{ATP}$ channel and sulphonylurea receptor in the rat clonal insulin–secreting cell line, CR1–D11 *Proc. R. Soc. Lond. B* 1993 253:225–231.

Kozak M. Point Mutations Define a Sequence Flanking the AUG Initator Codon That Modulates Traslation by Eukaryotic Ribosomes *Cell* 1986 44:283–292 Aug. 11, 1997.

Kramer et al. Direct Photoaffinity labeling of the putative sulfonylurea receptor in rat β–Cell tumor membranes by [H3] glibenclamide *FEBS Lett*. 1988 229:355–359.

Kyte et al. A simple method for displaying the hydropathic Character of a Protein *J. Mol. Biol*. 1982 157:105–132.

Nelson et al. Evidence that a 140 kDa Protein Contains the β–Cell High Affinity Sulfonylurea Binding Site and is an Integral Part of the ATP–Sensive Potassium Channel *Amer. Diab. Assoc. Diabetes* 1992 41:78A.

Nelson et al. Photolabeling of β–Cell Membrane Proteins with an $^{125}$I–Labeled Glyburide Analog: The High Affinity Sulfonylurea Binding Site Residesona 140KDa Polypeptide Houston Tx.

Nelson et al. Purification and Characterization of the High Affinity Sulfonylurea Receptors *Biophys. J*. 1993 64:311.

Nelson et al. Purification of the 140 kDa High Affinity Sulfonylurea Recptor *Diabetes* 1993 42:129.

Nelson et al. Specificity of Photolabeling of β–Cell Membrane Proteins with an $^{125}$I–Labeled Glyburide Analog *JBC* 1992 267:14928–14933.

Nichols et al. Adenosine triphosphate–sensitive potassium channels in the cardiovascular system *Am. J. Physiol*. 1991 261:H1675–H1686.

Panten et al. Pancreatic and Extrapancreatic Sulfonylurea Receptors *Horm. Metab. Res*. 1992 24:549–554.

Panten et al. Control of Insulin Secretion by Sulfonylureas, Meglitinide and Diazoxide in Relation to Their Binding to the Sulfonylurea Receptor in Pancreatic Islets *Biochem. Pharm*. 1989 38:1217–1229.

Posnett et al. A Novel Method for Producing Anti–peptide Antibodies *J. Biol. Chem*. 263:1719–1725.

Rajan et al. Sulfonylurea Receptors and ATP–Sensitive $K^+$Channels in a Glucagon Secreting Pancreatic Alpha Cell Line *Diabetes* 1992 41:47A.

Rajan et al. ATP–Sensitive K+ Channels in Pancreatic Alpha Cells *Biophys J*. 64:A311.

Rajan et al. Ion Channels and Insulin Secretion *Diabetes Care* 1990 13:340–363.

Rajan et al. Sulfonylurea Receptors and ATP–sensivitive $K^+$Channels in Clonal Pancreatic α Cells *J. Biol. Chem*. 1993 268:15221–15228.

Riordan et al. Identification of the Cystic Fibrosis Gene: Cloning and Characterization of Complementary DNA *Science* 1989 245:1066–1073.

Sanger et al. DNA sequencing with chain–terminating inhibitors *Proc. Nat'l. Acad. Sci USA* 1977 74:5463–5467 Aug. 1, 1997.

Schmid–Antomarchi et al. The Receptor for Antidiabetic Sulfonylureas Controls the Activity of ATP–modulated $K^+$Channel in Insulin–secreting Cells *J. Biol. Chem*. 1987 262:15840–15844.

Schwanstecher et al. The Binding Properties of the Solubilized Sulfonylurea Receptor from a Pancreatic B–Cell Line are Modulated by the $Mg^{++}$—Complex of $ATP^1$ *J. Phar. Exper. Ther*. 1992 262:495–502.

Schwanstecher et al. *Br. J. Pharm*. 1992 107:87–94.

Takano et al. The ATP–Sensitive $K^+$Channel *Progress in Neurobiology* 1993 41:21–30.

Vu et al. Functional Solubilization of the HIT Cell SUlfonylurea Receptor *Diabetes* 1989 38:178a.

Vu et al. Partial Purification of the HIT Cell SUlfonylurea Receptor *J. Cell BIol*. 1989 109:102.

Walker et al. *EMBO Jour*. 1982 1:945–951.

Aynsley–Green et al. Nesidioblastosis of the pancreas: definition of the syndrome and the managment of the severe neonatal hyperinsulinaemic hyppoglycaemia *Arch. Dis. Child*. 1981 56:496.

Kaiser et al. Regulation of insulin release in persistent hyperinsulinaemic hypoglycaemia of infancy studied in long–term culture of pancreatic tissue *Diabetologia* 1990 33:482.

Bruining, Recent advances in hyperinsulinism and the pathogenesis of diabetes mellitus *Curr. Opin. Pediatr*. 1990 2:758.

Matthew et al. Persistent Neonatal Hyperinsuinism *Clin. Pediatr*. 1988 27:148.

Glaser et al. Familial hyperinsulinism maps to chromosome 11p14–15.1, 30 cM centromeric to the insulin gene *Nature Genet*. 1994 7:185.

Thomas et al. Homozygosity Mapping, to Chromosome 11p, of the Gene for Familial Persistent Hyperinsulinemic Hypoglycemia of Infancy *Am. J. Hum. Genet*. 1995 56:416–421.

Kohler et al. Continuous Cultures of fused cells secreting antibody of predefined specificity *Nature* 1975 256:495–497.

Cline M. J. Perspectives for Gene Therapy: Inserting New Genetic Information Into Mammalian Cells by Physical Techniques and Viral Vectors *Pharmac. Ther*. 1985 29:69–92.

Walker G. T. et al. Isothermal in vitro amplification of DNA by a restriction enzyme/DNA polymerase system *Proc. Natl. Acad. Sci. (U.S.A.)* 1992 89:392–396.

Kwoh et al. Transcription–based amplification system and detection of amplified human immunodeficiency virus type 1 with a bead–based sandwich hybridization format *Proc. Natl. Acad. Sci. (U.S.A.)* 1989 86:1173.

Ohara et al. One–sided polymerase chain reaction: The amplification of cDNA *Proc. Natl. Acad. Sci. (U.S.A.)* 1989 86:5673–5677.

Wu et al. The Ligation Amplification Reaction (LAR) – Amplification of Specific DNA Sequences Using Sequential Rounds of Template–Dependent Ligation *Genomics* 1989 4:560.

Maxam et al. A new method for sequencing DNA *Proc. Natl. Acad. Sci. USA* 1977 74:560–564.

Aguilar–Bryan et al. Photoaffinity Labeling and Partial Purification of the β Cell Sulfonylurea Receptor Using a Novel, Biologically Active Glyburide Analog *J. Biol. Chem*. 1990 265:8218–8224.

Thomas et al. Mutations in the Sulfonylurea Receptor Gene in Familia Persistent Hyperinsulinemic Hypoglycemia of Infancy *Science* 1995 268;426–429.

Lichter et al. High–Resolution Mapping of Human Chromosome 11 by in Situ Hybridization with Cosmid Clones *Science* 1990 247:64.

Ijdo et al. Multiple Variants in Subtelomeric Regions of Normal Karyotypes *Genomics* 1992 14:1019.

Welsh et al. Molecular Mechanisms of CFTR chloride Channel Dysfunction in Cystic Fibrosis *Cell* 1993 73:1251–1254 Aug. 1, 1992.

Khorana et al. Direct sequencing of PCR products in agarose gel slices *Nucleic Acids Res.* 1994 22:3425–3426 Aug. 1, 1997.

Lou et al. The Calcitonin Exon and its Flanking Intronic Sequences Are Sufficient for the Regulation of Human Calcitonin/Calcitonin Gene–Related Peptide Alternative RNA Splicing *Mol. Endo.* 1994 8:1618–1625 Aug. 1, 1997.

Takahashi et al. A null mutation in the human CNTF gene is not causally related to neurological diseases *Nature Genet.* 1994 7:79–84 Aug. 1, 1997.

Satokata et al. Characterizationof a splicing mutation in group A xeroderma pigmentosum *Proc. Natl. Acad. Sci.* 1990 87:9908–9912 Aug. 1, 1997.

Higashi et al. Aberrant splicing and missense mutations cause steroid 21–hydroxylase [P–450(C21)] deficiency in humans: Possible gene conversion products *Proc. Natl. Acad. Sci., USA* 85, 7486 1988 Aug. 1, 1997.

Philipson et al. Pas de Deux or More: The Sulfonylurea Receptor and K+ Channels *Science* 1995 268:372–373.

Aguilar–Bryan et al. Cloning of the βCell High–Affinity Sulfonylurea Receptor: A Regulator of Insulin Secretion *Science* 1995 268:423–425.

Scangos et al. Gene Transfer into Mice *Advance In Genetics: Molecular Genetics of Development* 1987 24:285–323.

Virsoly–Vergine et al. Endosulfine, an endogenous kpeptidic ligand for the sulfonylurea receptor: Purification and partial characterization from ovine brain *Proc. Natl. Acad. Sci. USA* 1992 89:6629–66363.

Bernardi et al. ATP/ADP Binding Sites are Present in the Sulfonylurea Binding Protein Associated with Brain ATP–Sensitive $K^+$Channels *Biochemistry* 1992 31:6328–6332.

Boyle et al. Electrophysiological Expression of Ion Channels in Xenopus Oocytes *Methods in Neuroscience* 1991 4:157–173.

Bryan et al. Cloning of a Sulfonylurea Receptor (ATP–Sensitive $K^+$Channel) From Rodent α–and β–Cells Intern'l Conference on ATP–Sensitive $K^+$Channels and Sulfonylurea Receptors, Houston, Tx 1993.

Cole et al. Overexpression of a Transporter Gene in a Multidrug–Resistant Human Lung Cancer Cell Line *Science* 1992 258:1650–1654.

de Weille et al. Activation and Inhibition of ATP–Sensitive $K^+$Channels By Fluorescein Derivatives *J. Biol. Chem* 1992 267:4557–4563.

Edwards et al. The Pharmacology of ATP–Sensitive Potassium Channels *Annu. Rev. Pharmacol. Toxicol.* 1993 33;597–637.

Eisenberg et al. Analysis of Membrane and Surface Protein Sequence with the Hydrophobic Moment Plot *J. Mol. Biol.* 1984 179:125–142 Aug.1, 1997.

Feng et al. Progressive Sequence Alignment as a Prerequisite to Correct Phylogenetic Trees *J. Mol. Evol.* 1987 25:351–360 Aug. 1, 1997.

Gerich J. E. Oral Hypoglycemic Agents *New Engl. J. Med.* 1989 321:1231–1245.

Aguilar–Bryan et al. Synthesis and Characterization of an Iodinated Sulfonylurea *J. Cell Biol* 1988 107:561 Aug. 1, 1997.

Aguilar–Bryan Photoaffinity Labeling of the β cell sulfonylurea Receptor Using a Novel Glyburide Analog Clinical Research National Meeting Apr. 1989 vol. 37.

Aguilar–Bryan Co–Expression of Sulfonylurea Receptors and $K_{ATP}$ Channels: Evidence that a 140 kDa Protein is an Integral Part of this Channel Biophysical Soc. Houston Texas 1992.

Aguilar–Bryan Photoaffinity Labeling and Partial Puriciation of The β Call Sulfonylurea Receptor Using a Novel Biologically Active Glyburide Analogs *J. Biol. Chem.* 1990 265:8218.

Aguilar–Bryan Cloning of a High Affinity Sulfonylurea Receptor From Rodent α–and β–Cells *J. Cell. Biochem. Suppl.* 1994 18:133.

Aguilar–Bryan et al. Co–Expression of Sulfonylurea Receptors and $K_{ATP}$ Channels in Hamster Insulinoma Tumor (HIT) Cells *JBC* 1992 267:14934.

Ashcroft et al. Properties and Functions of ATP–Sensitive K–Channels *Cell Signal.* 1990 2:197–214.

Ashcroft et al. The Sulfonylurea Receptor *Biochim. Biophys. Acta* 1992 1175:45–49.

Ashford et al. Tolbutamide excites rat glucoreceptive ventromedial hypothallamic neurones by indirect inhibition of ATP–$K^+$channels *Br. J. Pharmac.* 1990 101:531–540.

Nelson et al. The High Affinity HIT Cell Sulfonylurea Receptor Intern'l Conference on ATP–Sensitivie $K^-$Channels and Sulfonylurea Receptors, Houston TX, Sep. 30–Oct. 1, 1993.

Vu et al. Pancreatic β–Cell Ion Channels: Role in Diabetes Pathogenesis and Therapy, Amer. Diab. Assoc. 24th Internat'l Res. Symp., Oct. 27, 1989, Marco Island, Florida.

→-Pro -Leu-Ala-Phe -Ser- Gly-Thr-Glu- ?  -His-Ser-Ala-Ala-Tyr-Arg-Val-Asp-Gln-Gly - Val-
→-(Pro)-Leu-Ala-Phe-(Cys)-Gly-Thr-Glu-Asn-His-Ser-Ala-Ala-Tyr-Arg-Val-Asp-Gln-Gly - Val- Leu-Asn-(Asn)-(Gly)-
                    (Ser)                  CHO

-Pro- Leu-Ala-Phe -Ser- Gly-Thr-Glu- ?  -His-Ser-Ala-Ala-Tyr-Arg-Val-Asp-Gln-Gly -
 ?  - Leu-Ala-Phe-(Cys)-Gly-Thr-Glu-  ?  -His-Ser-Ala-Ala-Tyr-Arg-Val-Asp-Gln-(Gly)-(Val)-
 (Pro)-Leu-Ala-Phe-(Cys)-Gly-Thr-Glu- ?  -His-Ser-Ala-Ala-Tyr-Arg-Val-Asp-Gln-Gly -(Val)-Leu-Asn- Asn - (Gly)-(Cys)-(Phe)-(Val)-(Asp)-(Ser)-(Tyr)-

(Pro)-Leu-Ala-Phe-(Cys)-Gly-Thr-Glu- ?  -His-Ser-Ala-Ala-Tyr-Arg-Val-Asp-Gln-Gly - Val -Leu-Asn-(Asn)- Gly -(Pro)-
 Pro -Leu-Ala-Phe- Cys -Gly-Thr-Glu- ?  -His-Ser-Ala-Ala-Tyr-Arg-Val-Asp-Gln-Gly - Val -Leu-Asn- Asn-  Gly -(Cys)-
```

METHODS OF SCREENING FOR PERSISTENT HYPERINSULINEMIC HYPOGLYCEMIA OF INFANCY

REFERENCE TO RELATED APPLICATIONS

This application is a continuation-in-part of U.S. patent application Ser. No. 08/226,972, filed Apr. 13, 1994, now abandoned, the disclosure of which is hereby incorporated by reference in its entirety.

REFERENCE TO GOVERNMENT GRANTS

This work was supported in part by research grants from the National Institutes of Health, grant number NIH R01DK41898 and R01DK44311. The United States Government may have certain rights in this invention.

BACKGROUND OF THE INVENTION

Sulfonylureas are oral hypoglycemics widely used in the treatment of Non-Insulin Dependent Diabetes Mellitus (NIDDM). They enter the bloodstream, bind with high affinity to a pancreatic β-cell plasma membrane protein termed the sulfonylurea receptor, and stimulate insulin release. The mechanism of stimulation is thought to be through inhibition of an ATP-sensitive K+ channel ($K_{ATP}$), a key protein which sets the β-cell resting membrane potential (Ashcroft, et al. Cell. Signal. 1990, 2, 197–214, all references cited herein are incorporated by reference in their entirety). A reduction in potassium outflow causes depolarization of the plasma membrane, activation of L-type voltage-dependent calcium channels (VDCCs), and increased cytosolic calcium. This triggers insulin release by as yet unknown mechanisms (Rajan, et al. Diabetes Care 1990, 13, 340–363). In NIDDM patients on sulfonylureas, the consequent reduction in blood glucose to more normal levels is thought to be critical in controlling the disease (Gerich, J.E. New Engl. J. Med. 1989, 321, 1231–1245).

The biochemistry of the sulfonylurea receptor (SUR) (Ashcroft et al Biochem. Biophys Acta 1992, 1175, 45–49 and Panten et al. Horm. Metab. Res. 1992, 24, 549–554) is consistent with the electrophysiology of the β-cell $K_{ATP}$ channel. The endogenous regulators of channel activity include cytosolic nucleotides (ATP and Mg-ADP) and possibly phosphorylation. In the absence of cytosolic nucleotides, sulfonylureas weakly inhibit channel activity (Schwanstecher et al. Br. J. Pharmacol 1992, 107, 87–94). When channels are activated by Mg-ADP, inhibition by ATP is strongly promoted by the presence of sulfonylureas. These results are interpreted as evidence that simultaneous occupancy of two nucleotide binding sites is required for effective channel inhibition by the sulfonylureas. The reported allosteric interactions correlate well with evidence that the brain receptor has two nucleotide binding sites (de Weille, et al. J. Biol. Chem 1992, 267, 4557–4563) physically located on the same polypeptide chain as the sulfonylurea binding site (Bernardi et al. Biochemistry 1992, 31, 6328–6332). One binding site appears to be specific for ATP, and is proposed to be the same site at which micromolar concentrations of ATP inhibit the $K_{ATP}$ channel. A second site has high affinity for Mg-ADP, with occupancy at this site promoting channel opening. Absolute concentrations of ATP and ADP in the cell are thought to regulate channel activity in a straightforward fashion (Hopkins et al. J. Membrane Biol. 1992, 129, 287–295). High ATP concentrations as a result of high serum glucose levels close the channel, stimulating insulin secretion. Reduced glucose levels increase intracellular ADP concentrations, and thereby increase the open channel probability, and decrease insulin secretion.

Although sulfonylureas, particularly tolbutamide and more potent second generation drugs like glyburide and glipizide, are considered to be relatively specific inhibitors of the $K_{ATP}$ channel, the exact relationship between the sulfonylurea receptor and the $K_{ATP}$ channel is not clear (Nichols et al. Am. J. Physiol. 1991, 261, H1675–H1686, Takano et al. Progress in Neurobiology 1993, 41, 21–30, and Edwards et al. Annu. Rev. Pharmacol. Toxicol. 1993, 33, 597–637). In the insulin-secreting CRI-G1 cell line, the addition of glyburide, or tolbutamide to inside-out plasma membrane patches inhibits the $K_{ATP}$ channel (Khan et al. Proc. R. Soc. Lond. B. 1993, 253, 225–231), intimating direct interactions between sulfonylureas and the channel protein. In another insulin secreting cell line, CRI-D11 cells, however, the loss of sulfonylurea binding sites with the retention of $K_{ATP}$ activity suggests these two activities may uncouple and reside on separate, transiently bound subunits (Khan et al. Proc. R. Soc. Lond. B. 1993, 253, 225–231). Similarly, in other cell and tissue types, sulfonylurea binding and channel activity may be uncoupled (Ashford et al Br. J. Pharmac. 1990, 101, 531–540). A technique is not currently available to assess whether $K_{ATP}$ activity resides within the same polypeptide containing the putative nucleotide and sulfonylurea binding sites, or on separate loosely, or tightly bound subunits.

A previous attempt to purify the receptor from hamster insulin-secreting tumor (HIT) cells was limited by the low abundance of the receptor and the presence of a more abundant co-purifying protein. Aguilar-Bryan, L., et al., JBC, 1990, 265, 8218.

The sulfonylurea receptor is the target for drugs used in the treatment of type II diabetes (non-insulin diabetes mellitus). This association has suggested it plays a role in the regulation of insulin secretion by glucose and makes the sulfonylurea receptor a potential diabetes candidate gene.

Persistent hyperinsulinemic hypoglycemia of infancy (PHHI) is an autosomal recessive disorder of glucose homeostasis characterized by unregulated secretion of insulin and profound hypoglycemia. A. Aynsley-Green et al., Arch. Dis. Child. 1981, 56, 496. The pathophysiology of this disease remains obscure, but in vitro studies suggest a defect of glucose-regulated insulin secretion in pancreatic islet β-cells. Aynsley-Green et al., supra., N. Kaiser et al., Diabetologia 1990, 33, 482. The incidence of PHHI has been estimated at 1/50,000 live births in a randomly mating population. G. J. Bruining, Curr. Opin. Pediatr. 1990, 2, 758. However, in a Saudi Arabian population in which 51% of births occurred to parents who were first or second cousins, the incidence has been established as 1/2675 live births. P. M. Mathew et al., Clin. Pediatr. 1988, 27, 148. Recently, the PHHI gene was assigned to chromosome 11p1415.1 by linkage analysis. B. Glaser et al., Nature Genet. 1994, 7, 185 and P. M. Thomas, G. J. Cote, D. M. Hallman, P. M. Mathew, Am. J. Hum. Genet. 1995, 56, 416–421. Candidate genes for this disorder include those involved in the β-cell glucose sensing mechanism and insulin secretion. Localization of PHHI to chromosome 11p excluded previously mapped genes involved in β-cell function. Considered as a candidate was the newly cloned high-affinity SUR gene, a member of the ATP-binding cassette superfamily, and a putative subunit of the modulator of insulin secretion, the β-cell ATP-sensitive potassium channel ($K_{ATP}$). S. J. Ashcroft and F. M. Ashcroft, Biochimica et Biophysica Acta, 1992, 1175, 45; U. Panten, M. Schwanstecher, and C. Schwanstecher, Horm. Metab. Res. 1992, 24, 549. The methods of the present invention map the sulfonylurea receptor to the same chromosomal location as PHHI and provide evidence that mutations in the sulfonylurea receptor are the cause of PHHI.

Accordingly, there remains a need to identify sulfonylurea receptor and sequences encoding sulfonylurea receptor which will provide:

1. a correlation between sulfonylurea receptor and one or more forms of diabetes,
2. a sequence to purify human sulfonylurea receptors,
3. an isolated sulfonylurea receptor, prepared by recombinant methods,
4. polyclonal and monoclonal antibodies and methods of preparing the same against sulfonylurea receptor,
5. information as to whether this receptor-ion channel family involves multi-subunits within each channel for channel activity,
6. gene therapy such that sequences which encode mutant sulfonylurea receptors are replaced by wild type sulfonylurea receptor sequences,
7. a method of screening to identify drugs which react with and bind to the sulfonylurea receptor,
8. non-human transgenic animals to study diabetes and PHHI, and the physiologic effects of varying levels of sulfonylurea receptor, by using an inducible promoter to regulate the expression of the sulfonylurea receptor, for example, and
9. probes, including PCR probes, for diagnosing conditions associated with the expression of a specific sulfonylurea receptor allele.

The present invention reveals that the sequence encoding the mammalian sulfonylurea receptor maps to the sequence encoding persistent hyperinsulinemic hypoglycemia of infancy.

SUMMARY OF THE INVENTION

The present invention provides sequences encoding a sulfonylurea receptor. Nucleic acid sequences, SEQ ID NOS: 4, 5, 7, and 8 are cDNA sequences to which the present invention is directed. SEQ ID NOS: 4, 5, 7, and 8 are rodent sequences (SEQ ID NOS: 4 and 5—rat, SEQ ID NOS: 7 and 8—hamster) encoding sulfonylurea receptor which functionally bind sulfonylurea. SEQ ID NOS: 1 and 2 are human sequences which encode sulfonylurea receptor. SEQ ID NOS: 2, 5, and 8 set forth DNA sequences translated into amino acid sequences, which set forth below the DNA sequence.

A further aspect of the present invention provides sulfonylurea receptor polypeptides and/or proteins. SEQ ID NOS:3, 6, 9, 28, 29, are novel polypeptides of the invention produced from nucleotide sequences encoding rat (SEQ ID NOS: 5, 6 and 27), hamster (SEQ ID NOS: 7 and 8), and human (SEQ ID NOS: 1 and 2) sulfonylurea receptor, respectively. Also within the scope of the present invention is a purified sulfonylurea receptor.

The present invention also provides nucleic acid sequences encoding a sulfonylurea receptor, expression vectors comprising a nucleic acid sequence encoding a sulfonylurea receptor, transformed host cells capable of expressing a nucleic acid sequence encoding a sulfonylurea receptor, cell cultures capable of expressing a sulfonylurea receptor, and protein preparations comprising a sulfonylurea receptor.

A method of detecting persistent hyperinsulinemic hypoglycemia of infancy comprising obtaining a sample comprising patient nucleic acids from a patient tissue sample; amplifying sulfonylurea receptor specific nucleic acids from said patient nucleic acids to produce a test fragment; obtaining a sample comprising control nucleic acids from a control tissue sample; amplifying control nucleic acids encoding wild type sulfonylurea receptor to produce a control fragment; comparing the test fragment with the control fragment to detect the presence of a sequence difference in the test fragment, wherein a difference in said test fragment indicates persistent hyperinsulinemic hypoglycemia of infancy is also an embodiment of the present invention.

Other methods of the present invention include a method of detecting persistent hyperinsulinemic hypoglycemia of infancy comprising obtaining a sample comprising patient mRNA from a patient tissue sample; reverse transcribing said mRNA into cDNA to produce patient cDNA; amplifying sulfonylurea receptor specific cDNA from said patient cDNA to produce amplified patient cDNA; obtaining a sample comprising control nucleic acids from a control tissue sample; amplifying control DNA encoding wild type sulfonylurea receptor to produce control cDNA; digesting said test fragment and said control fragment with a selected endonuclease; and comparing the test fragment to the control fragment, wherein said test fragment indicates persistent hyperinsulinemic hypoglycemia of infancy.

Another embodiment of the present invention is a diagnostic kit for detecting persistent hyperinsulinemic hypoglycemia of infancy comprising in one or more containers a pair of primers, wherein one primer within said pair is complementary to a region of the sulfonylurea receptor, wherein one of said pair of primers is selected from the group consisting of SEQ ID NOS: 12–20, a probe specific to the amplified product, and a means for visualizing amplified DNA, such as and not limited to fluorescent stain, $^{32}P$, and biotin, and optionally including one or more size markers, positive and negative controls, and restriction endonucleases.

Still another embodiment of the present invention includes the primer sequences identified in SEQ ID NOS: 12–20.

BRIEF DESCRIPTION OF THE DRAWINGS

FIGS. 1A and 1B displays characteristics of the purified HIT cell receptor. The radiolabeled receptor (lanes 1 and 3) cleaved with endoglycosidase F/N-glycosidase F (endo F), increases the mobility of the protein by approximately 3 kDa (lane 2). Subsequent partial V8 protease digestion (lanes 4 and 6) yielded radiolabeled fragments that also shift mobility with endo F treatment (lane 5). Each of these species has the same N-terminal sequence, except that receptor deglycosylation results in an Asp at residue 9. The amino acid sequences set forth in FIG. 1 are SEQ ID NOS: 33, 34, 35, 36, 37, 38, and 39.

Multiple antigenic peptides (MAPS) were synthesized (Posnett et al. *J. Biol. Chem.* 1988 263:1719–1725) and polyclonal antibodies generated in rabbits produced by standard methods (Antibodies: A Laboratory Manual Cold Spring Harbor Laboratory 1988). Interdermal injections of 1 mg of antigen were spaced 2–3 weeks apart, and contained complete, or incomplete Freund's adjuvant.

Figure 3:
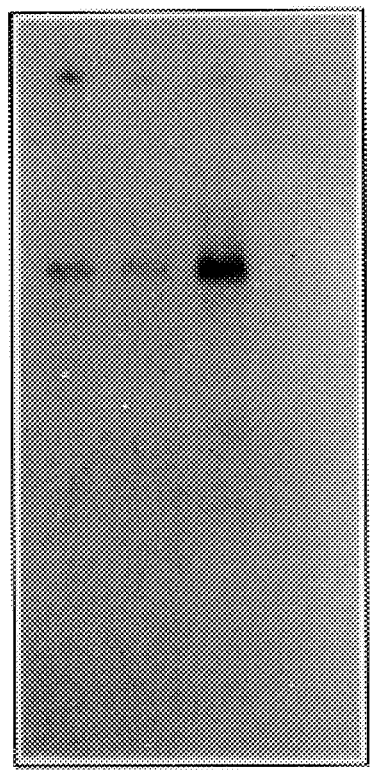

FIG. 3 is a northern blot of total RNA from α- and β-cell lines hybridized with a 2.2 kb EcoRI-XhoI fragment of the sulfonylurea receptor. Approximately 10 μg of RNA from (A) αTC-6 cells, (B) HIT cells, (C) RIN cells and (D) mouse liver was analyzed using standard procedures (Ausubel et al. *Current Protocols in Mol. Biol.* 1994). The estimated size of the major component is approximately 5000 nucleotides.

Figure 4:
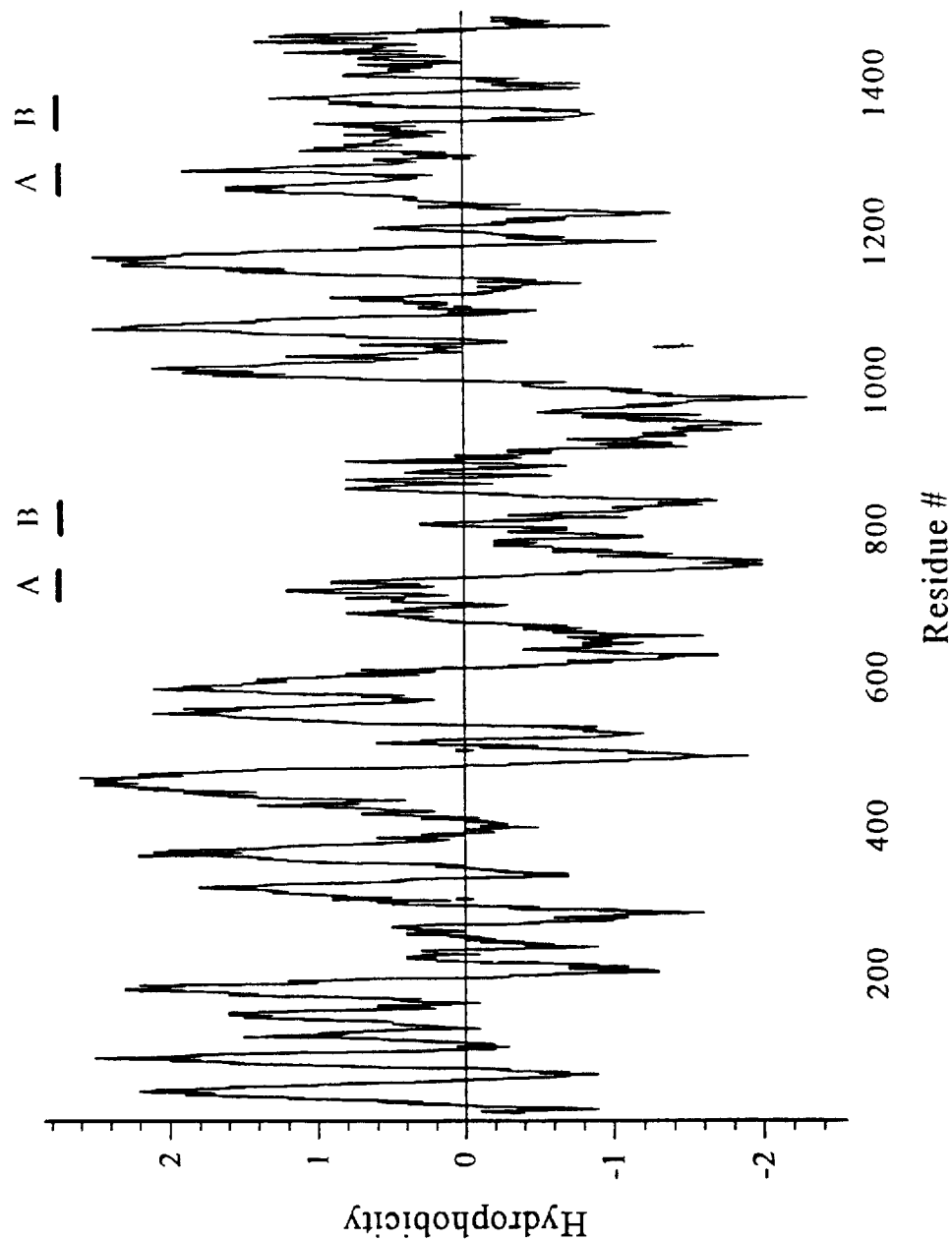

FIG. 4 displays a hydrophobicity profile of the Rat Sulfonylurea receptor. Hydrophobicity values were determined according to Kyte and Doolittle (Kyte et al. *J. Mol. Biol.* 1982 157:105–132) for 11-residue peptides and are plotted versus the amino acid number. The bars marked A and B are over the Walker A and B consensus sequences (Walker et al. *EMBO Jour.* 1982 1:945–951).

Figure 5:
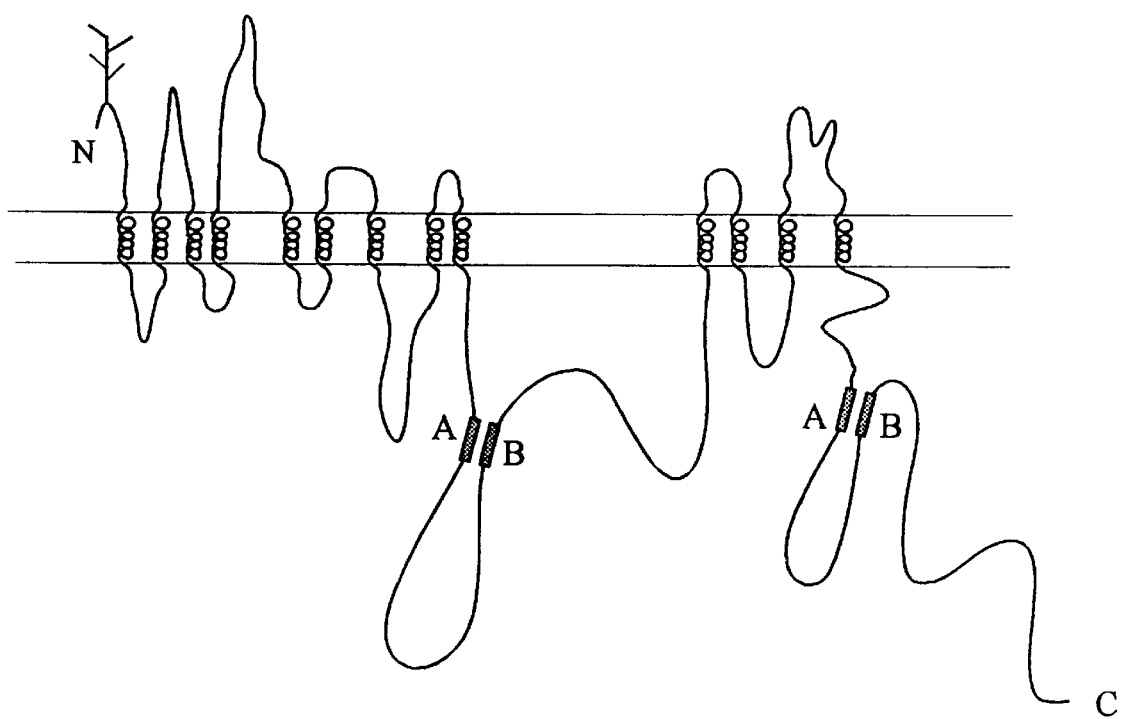

FIG. 5 shows a schematic model of the high affinity sulfonylurea receptor. The Walker A and B sites are marked within the two nucleotide binding folds. Based on the hydrophobicity and hydrophobic moment data there are nine transmembrane spanning domains before the first nucleotide binding fold and four transmembrane spanning domains between the two folds. The branched structure at the N-terminus of the mature receptor symbolizes glycosylation.

Figure 6A:
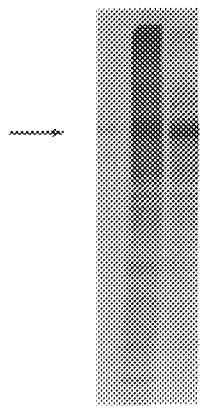

FIG. 6A reveals the results of in vitro translation of mRNA transcribed from the rat sulfonylurea cDNA. The cDNA was subcloned into pGEM4 (Promega, Inc., Madison, Wis.) and transcribed using the SP6 promoter and SP6 RNA polymerase following the manufacturer's directions. RNA was translated in rabbit reticulocyte lysate (Promega, Inc.) following the manufacturer's recommendations for $^{35}$S-methionine. Lane 1 is the HIT cell photolabeled receptor as a marker, lane 2 is the in vitro translation product resulting from addition of receptor mRNA and lane 3 is the result of no added RNA. The arrow marks the 140 kDa protein.

Figure 6B:
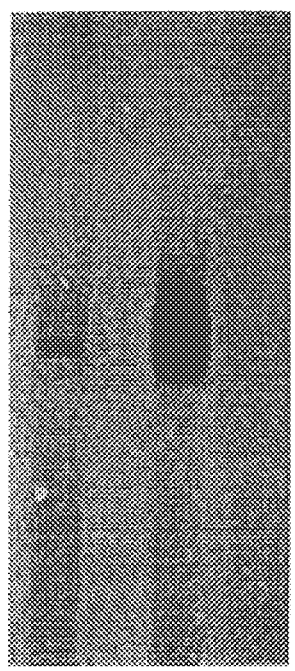

FIG. 6B displays a gel of the results of immunoprecipitation of the RIN cell sulfonylurea receptors with polyclonal antibodies directed against a nucleotide binding fold domain (NBF). Lane 1; 140 and 150 kDa receptors from soluble RIN cell membrane proteins, lane 2: immunoprecipitation with preimmune serum, lane 3; immune serum from rabbit immunized with NBF2, lane 4; immune serum+NBF2 fusion protein. Sulfonylurea receptor CDNA regions encoding the NBF2 domain were subcloned in frame into pMALc and expression of the proteins fused with maltose binding protein induced in *E. coli*. Fusion proteins were purified by electrophoresis and electroelution, and 200 μg amounts, with complete, or incomplete Freund's adjuvant, injected intradermally into rabbits using a standard 2–3 week regimen of bleeding and boosting.

Figure 7:
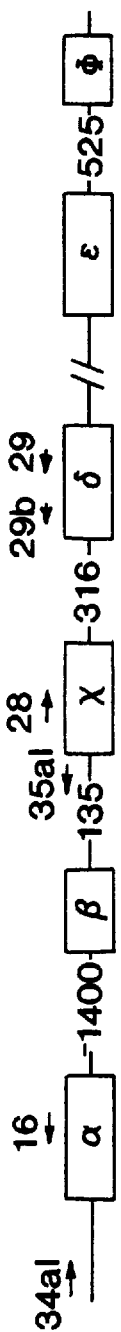

FIG. 7 displays the genomic organization of the human sulfonylurea receptor (SUR) homologue in the second nucleotide binding fragment region (NBF-2). The sequence encoding NBF-2 is located within SEQ ID NO: 1, nucleic acid positions 524 to 1048. Solid rectangles represent exons which are labeled α-ø for identification. The numbers between rectangles represent intronic sizes. Primers used in mutational analysis are diagrammed and listed in the arrows as Primer 17=SEQ ID NO: 13; Primer 34a1=SEQ ID NO: 17; Primer 16=SEQ ID NO: 12; Primer 35a1=SEQ ID NO: 18; Primer 28=SEQ ID NO: 14; Primer 29b=SEQ ID NO: 16; Primer 29=SEQ ID NO: 15.

Figure 8A:
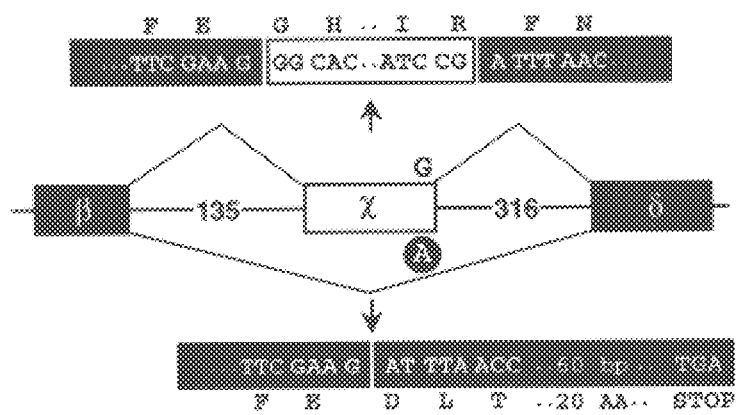
Figure 8B:
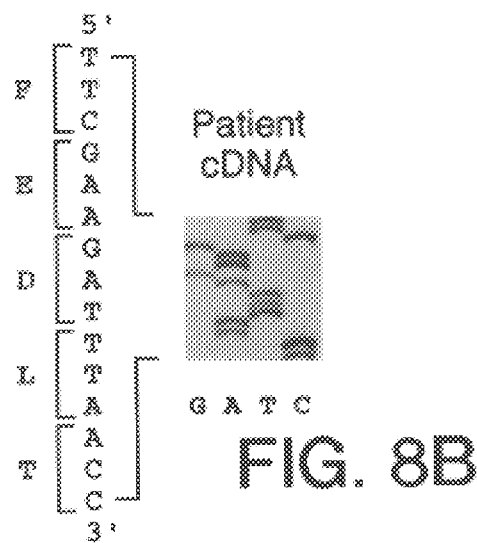
Figure 8C:
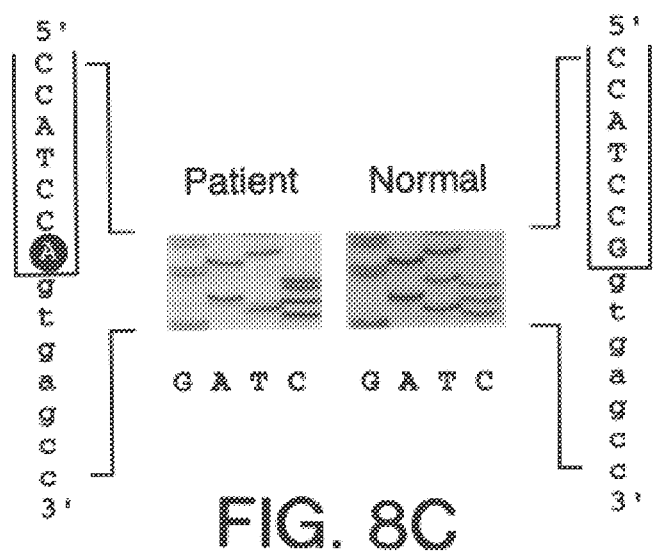
Figure 8D:
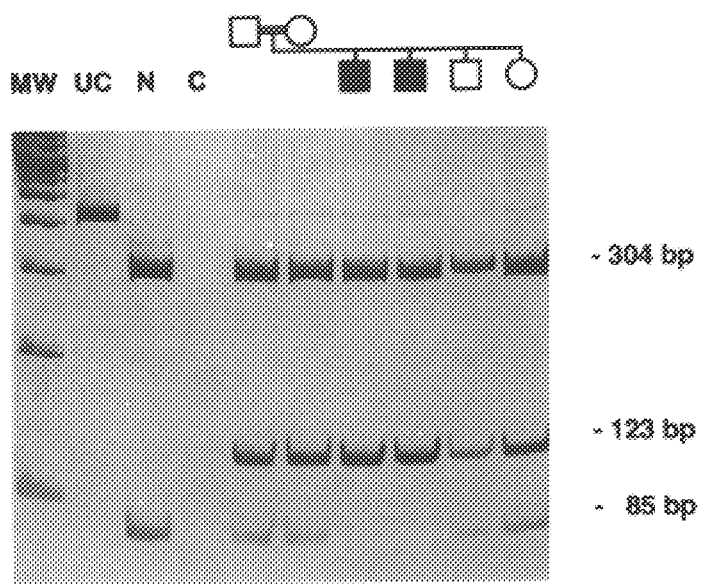

FIG. 8A–D display the exon mutation in the SUR NBF-2. FIG. 8A is a schematic representation of NBF-2 exons β, X, δ illustrating the normal (upper) and mutant (lower) RNA splicing patterns SEQ ID NOS: 40, 41, 42 and 43. FIG. 8B displays the sequence of a pancreatic cDNA product and corresponding amino acid sequence, SEQ ID NOS: 44 and 45, respectively, from an affected child of Family 6, demonstrating the exon skipping event. Skipping of exon X results in a 109 bp deletion in the mRNA transcript, a frame shift and inclusion of a premature stop codon. Single upper case letters represent amino acids. FIG. 8C shows the sequence of genomic DNA from the affected patient in FIG. 8B which reveals a G to A point mutation at the 3' end of the exon, which exon is excised in mRNA, as compared to a normal sample of genomic DNA. Exonic sequence is in upper case and intronic sequence in lower case letters SEQ ID NO: 47. FIG. 8D shows MspI restriction enzyme analysis of PCR-amplified genomic DNA from members of Family 6, indicating affected individuals. The G to A mutation destroyed a restriction site for MspI (C/CGG). Normal PCR product is digested into 304 bp, 85 bp, and 38 bp fragments, while that containing the mutation is digested into 304 bp and 123 bp fragments. MW is 100 bp ladder (GIBCO-BRL, Gaithersburg, Maryland), UC is an uncut sample, C is a control PCR reaction lacking template.

Figure 9A:
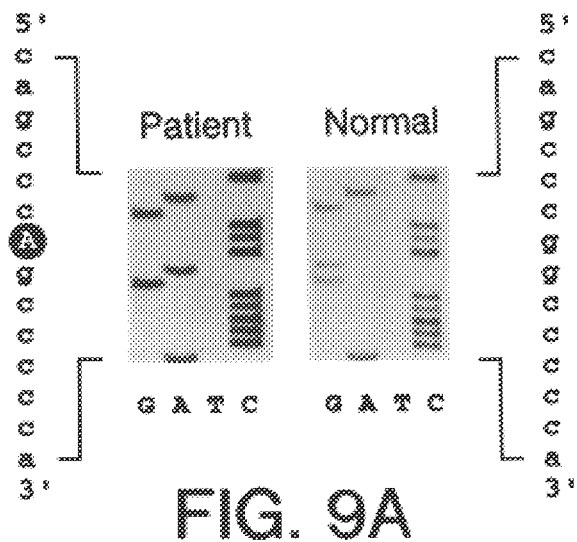
Figure 9B:
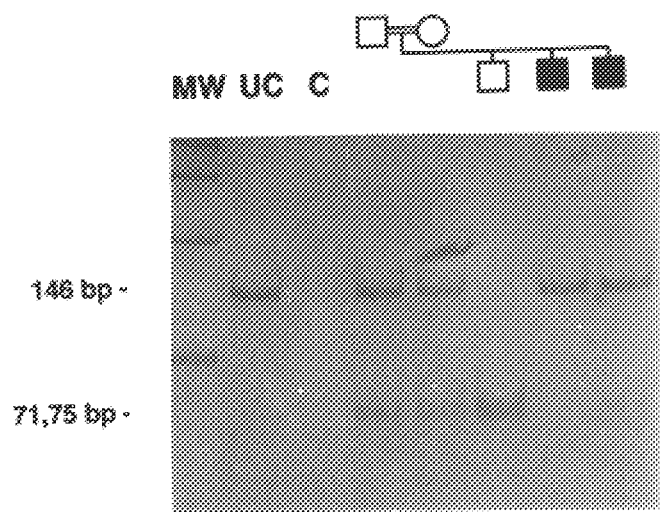
Figure 9C:
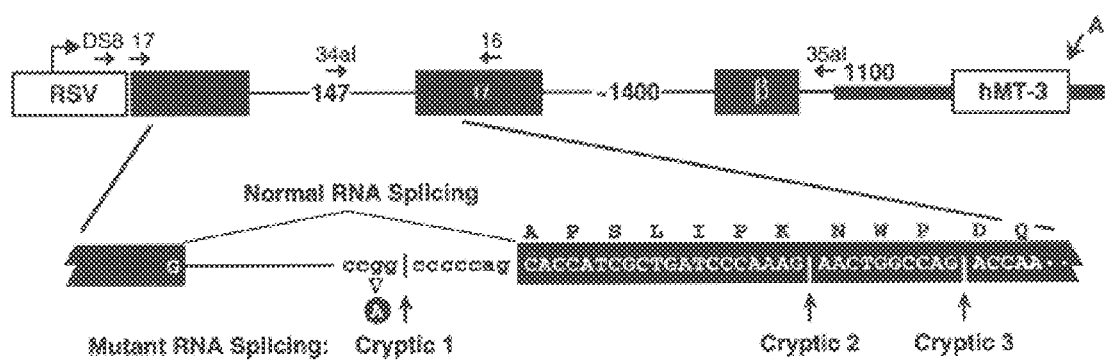
Figure 9D:
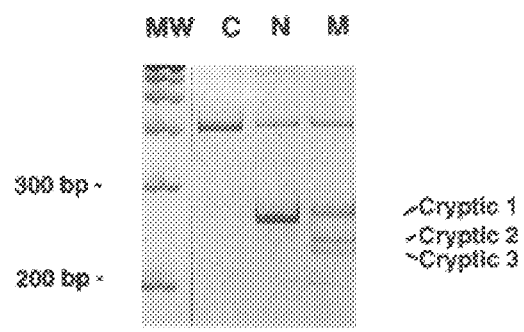

FIG. 9A–D reveal a mutation in the intron preceding NBF-2 exon α, which activates cryptic 3' splice site usage. FIG. 9A displays the sequence of genomic DNA from an affected member of Family 4 which revealed a G to A mutation in the splice site preceding the first exon of the NBF-2 SEQ ID NO: 47. FIG. 9B shows NciI restriction enzyme analysis of genomic DNA from members of Family 4, indicating affected individuals. The G to A mutation destroys a restriction site for NciI (CC/(G/C)GG). Normal PCR product is digested into 71 bp and 75 bp fragments, while that containing the mutant sequence is not cut MW is a molecular weight marker, UC is an uncut sample, C is a control reaction. By previous haplotype analysis, the unaffected sibling in this family had two wild type alleles, P. M. Thomas, G. J. Cote, D. M. Hallman, P. M. Mathew, *Am. J. Hum. Genet.*, supra. FIG. 9C illustrates the constructs used to examine RNA processing of exons within NBF-2. Solid rectangles and thin lines represent human SUR gene exonic and intronic sequences, respectively. The unmarked solid rectangle represents a portion of the exon which is 5' to exon a of the NBF-2 region. The rectangle labeled RSV represents the enhancer and promoter isolated from the rous sarcoma virus long terminal repeat. The thick line represents an intronic sequence derived from vector and the human met-allothionine IIA gene, which also contains polyadenylation signals. Normal and mutant RNA splicing patterns, including the location of the three cryptic splice sites, are diagrammed in the lower portion along with SEQ ID NOS: 48 and 49. The open triangle marks the position of the mutated base within the splice site. FIG. 9D shows PCR amplification across splice site of normal (N) and mutant (M) cDNA transcripts, isolated 48 hours after transfection with the splicing constructs. Subcloning and sequencing of these products revealed their identity as diagrammed in FIG. 9C. The control (C) represents CDNA amplified from untransfected cells.

FIG. 10 depicts pCR™ 11 vector.

DETAILED DESCRIPTION OF THE INVENTION

The present invention is directed to the nucleic acid and protein sequences encoding a sulfonylurea receptor. The present invention provides nucleotide sequences of a sulfonylurea receptor, and SEQ ID NOS: 5, 8, and 27. Novel polypeptide sequences, SEQ ID NOS: 3, 6, 9, 27, 28 and 29 coding for a sulfonylurea receptor are also included in the present invention. SEQ ID NOS: 1 and 2 provide the nucleic acid and amino acid sequences of the last 11 exons of the 3' end of human sulfonylurea receptor, hereinafter referred to, together with the rodent sequences for sulfonylurea receptor, as sequence for the sulfonylurea receptor.

SEQ ID NOS: 4, 5, 7 and 8 provide the cDNA sequences of rodent sulfonylurea receptor. SEQ ID NOS: 1 and 2 provide the human cDNA and DNA sequence of sulfonylurea receptor, respectively. Nucleic acids within in the scope of the present invention include cDNA, RNA, genomic DNA, sequences within these larger sequences, antisense oligonucleotides. Sequences encoding the sulfonylurea receptor also include amino acid, polypeptide, and protein sequences. Variations in the nucleic acid and polypeptide sequences of the present invention are within the scope of the present invention and include N terminal and C terminal extensions, transcription and translation modifications, and modifications in the cDNA sequence to facilitate and improve transcription and translation efficiency. In addition, mismatches within the sequences identified herein, which achieve the methods of the invention, such that the mismatched sequences are substantially complementary to the sulfonylurea receptor sequences identified, are also considered within the scope of the present invention. Mismatches which permit substantial complementarity to the sulfonylurea receptor sequences, such as similarity in residues in hydrophobicity, will be known to those of skill in the art once armed with the present disclosure. In addition, the sequences of the present invention may be natural or synthetic.

A purified sulfonylurea receptor is also provided by the present invention. The purified sulfonylurea receptor may have an amino acid sequence as provided by SEQ ID NOS: 3, 6, 9, 27, 28 and 29.

The present invention is directed to sulfonylurea receptor sequences obtained from mammals from the Order Rodentia, including and not limited to hamsters, rats, and mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

There are several transfection techniques by which a sulfonylurea receptor may be obtained. An appropriate RNA may be hybridized to a cDNA to obtain a sulfonylurea receptor nucleic acid sequence. A nucleic acid sequence encoding sulfonylurea receptor may be inserted into cells and the corresponding protein immunoprecipitated with an antibody. Labeled drugs known to bind sulfonylurea receptor protein may be added to cell culture to label the receptor. The drug labeling procedure may involve modifying cells such that the cell culture provides conditions similar to β cells, cells where sulfonylurea receptors naturally appear; and the sulfonylurea receptor may be part of a larger multisubunit ATP receptor channel, which may not be provided by the cells in culture.

Generally, the sequences of the invention may be produced in host cells transformed with an expression vector comprising a nucleic acid sequence encoding the sulfonylurea receptor. The transformed cells are cultured under conditions whereby the nucleic acid sequence coding for the sulfonylurea receptor is expressed. After a suitable amount of time for the protein to accumulate, the protein is purified from the transformed cells.

A gene coding for sulfonylurea receptor may be obtained from a cDNA library. Suitable libraries can be obtained from commercial sources such as Clontech, Palo Alto, Calif. Libraries may also be prepared using the following non-limiting examples hamster insulin-secreting tumor (HIT), mouse αTC-6, and rat insulinoma (RIN) cells. Positive clones are then subjected to DNA sequencing to determine the presence of a DNA sequence coding for sulfonylurea receptor. DNA sequencing is accomplished using the chain termination method of Sanger et al., *Proc. Nat'l. Acad. Sci, U.S.A.*, 1977, 74, 5463. The DNA sequence encoding sulfonylurea receptor is then inserted into an expression vector for later expression in a host cell.

Expression vectors and host cells are selected to form an expression system capable of synthesizing sulfonylurea receptor. Vectors including and not limited to baculovirus vectors may be used in the present invention. Host cells suitable for use in the invention include prokaryotic and eukaryotic cells that can be transformed to stably contain and express sulfonylurea receptor. For example, nucleic acid coding for the recombinant protein may be expressed in prokaryotic or eukaryotic host cells, including the most commonly used bacterial host cell for the production of recombinant proteins, *E. coli*. Other microbial strains may also be used, however, such as *Bacillus subtilis*, and other enterobacteriaceae such as *Salmonella typhimurium* or *Serratia marcescens*, various species of Pseudomonas, or other bacterial strains.

Commonly used eukaryotic systems include yeast, such as *Saccharomyces cerevisiae*; insect cells, such as *Spodoptera frugiperda*; chicken cells, such as E3C/O and SL-29; mammalian cells, such as HeLa, Chinese hamster ovary cells (CHO), COS-7 or MDCK cells and the like. The foregoing list is illustrative only and is not intended in any way to limit the types of host cells suitable for expression of the nucleic acid sequences of the invention.

As used herein, expression vectors refer to any type of vector that can be manipulated to contain a nucleic acid sequence coding for sulfonylurea receptor, such as plasmid expression vectors and viral vectors. The selection of the expression vector is based on compatibility with the desired host cell such that expression of the nucleic acid encoding sulfonylurea receptor results. Plasmid expression vectors comprise a nucleic acid sequence of the invention operably linked with at least one expression control element such as a promoter. In general, plasmid vectors contain replicon and control sequences derived from species compatible with the host cell. To facilitate selection of plasmids containing nucleic acid sequences of the invention, plasmid vectors may also contain a selectable marker such as a gene coding for antibiotic resistance. Suitable examples include the genes coding for ampicillin, tetracycline, chloramphenicol or kanamycin resistance.

Suitable expression vectors, promoters, enhancers, and other expression control elements are known in the art and may be found in Sambrook et al., *Molecular Cloning: A Laboratory Manual*, second edition, Cold Spring Harbor Laboratory Press, Cold Spring Harbor, N.Y. (1989), incorporated herein by reference in its entirety.

Transformed host cells containing a DNA sequence encoding sulfonylurea receptor may then be grown in an appropriate medium for the host. The cells are then grown until product accumulation reaches desired levels at which time the cells are then harvested and the protein product purified in accordance with conventional techniques. Suitable purification methods include, but are not limited to, SDS PAGE electrophoresis, phenylboronate-agarose, reactive green 19-agarose, concanavalin A sepharose, ion exchange chromatography, affinity chromatography, electrophoresis, dialysis and other methods of purification known in the art.

Protein preparations, of purified or unpurified sulfonylurea receptor produced by host cells, are accordingly produced which comprise sulfonylurea receptor and other material such as host cell components and/or cell medium, depending on the degree of purification of the protein.

Antibodies, including and not limited to monoclonal, polyclonal, and chimeric, prepared and used against a sulfonylurea receptor are also within the scope of the present invention, and may be prepared by methods known to those of skill in the art such as and not limited to the methods of Kohler and Milstein, *Nature*, 256: 495–497 (1975), incorporated herein by reference in its entirety.

The invention also includes a transgenic non-human animal, including and not limited to mammals, such as and not limited to a mouse, rat, or hamster, whose germ cells and somatic cells contain a sequence encoding a sulfonylurea receptor introduced into the animal or an ancestor of the animal. The sequence may be wild-type or mutant and may be introduced into the animal at the embryonic or adult stage. The sequence is incorporated into the genome of an animal such that it is chromosomally incorporated into an activated state. Embryo cells may be transfected with the gene as it occurs naturally, and transgenic animals are selected in which the gene has integrated into the chromosome at a locus which results in activation. Other activation methods include modifying the gene or its control sequences prior to introduction into the embryo. The embryo may be transfected using a vector containing the gene.

In addition, a transgenic non-human animal may be engineered wherein the sulfonylurea receptor is suppressed. For purposes of the present invention, suppression of the sulfonylurea receptor includes, and is not limited to strategies which cause the sulfonylurea receptor not to be expressed. Such strategies may include and are not limited to inhibition of protein synthesis, pre-mRNA processing, or DNA replication. Each of the above strategies may be accomplished by antisense inhibition of sulfonylurea receptor gene expression. Many techniques for transfering antisense sequences into cells are known to those of skill, including and not limited to microinjection, viral-mediated transfer, somatic cell transformation, transgene integration, and the like, as set forth in Pinkert, Carl, *Transgenic Animal Technology*, 1994, Academic Press, Inc., San Diego, Calif., incorporated herein by reference in its entirety.

Further, a transgenic non-human animal may be prepared such that the sulfonylurea receptor gene is knocked out. For purposes of the present invention, a knock out includes and is not limited to disruption or rendering null the sulfonylurea receptor gene. A knock out may be accomplished, for example, with antisense sequences for the sulfonylurea receptor mutating the sequence for the sulfonylurea receptor. The sulfonylurea receptor gene may be knocked out by injection of an antisense sequence for all or part of the sulfonylurea receptor sequence such as an antisense sequence for all or part of SEQ ID NO: 2. Once the sulfonylurea receptor has been rendered null, correlation of the sulfonylurea receptor to persistent hyperinsulinemic hypoglycemia of infancy may be tested. Sequences encoding mutations affecting the sulfonylurea receptor may be inserted to test alterations in glucose homeostasis.

Also in transgenic non-human animals, the sulfonylurea receptor may be replaced by preparing a construct having an insulin promoter ligated to the sulfonylurea receptor gene. This experiment permits testing of mutant sulfonylurea receptors directly in the pancreas of the transgenic animal.

Transgenic non-human animals may also be useful for testing nucleic acid changes to identify nucleotides which are responsible for ADP and ATP modulation of the sulfonylurea receptor resulting in an increase or decrease in glucose sensitivity of insulin release.

The present invention is also directed to gene therapy wherein a mutant sulfonylurea receptor is replaced by a wild type sulonylurea receptor. A resulting transgenic non-human animal thus comprises a recombinant sulfonylurea receptor. In addition, gene therapy techniques may be used for individuals with persistent hyperinsulinemic hypoglycemia of infancy. For purposes of the present invention, gene therapy refers to the transfer and stable insertion of new genetic information into cells for the therapeutic treatment of diseases or disorders. The foreign gene is transferred into a cell that proliferates to spread the new gene throughout the cell population. Known methods of gene transfer include microinjection, electroporation, liposomes, chromosome transfer, transfection techniques, calcium-precipitation transfection techniques, and the like.

Numerous techniques are known in the art for the introduction of foreign genes into cells and may be used to construct the recombinant cells for purposes of gene therapy, in accordance with this embodiment of the invention. The technique used should provide for the stable transfer of the heterologous gene sequence to the stem cell, so that the heterologous gene sequence is heritable and expressible by stem cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, M. J., 1985, Pharmac. Ther. 29:69–92, incorporated herein by reference in its entirety).

The term "purified", when used to describe the state of nucleic acid sequences of the invention, refers to nucleic acid sequences substantially free of nucleic acid not coding for sulfonylurea receptor or other materials normally associated with nucleic acid in non-recombinant cells, i.e., in its "native state."

The term "purified" or "in purified form" when used to describe the state of a sulfonylurea receptor, protein, polypeptide, or amino acid sequence, refers to sulfonylurea receptor sequences free, to at least some degree, of cellular material or other material normally associated with it in its native state. Preferably the sequence has a purity (homogeneity) of at least about 25% to about 100%. More preferably the purity is at least about 50%.

To begin to elucidate the relationship between the sulfonylurea receptor and $K_{ATP}$, the iodinated derivative of glyburide was to identify, and subsequently to purify and obtain N-terminal amino acid sequence from the 140 kDa high affinity, hamster insulin-secreting tumor (HIT) cell sulfonylurea receptor. The peptide sequence data was used to clone full length cDNAs encoding the rat and hamster β-cell proteins of the present invention.

Another embodiment of the present invention is a method of detecting persistent hyperinsulinemic hypoglycemia of infancy comprising obtaining a sample comprising patient nucleic acids from a patient tissue sample; amplifying sulfonylurea receptor specific nucleic acids from said patient nucleic acids to produce a test fragment; obtaining a sample comprising control nucleic acids from a control tissue sample; amplifying control nucleic acids encoding wild type sulfonylurea receptor to produce a control fragment; comparing the test fragment with the control fragment to detect the presence of a sequence difference in the test fragment, wherein a difference in said test fragment indicates persistent hyperinsulinemic hypoglycemia of infancy is also an embodiment of the present invention.

Persistent hyperinsulinemic hypoglycemia of infancy (PHHI) is an autosomal recessive disorder which results in unregulated insulin secretion. The present invention revealed several different mutations in the sulfonylurea receptor in individuals with PHHI. These mutations include nucleic acid transition and restriction fragment length polymorphism, both defined herein as sequence differences. The nucleic acid sequence transition may be a G to A transition at nucleic acid position 750 in SEQ ID NO: 1 which results in PHHI. This transition was found to occur in nine affected children in nine different families of the families studied. The pancreatic cDNA from a child with this transition involved skipping an exon. Genomic DNA template was amplified to obtain the product for Msp I digestion for testing and confirmation of the mutation at position 750 in SEQ ID NO: 1. Exon X of FIG. 7 was skipped resulting in an mRNA transcript having a 109 bp deletion, a frame shift, and the inclusion of a premature stop codon. This deletion may be seen by performing rtPCR on the child's mRNA. Amplification of SEQ ID NO: 1 with primer sequences of SEQ ID NOS: 18 resulted in a 427 base pair product for the normal as well as for the mutant cDNA. Digesting the normal and mutant products with MspI, however, resulted in three fragments (304 bp, 85 bp, and 38 bp) for the normal gene and two fragments (304 bp and 123 bp) for the mutant gene of affected children.

Another mutation involves a G to A transition in intron 11 of the human sulfonylurea receptor which gives rise to PHHI. The transition site corresponds to position 27 of SEQ ID NO: 31. The G to A transition destroys a restriction site for NciI. Both normal and mutant PCR products resulted in 146 bp. Digestion with NciI resulted in two fragments (71 bp and 75 bp) fragments for normal individuals, while the mutant sequence was not be cut by NciI and thus remained at 146 bp.

A method of detecting persistent hyperinsulinemic hypoglycemia of infancy comprising obtaining a sample comprising patient genomic DNA from a patient tissue sample; amplifying sulfonylurea receptor specific DNA from said patient genomic DNA to produce a test fragment; obtaining a sample comprising control nucleic acids from a control tissue sample; amplifying control DNA encoding wild type sulfonylurea receptor to produce a control fragment; comparing the test fragment with the control fragment to detect a test fragment having G to A transition at nucleic acid position 750 of SEQ ID NO: 1, or a G to A transition at nucleic acid position 27 of SEQ ID NO: 31, wherein said test fragment indicates persistent hyperinsulinemic hypoglycemia of infancy is also an embodiment of the present invention.

Also within the scope of the present invention is a method of detecting persistent hyperinsulinemic hypoglycemia of infancy comprising obtaining a sample comprising patient genomic DNA from a patient tissue sample; amplifying sulfonylurea receptor specific DNA from said patient genomic DNA to produce a test fragment; obtaining a sample comprising control nucleic acids from a control tissue sample; amplifying control DNA encoding wild type sulfonylurea receptor to produce a control fragment; digesting said test fragment and said control fragment with an endonuclease selected from the group consisting of NciI and MspI; and comparing the test fragment with the control fragment to detect a restriction fragment length polymorphism, wherein said restriction fragment length polymorphism indicates persistent hyperinsulinemic hypoglycemia of infancy.

The restriction fragment polymorphisms include test fragments of about 304 bp and about 123 bp as a result of MspI restriction and a test fragment of about 146 bp as a result of NciI restriction. The test fragments thus indicate persistent hyperinsulinemic hypoglycemia of infancy.

In accordance with methods of the present invention, methods of detecting PHHI in a patient are provided comprising obtaining a patient tissue sample for testing. The tissue sample may be solid or liquid, a body fluid sample such as and not limited to blood, serum, saliva, sputum, mucus, bone marrow, urine, lymph, and a tear; and feces. In addition, a tissue sample such as pancreatic tissue may be provided for the detection of PHHI in accordance with the present invention.

A test fragment is defined herein as an amplified sample comprising sulfonylurea receptor specific nucleic acids from a patient suspected of having PHHI. A control fragment is an amplified sample comprising normal or wild type sulfonylurea receptor specific nucleic acids from an individual not suspected of having PHHI.

The method of amplifying nucleic acids may be the polymerase chain reaction using a pair of primers wherein at least one primer within the pair is selected from the group consisting of SEQ ID NO: 12–20. When the polymerase chain reaction is the amplification method of choice, a pair of primers may be used such that one primer of the pair is selected from the group consisting of SEQ ID NOS: 13, 14, 17, and 19 and the second primer of the pair is selected from the group consisting of SEQ ID NOS: 12, 15, 16, 18, and 20.

Nucleic acids, such as DNA (such as and not limited to genomic DNA and cDNA) and/or RNA (such as and not limited to mRNA), are obtained from the patient sample.

Preferably RNA is obtained. A whole blood gradient may be performed to isolate nucleated cells and total RNA is extracted such as by the RNazole B method (Tel-Test Inc., Friendswood, Tex.) or by modification of any methods known in the art such as described in Sambrook et al., *Molecular Cloning: A Laboratory Manual,* 1989, Cold Spring Harbor Laboratory, Cold Spring Harbor, N.Y., incorporated herein by reference in its entirety.

Nucleic acid extraction is followed by amplification of the same by any technique known in the art. The amplification step includes the use of at least one primer sequence which is complementary to a portion of sulfonylurea receptor specific expressed nucleic acids or sequences. Primer sequences useful in the amplification methods include and are not limited to SEQ ID NOS: 12–20, which may be used in the amplification methods. Any primer sequence of about 10 nucleotides to about 35 nucleotides, more preferably about 15 nucleotides to about 30 nucleotides, even more preferably about 17 nucleotides to about 25 nucleotides may be useful in the amplification step of the methods of the present invention. In addition, mismatches within the sequences identified above, which achieve the methods of the invention, such that the mismatched sequences are substantially complementary and thus hybridizable to the sequence sought to be identified, are also considered within the scope of the disclosure. Mismatches which permit substantial similarity to SEQ ID NOS: 12–20, such as and not limited to sequences with similar hydrophobicity and hydrophilicity, will be known to those of skill in the art once armed with the present disclosure. The primers may also be unmodified or modified. Primers may be prepared by any method known in the art such as by standard phosphoramidite chemistry. See Sambrook et al., supra.

The method of amplifying nucleic acids may be the polymerase chain reaction using a pair of primers wherein at least one primer within the pair is selected from the group consisting of SEQ ID NO: 12–20. When the polymerase chain reaction is the amplification method of choice, a pair of primers may be used such that one primer of the pair is selected from the group consisting of SEQ ID NOS: 12–20.

Primers used in mutational analysis were SEQ ID NO: 12: CACGCTCAGGTTCTGGAT; SEQ ID NO: 13: TCAACTGGATGGTGAGGA; SEQ ID NO: 14: 5' TGA-CATCGCCAAACTGC; SEQ ID NO: 15: TCCTGGCAGT-GCCTTCA; SEQ ID NO: 16: TCCTCTCAGGGTCCAG-GTTA; SEQ ID NO: 17: ACAAGGAGCCTGGGGAT; SEQ ID NO: 18: TGCATGGGTCCCAGTGA; SEQ ID NO: 19: TTGACCATTCACCACATTGGTGTGC; and SEQ ID NO: 20: TCCTGGCAGTGCCTTCA.

When an amplification method includes the use of two primers, a first primer and a second primer, such as in the polymerase chain reaction, the first primer may be selected from the group consisting of SEQUENCE ID NOS: 13, 14, 17, and 19; and the second primer may be selected from the group consisting of SEQUENCE ID NOS: 12, 15, 16, 18, and 20. Any primer pairs which transcribe nucleic acids toward each other and which are specific for sulfonylurea receptor may be used in accordance with the methods of the present invention.

Total extraction of RNA is preferably carried out. As used herein, the term "amplification" refers to template-dependent processes and vector-mediated propagation which result in an increase in the concentration of a specific nucleic acid molecule relative to its initial concentration, or in an increase in the concentration of a detectable signal. As used herein, the term template-dependent process is intended to refer to a process that involves the template-dependent extension of a primer molecule. The term template dependent process refers to nucleic acid synthesis of an RNA or DNA molecule wherein the sequence of the newly synthesized strand of nucleic acid is dictated by the well-known rules of complementary base pairing (see, for example, Watson, J. D. et al., In: Molecular Biology of the Gene, 4th Ed., W. A. Benjamin, Inc., Menlo Park, Calif. (1987)). Typically, vector mediated methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., Molecular Cloning (A Laboratory Manual), Cold Spring Harbor Laboratory, 1982.

A number of template dependent processes are available to amplify the target sequences of interest present in a sample. One of the best known amplification methods is the polymerase chain reaction (PCR) which is described in detail in U.S. Pat. Nos. 4,683,195, 4,683,202 and 4,800,159, and in Innis et al., *PCR Protocols*, Academic Press, Inc., San Diego Calif., 1990, each of which is incorporated herein by reference in its entirety. Briefly, in PCR, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR amplification procedure may be performed in order to quantify the amount of mRNA amplified. Polymerase chain reaction methodologies are well known in the art.

Another method for amplification is the ligase chain reaction (referred to as LCR), disclosed in EPA No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Application No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[ alpha-thio]triphosphates in one strand of a restriction site (Walker, G. T., et al., *Proc. Natl. Acad, Sci. (U.S.A.)* 1992, 89:392–396, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and which involves annealing several probes throughout a region targeted for amplification, followed by a repair reaction in which only two of the four bases are present. The other two bases can be added as biotinylated derivatives for easy detection. A similar approach is used in SDA.

Sulfonylurea receptor specific nucleic acids can also be detected using a cyclic probe reaction (CPR). In CPR, a probe having a 3' and 5' sequences of non-sulfonylurea receptor specific DNA and middle sequence of sulfonylurea receptor specific RNA is hybridized to DNA which is present in a sample. Upon hybridization, the reaction is treated with RNaseH, and the products of the probe identified as distinctive products, generate a signal which is released after digestion. The original template is annealed to another cycling probe and the reaction is repeated. Thus, CPR involves amplifying a signal generated by hybridization of a probe to a sulfonylurea receptor specific expressed nucleic acid.

Still other amplification methods described in GB Application No. 2 202 328, and in PCT Application No. PCT/US89/01025, each of which is incorporated by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS) (Kwoh D., et al., *Proc. Natl. Acad. Sci. (U.S.A.)* 1989, 86:1173, Gingeras T. R., et al., PCT Application WO 88/10315, each of which is incorporated herein by reference in its entirety), including nucleic acid sequence based amplification (NASBA™) and 3SR. In NASBA™, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has sulfonylurea receptor specific sequences. Following polymerization, DNA/RNA hybrids are digested with RNase H while double stranded DNA molecules are heat denatured again. In either case the single stranded DNA is made fully double stranded by addition of second sulfonylurea receptor specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate sulfonylurea receptor specific sequences.

Davey, C., et al., European Patent Application Publication No. 329,822, incorporated herein by reference in its entirety, disclose a nucleic acid amplification process involving cyclically synthesizing single-stranded RNA ("ssRNA"), ssDNA, and double-stranded DNA ("dsDNA") which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller, H. I., et al., PCT application WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "race" disclosed by Frohman, M. A., In: *PCR Protocols: A Guide to Methods and Applications* 1990, Academic Press, N. Y.) and "one-sided PCR" (Ohara, O., et al., Proc. Natl. Acad. Sci. (U.S.A.) 1989, 86:5673–5677), all references herein incorporated by reference in their entirety.

Methods based on ligation of two (or more) oligonucleotides in the presence of nucleic acid having the sequence of the resulting "di-oligonucleotide", thereby amplifying the di-oligonucleotide (Wu, D. Y. et al., *Genomics* 1989, 4:560, incorporated herein by reference in its entirety), may also be used in the amplification step of the present invention.

Test fragment and control fragment may be amplified by any amplification methods known to those of skill in the art, including and not limited to the amplification methods set forth above. For purposes of the present invention, amplification of sequences encoding patient and wild type sulfonylurea receptor includes amplification of a portion of a sequence such as and not limited to a portion of the sulfonylurea receptor sequence of SEQ ID NO: 1, such as sequence of a length of about 10 nucleotides to about 1,000 nucleotides, more preferably about 10 nucleotides to about 100 nucleotides, or having at least 10 nucleotides occurring anywhere within the SEQ ID NO: 1, where sequence differences are known to occur within sulfonylurea receptor test fragments. Thus, for example, a portion of the sequence encoding the second nucleotide binding fragment (NBF-2) region of sulfonylurea receptor of a patient sample and a control sample may be amplified to detect sequence differences between these two sequences.

Following amplification of the test fragment and control fragment, comparison between the amplification products of the test fragment and control fragment is carried out. Sequence differences such as and not limited to nucleic acid transition and restriction digest pattern alterations may be detected by comparison of the test fragment with the control fragment. Nucleic acid transition includes and is not limited to a G to A transition at nucleic acid position 750 of SEQ ID NO: 1. Another nucleic acid transition involves a G to A transition at nucleic acid position 27 of SEQ ID NO: 31.

These nucleic acid transitions lead to restriction fragment length polymorphisms as exemplified by the altered results following MspI and NciI restriction digests set forth above. Accordingly, the restriction fragment length polymorphisms of test fragments may be compared to the restriction fragments of control fragments.

Alternatively, the presence or absence of the amplification product may be detected. The nucleic acids are fragmented into varying sizes of discrete fragments. For example, DNA fragments may be separated according to molecular weight by methods such as and not limited to electrophoresis through an agarose gel matrix. The gels are then analyzed by Southern hybridization. Briefly, DNA in the gel is transferred to a hybridization substrate or matrix such as and not limited to a nitrocellulose sheet and a nylon membrane. A labelled probe encoding a sulfonylurea mutation is applied to the matrix under selected hybridization conditions so as to hybridize with complementary DNA localized on the matrix. The probe may be of a length capable of forming a stable duplex. The probe may have a size range of about 200 to about 10,000 nucleotides in length, preferably about 500 nucleotides in length, and more preferably about 2,454 nucleotides in length. The preferred sequence of the probe is set forth in SEQ ID NO: 32. Mismatches which permit substantial similarity to SEQ ID NO: 30, such as and not limited to sequences with similar hydrophobicity and hydrophilicity, will be known to those of skill in the art once armed with the present disclosure. Various labels for visualization or detection are known to those of skill in the art, such as and not limited to fluorescent staining, ethidium bromide staining for example, avidin/biotin, radioactive labeling such as $^{32}P$ labeling, and the like. Preferably, the product, such as the PCR product, may be run on an agarose gel and visualized using a stain such as ethidium bromide. See Sambrook et al., supra. The matrix may then be analyzed by autoradiography to locate particular fragments which hybridize to the probe. Yet another alternative is the sequencing of the test fragment and the control fragment to identify sequence differences. Methods of nucleic acid sequencing are known to those of skill in the art, including and not limited to the methods of Maxam and Gilbert, *Proc. Natl. Acad. Sci., USA* 1977, 74, 560–564 and Sanger, Proc. Natl. Acad. Sci., USA 1977, 74, 5463–5467.

A diagnostic kit for detecting PHHI comprising in one or more containers at least one primer which is complementary to a sulfonylurea receptor sequence and a means for visualizing amplified DNA is also within the scope of the present invention. Alternatively, the kit may comprise two primers. In either case, the primers may be selected from the group consisting of SEQ ID NOS: 12–20, for example. The diagnostic kit may comprise a pair of primers wherein one primer within said pair is complementary to a region of the sulfonylurea receptor gene, wherein one of said pair of primers is selected from the group consisting of SEQ ID NO: 12–20, a probe specific to the amplified product, and a means for visualizing amplified DNA, and optionally including one or more size markers, and positive and negative controls. The diagnostic kit of the present invention may comprise one or more of a fluorescent dye such as ethidium bromide stain, $^{32}P$, and biotin, as a means for visualizing or detecting amplified DNA. Optionally the kit may include one or more size markers, positive and negative controls, restriction enzymes such as and not limited to MspI and/or NciI, and/or a probe specific to the amplified product.

The following examples are illustrative but are not meant to be limiting of the invention.

EXAMPLES

Purification and Partial Characterization of the 140 kDa Receptor

HIT cell membranes were photolabeled using a radioiodinated derivative of the second generation hypoglycemic drug, glyburide, according to the methods of Nelson, D. A., et al., *JBC,* 1992, 267:14928, Aguilar-Bryan, L., et al., *JBC,* 1992, 267:14934, and Aguilar-Bryan, L., et al., *JBC,* 1990, 265:8218, the disclosures of which are hereby incorporated by reference in its entirety.

Glyburide (Kramer et al. *FEBS Lett.* 1988 229:355–359) and an iodinated derivative of glyburide (Aguilar-Bryan et al. *J. Biol. Chem.* 1990 265:8218–8224) are known to photolabel a 140 kDa polypeptide. The pharmacological characteristics of the photolabeling, a kD in the low nanomolar range, and appropriate rank order of displacement with other insulin-releasing sulfonylureas, are those expected from studies on glyburide-induced insulin release from islets (Panten et al. *Biochem. Pharm.* 1989 38:1217–1229) and β-cell lines (Schmid-Antomarchi et al. *J. Biol. Chem.* 1987 262:15840–15844) and inhibition of $K_{ATP}$ channel activity. Glyburide was purchased from Sigma (St. Louis, Mo.) and prepared in stock solutions of 10 mM in dimethyl sulfoxide. Radioligand stocks were prepared by diluting high pressure liquid chromatography-purified 5-[$^{125}$I]iodo-2-hydroxyglyburide in dimethyl sulfoxide. Specific activity (cpm/mol) was measured on radioligand diluted 1/1000 into 10 mM Tris, 100 mM NaCl, 2 mM EDTA, pH 7.4, and the absorbance determined at 2.5 nm intervals in a UV-VIS Gilford spectrophotometer. Dimethylsulfoxide was diluted 1/1000 into the same buffer, and the absorbance of the buffer without drug was subtracted at each wavelength to generate the final absorbance profile.

HIT cells, passage 67–73, were seeded in roller bottles at $50 \times 10^6$ cells/bottle in 100 ml of Dulbecco's modified Eagle's medium plus 10% fetal bovine serum. Cells were fed with 200 ml of medium plus serum 4–5 times over a period of 2 weeks until the cells were confluent. After plating and each feeding, bottles were gassed with 5% $CO_2$ prior to capping.

The cells in confluent roller bottles were washed with phosphate-buffered saline (0.14M NaCl, 3 mM KCl, 2 mM $KH_2PO_4$, 1 mM $Na_2HPO_4$, pH 6.8) and then incubated at room temperature with 25 ml of phosphate-buffered saline plus 2 mM EDTA until cells detached from the sides of the bottles. Cells were pelleted at 900×g for 10 minutes at 4° C.

All steps were carried out at 0°–4° C. Cell pellets were resuspended in 5 mM Tris, 2 mM EDTA, 0.1 mM PMSF, pH 7.4, using approximately 5 ml of buffer for each roller bottle. Cells were placed on ice for 40 minutes to allow swelling and then homogenized with 10 strokes of a motorized glass-TEFLON® homogenizer (500 rpm). The homogenate was centrifuged at 1000×g for 10 minutes to remove nuclei and cellular debris, and the supernatant transferred to 30 ml Beckman polycarbonate, screw-cap ultracentrifuge tubes. Supernatants were centrifuged at 100,000×g for 60 minutes in a Beckman 60 Ti rotor. The pellets were resuspended in membrane storage buffer (10 mM Tris, 100 mM NaCl, 2 mM EDTA, 20% glycerol, 0.1 mM PMSF, pH 7.4). 200 mg of membrane protein were typically obtained from 20 roller bottles.

Membranes were stored at −80° C. at 5 mg/ml protein in 10 mM Tris (pH 7.5), 0.1M NaCl, 2 mM EDTA, 20% glycerol. To monitor receptor purification, an aliquot (5–20 ml) of the membranes was incubated with 1 nM [$^{125}$I]-iodo-2-hydroxyglyburide for 15 minutes and the sample photolabeled. Binding of 5-[$^{125}$I]-iodo-2-hydroxyglyburide (5–10 nM) to membranes was done for 30 minutes at 23° C. Aliquots were pipetted onto parafilm and irradiated at 23° C. in a UV crosslinker (Fisher Scientific). The energy settings for the UV cross-linker were factory calibrated at 254 nm. For crosslinking at 312 nm, a conversion factor was estimated by determining the time required for the UV cross-linker to deliver a specific amount of energy with each set of bulbs, and then multiplying by the ratio of these times.

All subsequent steps were performed at room temperature in the presence of 0.1 mM PMSF, 0.1 mM phenanthroline and 0.1 mM iodoacetamide. 20% (w/v) digitonin was freshly prepared by boiling in deionized water, then added to 200–400 mg thawed labeled membranes to a final concentration of 1%. Membranes were solubilized for 15 minutes then sedimented for 1 hr at 100,000×g. The supernatant was divided into 4 ml aliquots and each aliquot was chromatographed over a 1 ml Concanavalin A-Sepharose column equilibrated with 25 mM Tris-HCl, pH 7.5,0.1M NaCl, 2 mM EDTA, 1% digitonin. The solution was cycled through the column twice before washing the column with 8 ml of the equilibration buffer. Retained protein was eluted with 4 ml of the same buffer containing 0.5M methyl α-D-mannopyranoside. The eluted protein was stored at −80° C. Three Con A eluates were combined, then cycled twice over a 1 ml column of reactive green 19-agarose equilibrated with 50 mM HEPES (pH 8.5), 2 mM EDTA, 0.2% digitonin. The column was washed with 8 ml of the equilibration buffer followed by 8 ml of the same buffer containing 0.4M NaCl. The retained protein was eluted with 4 ml of the equilibration buffer containing 1.5M NaCl. The two pooled eluates were diluted 1:1 with the HEPES equilibration buffer without NaCl and cycled twice over a 1 ml phenylboronate-10 agarose column. The column was washed with 8 ml of the HEPES buffer, followed by 2 ml of 0.1M Tris-HCl, pH 7.5, 2 mM EDTA, 0.1% digitonin. Protein was eluted with 4 ml of 0.1M Tris (pH 7.5), 2 mM EDTA, 0.1% SDS. The protein was concentrated to 0.5 ml using a 100,000 MW cutoff Amicon filter, pretreated with 5% TWEEN-20®, then loaded onto a single 5 cm wide lane of a 5.5% polyacrylamide SDS gel. After electrophoresis the gel was stained with COOMASSIE™ blue, destained, and the receptor band excised with a razor blade. The receptor was electroeluted into a 14,000 MW cutoff dialysis bag and concentrated by Amicon filtration.

Table 1 summarizes the yields and fold-purification in the scheme developed for receptor purification. The amount of receptor, yields, and fold-purification reported after each step are based on the radioactivity, determined by γ counting, in the 140 kDa band after electrophoresis relative to the total protein loaded on a gel lane (as determined using the BioRad protein assay). HIT cell membranes contain approximately 1.6 pmol of receptor per mg of membrane protein as determined by filtration binding (Aguilar-Bryan et al. *J. Biol. Chem.* 1990 265:8218–8224).

TABLE 1

Purification of the High Affinity 140 kDa Sulfonylurea Receptor from HIT cells

| Step | Total Volume ml | Total Protein mg | Receptor pmol | Receptor pmol/mg | Purification~ fold | Yield % |
|---|---|---|---|---|---|---|
| Crude Membranes | 90 | 200 | 320 | 1.6 | 1 | 100 |
| Supernatant | 90 | 150 | 240 | 1.6 | 1 | 75 |
| ConA-Sepharose | 48 | 10.2 | 80 | 7.8 | 4.9 | 25 |
| Reactive Green 19-agarose | 16 | 1.8 | 56 | 31.1 | 19.5 | 18 |
| Phenyl boronate agarose | 4 | 0.56 | 45 | 80.4 | 50.4 | 14 |
| SDS-PAGE electroelute | 0.2 | ~0.002 | 8 | 4000 | 2507 | 2.5 |

Figure 1A:
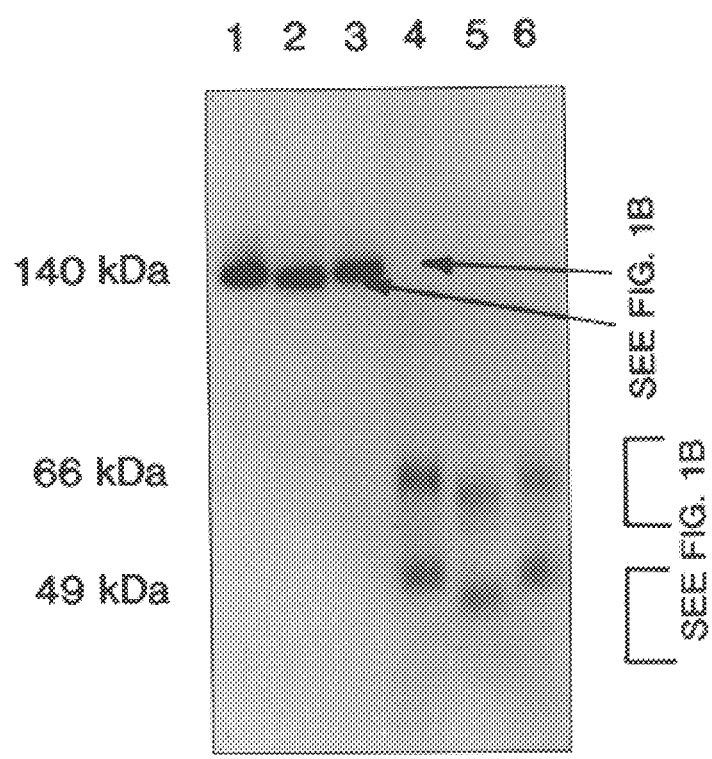

For the autoradiogram depicted in FIG. 1A, 1–2 μg of purified, radiolabeled receptor was made 1% in β-octylglucoside and divided into 6 aliquots. Lane 1 contained receptor kept on ice. The receptor was incubated in the presence (lane 2) and absence (lane 3) of Endo F for 30 min at 37° C. Aliquots of the samples for lanes 1–3 were further incubated with V8 protease (1 μg/10 μl) for 30 min at 37° C., yielding two radiolabeled peptides of 66 and 49 kDa (lanes 4 and 6), both of which are N-glycosylated as indicated by the mobility shift after endo F treatment (lane 5). To obtain Nterminal sequence from the intact receptor, 2 μg of protein was separated by electrophoresis on a single, 0.8 cm wide lane of a 5.5% gel. The receptor was transferred to ProBlot (Applied Biosystems) in 10 mM CAPS (pH 11), 10% MeOH, the filter stained for 10–20 seconds with COOMASSIE™ blue, destained, the band excised and microsequenced. To prepare receptor fragments for microsequencing, 10 μg of purified receptor was cleaved with V8, electrophoresed on a single lane and the fragments from the partial digest transferred to ProBlot. Fragments were prepared and sequenced multiple times as indicated in the figure. Gels used in the preparation of receptor and fragments for microsequencing were aged overnight, and the top tray buffer contained 0.1 mM thioglycolate.

The purified receptor showed a small apparent molecular weight decrease ($\Delta M_r$~3000) following treatment with Endoglycosidase F/N-glycosidase F (Endo F) and yielded two bands following limited cleavage with V8 protease (FIGS. 1A and 1B). Each of the major labeled proteolytic fragments, $M_r$~69 and 49 kDa, shift mobility after digestion with Endo F. Identical N-terminal sequence, 15–25 residues, were recovered from each of the major labeled peptides. No residue was obtained at residue 9 when the glycosylated peptides were sequenced; an aspartic acid was identified at residue 9 in the deglycosylated receptor indicating this is an N-glycosylated asparagine. In addition, N-terminal sequences were recovered on two unlabeled V8 peptides and a third minor labeled peptide. The results indicate there is an N-linked glycosyl group at residue nine in the mature receptor, suggesting that the N terminus is extracellular, and that the sulfonylurea labeling site is within the first 50 kDa of the receptor.

Two multiple antipeptide antibodies (MAPs), directed against residues 1 through 8 and 10 through 20 both immunoprecipitate photolabeled 140 kDa receptors from HIT, mouse αTC-6, and rat insulinoma (RIN) cells. MAPs were prepared by synthetic protein sequencing (Perkin Elmer-ABI, 430 A Peptide Synthesizer, Foster City, Calif.) to obtain antibodies to M-P-L-A-F-C-G-T, SEQ ID NO: 10, residues 1–8 of SEQ ID NOS: 28 and 29. This process was repeated for residues 10–20 of SEQ ID NOS: 28 and 29, N-H-S-A-A-Y-R-V-D-Q-G, SEQ ID NO: 11. A purified sulfonylurea receptor protein was immunoprecipitated from HIT cells using the MAPs prepared as set forth above.

HIT cell membranes were incubated with 5-[$^{125}$I]iodo-2-hydroxyglyburide, photolabeled, solubilized with 1% digitonin, centrifuged at 100,000×g and the supernatant incubated with $^{1}\!/_{10}$ volume of preimmune serum, immune serum, immune serum+anti-MAP 10–20, or immune serum+ irrelevant MAP peptide. 50 μl of protein A-Sepharose was added and the mixture was incubated for 2 hours at room temperature, the beads washed with buffer, heated in the presence of pH 9 sample buffer, eletrophoresed on a 6% polyacrylamide SDS gel, and an autoradiogram prepared.

Figure 2A:
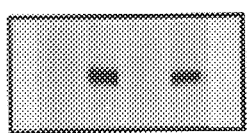
FIG. 2A shows that antibodies against residues 10–20 specifically recognize the 140 kDa polypeptide. Purified 140 kDa polypeptide was electrophoresed on a single lane of a 6% SDS gel and transferred to Immobilon P. The Immobilon P was placed in a miniblotter and the lanes incubated as follows: Lane 1—Preimmune serum. Lane 2—Immune serum. Lane 3—Immune serum+immunogen. Lane 4 immune serum+irrelevant MAP peptide. The filter was further incubated with a second antibody (goat anti-rabbit conjugated to alkaline phosphatase) and developed with the appropriate substrates.
Figure 2B:
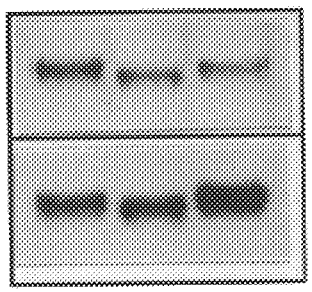
FIG. 2B displays antibodies which recognize a polypeptide with the appropriate mobility shift following Endo F treatment. Purified receptor (lane 1) was incubated for 30 min at 37° C. in the presence (lane 2), or absence (lane 3) of endoglycosidase F/N-glycosidase F, incubated with first (anti-MAP 10–20) and second antibody, and developed with substrate. The bottom panel shows the autoradiogram of the immunoblot in the top panel.
Figure 2C:
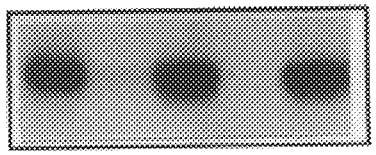
FIG. 2C shows antibodies which immunoprecipitate the photolabeled 140 kDa receptor. HIT cell membranes were incubated with $^{125}$I-labeled iodoglyburide, photolabeled, solubilized with 1% digitonin, centrifuged at 100,000×g and the supernatant (lane 1) incubated with preimmune serum (lane 2), immune serum (lane 3), immune serum+anti-MAP 10–20 (lane 4) and immune serum+irrelevant MAP peptide (lane 5). Samples were co-incubated with protein A-SEPHAROSE® beaded form of agarose polysaccharides, the beads washed with buffer, heated in the presence of pH 9 sample buffer, electrophoresed on a 6% polyacrylamide SDS gel, and an autoradiogram prepared. Results using antibodies against receptor residues 1–8 were the same as those using antibodies against residues 10–20.

The immunoprecipitation was competed using the immunizing peptide, but not the other MAPS (FIGS. 2A–C). The amino acid sequence is derived from the photolabeled protein and the N-terminal amino acid sequence is conserved between mouse, rat, and hamster.

Isolation and Characterization of CDNA Clones

Degenerate PCR primers with flanking restriction sites were designed based on the sequence obtained from the labeled peptides. The primers used were as follows:
 primer 1 (SEQ ID NO: 23): 5' GAGAGAAGCTT(T/C) TG(T/C)GG(T/C/G/A)GA(A/G)AA(T/C)CA-3'
 primer 2 (SEQ ID NO: 24): 5' GAGAGAGAATTCC(T/ C)TG(A/G)TC(T/C/G/A)AC(T/C/G/A)C(G/T)(A/G) TA-3'

The bases in parenthesis indicate the degeneracy at that position. The sequence in bold was derived from the peptide sequence obtained from the N-terminus of the sulfonylurea receptor. The remaining 5' sequence was added to facilitate subcloning. Primer 1 has a HindIII site at the 5' end; Primer 2 was engineered with an EcoRI site at the 5' end. These primers were used in a standard PCR reaction with a random primed cDNA library, constructed in XZAPII using mouse α-cell poly A+ mRNA, as template. The following cycle times and temperatures were employed: 94° C. for 10 minutes; 85° C. for 3 minutes, [50° C. for 2 minutes, 72° C. for 5 minutes, 94° C. for 2 minutes,] 50° C. for 2 minutes, 72° C. for 5 minutes.

The bracketed conditions were cycled 30 times. From the N-terminal peptide sequence of the receptor a 47 base pair coding region was expected to be amplified plus the 20 base pairs added to the primers to facilitate cloning yielding an expected 67 base pair product. The 47 base pair coding region was predicted to have 14 base pairs that were not present in the primers. The PCR product obtained was approximately 67 base pairs and was restricted with EcoRI and HindIII, subcloned into M13 and sequenced. The resulting sequence gave the expected 14 base pairs indicating the sequence was derived from the receptor. The 47 base pair oligonucleotide given below was synthesized based on the consensus sequence derived from nine M13 clones: 5' TTTTGCGGGACGGAGAATCACTCGGCCGCCTACCG CGTCGACCAAGG-3' (SEQ ID NO: 25). This oligonucleotide was used to screen the random primed mouse αTC-cell cDNA library.

A 1.1 kb cDNA was cloned which encoded 28 amino acids obtained from peptide sequencing. This cDNA fragment was used to screen RIN and HIT cell cDNA λ libraries to obtain full sequence.

The nucleotide sequence of a 4635 bp rat receptor cDNA inclulded an open reading frame that encodes a 1498 amino acid protein with a mass of 167,834 daltons, larger that predicted by SDS polyacrylamide gel electrophoresis. Aguilar-Bryan, L., et al., *JBC*, 1990, 265:8218. There is a single insertion of an asparagine at position 742 and a deletion of a threonine at position 831. The first difference between the hamster and rat sequences is in the same relative position, 21 residues C-terminal of the Walker consensus site, as the ΔF508 deletion seen in a common cystic fibrosis transconductance regulator (CFTR) mutation (Riordan et al. *Science* 1989 245:1066–1073). In addition to the insertion and deletion, the first nucleotide binding fold contains approximately a third ($^{10}\!/_{33}$) of all differences between the two species.

The mature rat protein, defined by peptide sequencing, begins with a proline following the methionine start site. In the RIN cell receptors the adjacent amino acid is a methionine. This is the initiating methionine based on the surrounding sequence which is a good fit to the consensus pattern for initiation, GCC(A/G)CCAUG(G) (SEQ ID NO: 26) (Kozak, M. *Cell* 1986 44:283), including the strongly conserved A at position −3. However, in the mouse receptor, an additional 35 amino acids is found preceding this proline which cannot eliminate the possibility that some forms of the hamster and rat receptors have similar leader sequences. Confirming the chemical sequence, residue 9 in the mature proteins is an asparagine within a consensus glycosylation site.

A Blast search of the National Center for Biotechnology Information (NCBI) nucleotide database with the receptor sequence produced matches with several members of the P-glycoprotein/multidrug resistance protein family. A similar search with the amino acid sequence indicated the sulfonylurea receptor is a member of the ATP-binding cassette superfamily with two putative nucleotide binding domains. The sulfonylurea receptor sequence revealed 29% similarity, to an ATP-binding cassette superfamily member, termed a multidrug resistance-associated protein (MRP), isolated from a small cell lung carcinoma cell line (H69AR) selected with doxorubicin (Cole et al. *Science* 1992 258:1650–1654). A cluster analysis of this molecule, dvhuar in the Protein Identification Resource (PIR) database, indicates it is related to the leishmania P-glycoprotein-related molecule (Lei/PgpA), the CFTRs (human (Hum/CFTR), bovine (Bov/CFTR), mouse (Mus/CFTR), and dogfish (Squ/ CFTR)) (Cole et al. *Science* 1992 258:1650–1654). A similar result was obtained for the sulfonylurea receptor with the additional inclusion of the Xenopus CFTR indicating the receptor is a member of this cluster.

The identification of the nucleotide binding domains goes beyond simply having Walker "A" and "B" consensus sequences. The receptor is similar to the 230–240 amino acid nucleotide binding domain(s) described by (Hyde et al.

Nature 1990 346:362–365) and database searches find similarities to the nucleotide binding fold of ATP-binding proteins. The more conserved of the two receptor nucleotide binding folds, based on similarity with other ATP-binding proteins and the comparison of the rat and hamster sequences, is at the C-terminal end.

RNA Analysis

Northern blot analysis of poly A+ mRNA isolated from RIN, HIT and αTC-6 cells, previously shown to have the high affinity receptor by drug binding and photolabeling studies (Aguilar-Bryan et al *J. Cell. Biochem. Suppl.* 1994 18A:133) each have an approximately 5000 nucleotide transcript, see FIG. 3. A preliminary tissue distribution study shows the same size transcript is present in mouse brain and heart.

Predicted Protein Structure

Sequence similarities indicate the sulfonylurea receptor has two potential ATP binding folds. The size and additional sequence similarities with P-glycoproteins and CFTRs suggest the receptor has a similar structure. Hydrophobicity (FIG. 4) and hydrophobicity versus hydrophobic moment (Eisenberg et al. *J. Mol. Biol.* 1984 179:125) plots were used to generate a model for the receptor (FIG. 5). Two constraints were imposed on the model structure: the glycosylation site is on the external face of the membrane and both nucleotide binding domains are on the internal face. The 'classical' ATP-binding cassette superfamily model proposes duplication of a unit consisting of six transmembrane spanning helices followed by a nucleotide binding domain. The sulfonylurea receptor differs from this model and has at least nine potential transmembrane helices before the first nucleotide binding domain but only four between the two nucleotide binding domains (FIG. 5). The multidrug resistance-associated protein (MRP) is predicted to have 8 transmembrane spanning helices (Cole et al. *Science* 1992 258:1650–1654).

Phosphorylation has been implicated in regulation of $K_{ATP}$ channel activity (Schwanstecher et al. *J. Pharmacol. Exper. Ther.* 1992 262:495–502) and has been proposed to change the affinity of the sulfonylurea receptor for various ligands. There are 21 potential phosphorylation sites in the receptor sequence; 3 protein Kinase A (pKA) sites and 18 protein kinase C (pKC) sites. The pKA site at 278 is predicted to be on the external face of the membrane, while those at positions 1363 and 1417 are in the second nucleotide binding fold. Four of the pKC sites (positions 151, 200, 304 and 1213) are predicted to be extracellular or in a membrane spanning helix. Seven of the remaining 14 are in the nucleotide binding folds (NBF); 4 in NBF-1, and 3 in NBF-2. One of the latter sites, Thr 1297 in the Walker A consensus site, is expected to alter nucleotide binding if it is accessible for phosphorylation.

Functional Properties, In Vitro Translations mRNA, transcribed by SP6 RNA polymerase from the rat cDNA subcloned into pGEM4, was translated in vitro. Approximately 0.5 μg of mRNA was heated to 70° C. for 10 minutes, immediately cooled on ice then added to rabbit reticulocyte lysate (Promega, Madison, Wis.) supplemented with ribonuclease inhibitor, an amino acid mixture, and [$^{35}$S]methionine. The reaction mixture was incubated at 30° C. for 60 minutes then aliquots were subject to electrophoresis on SDS polyacrylamide gels using standard protocols. The gels were dried and autoradiographed.

The resulting protein was approximately 137 kDa, indicating the receptor behaves anonymously on SDS polyacrylamide gels having a faster than expected mobility, see FIG. 6A. A similar anomalous behavior has been reported for CFTRs (Gregory et al. *Nature* 1990 347:382–386).

Anti-Nucleotide Fold Antibodies Immunoprecipitate the Photolabeled 140 kDa Receptor Antibodies were produced against two fusion proteins containing the two nucleotide binding folds. Fragments of the receptor cDNA were subcloned in frame into pMALc (New England BioLabs, Boston, Mass.) at the C-terminal end of the DNA encoding the maltose binding protein (MBP). A plasmid expressing the first nucleotide binding fold fused to MBP was constructed by restricting pMALc with StuI and SalI and restricting the sulfonylurea receptor cDNA with PvuII plus XhoI. A unique 500 base pair fragment was gel purified from the receptor cDNA digest and subcloned into pMALc. The construction was verified by sequencing. The receptor segment expressed is leu708 to leu874. Expression was obtained in *E. coli* following transformation and induction by isopropylthiogalactoside per the manufacturer's directions. The expressed proteins were found to be in inclusion bodies which were solubilized in SDS and separated on SDS polyacrylamide gels, see FIG. 6B. The fusion protein was electroeluted, concentrated, and used as an immunogen. The solubilized protein in 200 μg amounts, with complete, or incomplete Freund's adjuvant, was injected interdermally into rabbits using a standard 2–3 week regimen of bleeding and boosting.

Injection of Xenopus Oocytes with Receptor mRNA mRNA, approximately 50 ng, transcribed as described above, was injected into Xenopus oocytes. The injected oocytes were assayed for K+ channel activity after 1–5 days using both two-electrode and patch clamp methods. New K+ currents in the injected oocytes were not detected. Similarly, co-injection of mRNAs transcribed from cDNAs encoding two small inward rectifiers, ROMK1 (Ho et al. *Nature* 1993 362:31–38) or a brain homolog of IRK1 (Kelly et al. *Biophysical J.* 1994 66(2):A109) failed to confer sulfonylurea sensitivity on these K+ channels. The results suggest that the 140 kDa receptor does not have intrinsic K+ channel activity, or that Xenopus oocytes are not an adequate background for their expression.

Transfection Experiments

The sulfonylurea receptor cDNA has been ligated into eukaryotic expression vectors containing SV40 virus, adenovirus and cytomegalovirus (CMV) promoters. These plasmids have been transfected into COS cells which do not have the high affinity sulfonylurea receptor as determined by filtration binding and photolabeling studies. To date experiments with the SV40 plasmid have shown that the transfected cells produce an mRNA of the appropriate size as determined by Northern blots with receptor cDNA. Metabolic labeling experiments with the SV40 plasmid where transfected and non-transfected cells were labeled with [$^{35}$] methionine indicate that the transfected, but not the non-transfected cells, synthesize an appropriate sized protein which can be immunoprecipitated with the antinucleotide binding fold antibodies. The level of receptor synthesized by COS cells using this promoter has been low using SEQ ID NOS: 27 and 28. Expression levels are high using SEQ ID NOS: 4, 5, 7, and 8 from rat and hamster.

Chromosomal localization of the Sulfonylurea Receptor Gene

Chromosomal localization of the Sulfonylurea Receptor (SUR) gene to normal male human banded chromosomes was determined by utilization of the fluorescence in situ hybridization (FISH) technique by staining with 4,6-diamidino-2-phenylindole (DAPI). A metaphase spread showed the two chromosome 11 homologues which map the SUR cDNA to 11p15.1. Overlapping human SUR cDNA plasmids "mid" and "3", totaling 3.8 kb, were labeled with biotin-14-dATP (GIBCO) and hybridized in situ to standard metaphase spreads from normal male peripheral blood lymphocytes, according to the methods of P. Lichter et al., Science 247, 64 (1990), the disclosure of which is hereby incorporated by reference in its entirety. The biotin-labeled DNA was detected using Fluorescein-Avidin DCS (Vector Laboratories, Burlingame, Calif.). Chromosomes were identified by simultaneous DAPI staining, which produces a Q-banding pattern. Fifteen metaphases were analyzed. Digital images were obtained with a cooled charge-coupled device camera mounted on a standard epifluorescent microscope (Axioplan; Zeiss, Thronwood, N.Y.). Images were acquired using the software ISee (Inovision Co.) running on a Sun workstation. Fluorescein isothiocyanate and DAPI fluorescence were recorded separately as gray scale images and then merged using the software package NIH 1.55 (J. W. Ijdo, E. A. Lindsay, R. A. Wells, A. Baldini, Genomics 14, 1019 (1992)). Eighty-five per cent of metaphases analyzed showed specific hybridization signal on both chromatids of the two chromosomes 11 at 11p15.1.

Partial cDNA clones, comprising 3.8 kb of coding sequence of the human homologue of SUR, were obtained from a human pancreatic cDNA library (provided by Graeme Bell, University of Chicago, and commercial libraries of Clontech, Palo Alto, Calif. and Invitrogen, San Diego, Calif.). The library was produced in lambda gt10 phage (Bell RIN library) and screened with a 2294 bp hamster cDNA probe encoded by SEQ ID NO: 30.

The protocol for making the library is provided by Sambrook et al., supra. Poly A+ mRNA was isolated using an oligo dT column. Poly A+ mRNA was incubated with oligo dT and random hexamers plus reverse transcriptase (such as MMLV RT from Promega, Stratagene or NEBL) and dNTPs to produce single strand cDNA. The single strand cDNA is treated with E. coli DNA polymerase, RNAseH and dNTPs, then ligated to linkers that have EcoRI sites to produce double stranded DNA. The final product is restricted with EcoRI and ligated, using T4 DNA ligase, into lambda phage DNA that has been similarly restricted and dephosphorylated with alkaline phosphatase to prevent self ligation. The ligated product is packaged into phage using commercially available packaging extracts.

Screening involved plating and hybridizing at 55° C. or 65° C. in 5× or 6×SSC (according to the methods of Sambrook, et al.). 55° C. was used for cross species screens and 65° C. was employed for the same species. Two washes were carried out at room temperature using 2×SSC, then one at the hybridization temperature of 65° C. using 0.1×SSC.

Hybridizations and washes were done at reduced stringency (55° C.) using methods according to F. M. Ausubel et al., Current Protocols in Molecular Biology (Greene Publishing Associates, Inc, New York, N.Y., 1989), Chap. 6, the disclosures of which are hereby incorporated by reference in their entirety. Subsequent screening was done at higher stringency (65° C.), using a human cDNA of SEQ ID NO: 31 obtained from the first screen as a probe.

Characterization of these cDNA clones by sequence analysis revealed an overall homology of 95% with the rat SUR gene. A specific hybridization signal was detected at the band 11p15.1 in 85% of metaphases on both chromatids of the two chromosomes 11.

Detection of Sulfonylurea Receptor Mutations in PHHI Affected Individuals

Mutational analysis was performed on samples from 16 affected progeny of nine consanguineous matings. In each case, diagnosis of PHHI was based on criteria established by A. Aynsley-Green et al., supra., the disclosure of which is hereby incorporated by reference in its entirety. The parents in six families were first cousins, in two families second cousins, and in one family more distantly related. Eight families were of Saudi Arabian origin, recruited from the patient population of the Arabian American Oil Company Hospital Medical Services Organization, after institutional approval was received, and one was of Germanic origin. Family labels follow the form of Thomas et al., supra.

Studies indicated that no major insertions or deletions of the SUR locus had occurred in three of the families. The first region evaluated, by direct sequence analysis, was the second nucleotide binding fold (NBF-2) of the human SUR homologue (FIG. 7). This is the most highly conserved region of the SUR gene, and in other superfamily members it, as well as NBF-1, has functional importance for control of channel activity through interaction with cytosolic nucleotides. S. C. Hyde, Nature 346, 362 (1990) and M. J. Weish, A. E. Smith, Cell 73, 1251 (1993).

To obtain this genomic structure, a normal human lymphocyte genomic bacteriophage library (provided by Mary Beth Humphrey, Baylor College of Medicine) was screened, using standard methods according to F. M. Ausubel et al., supra., with a human partial SUR cDNA probe of SEQ ID NO: 31 (cDNA probe, "3prime").

The human genomic library was made in lambda FIX using materials supplied by Stratagene, Inc. Briefly, genomic DNA was partially digested with Sau3A, the fragments were precipitated with ethanol, resuspended with precut lambda FIX DNA which has compatible ends, ligated with T4 DNA ligase and packaged and screened.

Hybridizations and washes were done at reduced stringency (55° C.) using methods according to F. M. Ausubel et al., Current Protocols in Molecular Biology (Greene Publishing Associates, Inc, New York, N.Y., 1989), Chap. 6, the disclosures of which are hereby incorporated by reference in their entirety. The library was screened with a 1.2 kb hamster cDNA probe of SEQ ID NO: 32, which spans the SUR NBF2 sequence. Subsequent screening was done at higher stringency (65° C.), using a human cDNA for example, using SEQ ID NO: 31 as a probe.

Screening involved plating and hybridizing at 55° C. or 65° C. in 5× or 6×SSC (according to the methods of Sambrook, et al.) . 55° C. was used for cross species screens and 65° C. was employed for the same species. Two washes were carried out at room temperature using 2×SSC, then one at the hybridization temperature of 65° C. using 0.1×SSC.

Inserts in the bacteriophage clone λG4 were subcloned into pBluescript 11 (Stratagene, La Jolla, Calif.). Plasmids were purified using standard cesium chloride purified methods, restricted using the appropriate desired enzyme(s). The fragments were purified by electrophoresis on low melt agarose and cut out of the gel. A 1-to-5 microliter aliquot of the desired fragment and 1 microgram of the appropriately restricted plasmid carrying a selectable ampicillin resistance marker (such as pBluescript from Stratagene, Inc.) were melted at 65° C., mixed and diluted to 20 microliters with a buffer containing T4 DNA ligase and ATP, then incubated for 4–18 hours before transforming into *E. coli* and selecting on ampicillin plates.

Exon-intron boundaries were defined by comparing the nucleotide sequences of the human SUR gene and cDNA, which were obtained using the dideoxy chain termination method (Sequenase; U.S. Biochemicals, Cleveland, Ohio).

Because of the consanguineous matings and autosomal recessive inheritance pattern of this disorder, affected individuals are expected to be homozygous by descent at the disease gene locus. E. S. Lander and D. Botstein, *Science* 236, 1567 (1987), the disclosure of which is hereby incorporated by reference in its entirety. Direct sequencing of a pancreatic cDNA product, isolated from an affected child of Family 6, revealed a 109 bp deletion within the NBF-2 region which corresponded to skipping of an exon resulting in a cDNA product of about 2190 bp in length using primers of SEQ ID NOS: 16 and 17 as compared to mRNA of about 2080 bp in length. The effects of this skipping event are severe and include production of a frameshift, premature truncation of the protein due to inclusion of a stop 24 codons later, and disruption of the NBF-2 (FIGS. 8A and 8B). The splice sites of the skipped exon were evaluated at the genomic DNA level and a homozygous G to A point mutation, located within the 5' splice site at the last base of the skipped exon, was found (FIG. 8C). A recognition site for the restriction endonuclease MspI is destroyed by this base change, providing a means to confirm and test for the presence of the mutation. mRNA was directly isolated using Oligotex (Qiagen Inc., Studio City, Calif.) from a fresh-frozen pancreatic tissue sample and reverse transcribed (RT), using random primers (Invitrogen, San Diego, California), with Superscript 11 (GIBCO-BRL) into cDNA. For cloning of the NBF-2 region, an initial PCR amplification with 19 (primer 22 (located 5' of 17)) and 15 (primer 29) was followed by a second amplification of a portion of the reaction with SEQ ID NOS: 13 (primer 17) and 15 (primer 29) using conditions described by P. M. Thomas, G. J. Cote, D. M. Hallman, P. M. Mathew, *Am. J. Hum. Genet.*, in press, supra.

PCR products were amplified using hybridization at 60° C. for 1 minute, elongated at 72° C. for 1 minute and denatured at 93° C. for 1 minute for thirty cycles. Hybridization may be carried out at temperatures of between about 55° C to about 65° C. The amplified product was cloned into pCR 11™ vector (Invitrogen, San Diego, Calif.) and sequenced, as above. pCR 11™ vector is set forth in FIG. 10. For detection of the mutation in genomic fragments, 100 ng of genomic DNA was amplified using SEQ ID NOS: 14 and 16, primers 28 and 29B, as above except in the presence of PCR buffer N (Invitrogen, San Diego, Calif.), and either directly PCR sequenced according to the methods of S. Khorana, R. F. Gagel, G. J. Cote, *Nucleic Acids Res.* 22, 3425 (1994), the disclosure of which is hereby incorporated herein by reference in its entirety, or cut with 5 U of MspI (GIBCO-BRL) at 37° C. for 2 hours and run on a 10% polyacrylamide gel. Visualization of products was by silver staining. Both affected children of Family 6 were homozygous, while the parents and two unaffected siblings were found to be heterozygous, for the mutation (FIG. 8D). Preliminary semiquantitative analysis revealed markedly decreased expression of the mutant SUR message upon comparison of patient and age-matched normal control pancreatic samples, suggesting instability of the mutant message.

Thirteen additional affected children, from six families of Saudi Arabian origin and one family of German origin, were found to be homozygous for this mutation, as demonstrated by loss of the MspI restriction enzyme recognition site. In all families, homozygous loss of the MspI site cosegregated with disease phenotype, and in Families 1–3 and 5 genotype analysis for this mutation agreed with previously reported haplotype data, P. M. Thomas, G. J. Cote, D. M. Hallman, P. M. Mathew, *Am. J. Hum. Genet.*, in press, supra. Direct sequencing of PCR-amplified genomic DNA from a representative affected member of each family determined that all exhibited the homozygous G to A mutation.

Family 4 demonstrated a unique mutation in the 3' splice site sequence preceding the start of the NBF-2 (FIG. 9A). This G to A mutation destroys an NciI restriction endonuclease site and homozygous loss of this site cosegregated with disease phenotype within the family. Again, genotype analysis of the members of this family supported previously reported haplotype data, P. M. Thomas, G. J. Cote, D. M. Hallman, P. M. Mathew, *Am. J. Hum. Genet.*, in press, supra.; both parents are heterozygotes for the mutation and the unaffected sibling is homozygous for the wild type allele (FIG. 9B). Since a pancreatic tissue sample from an affected individual in Family 4 was unavailable and we were unable to recover the SUR message from transformed lymphocytes, a chimeric construct was created to examine the effects of this mutation on the RNA splicing pathways according to the methods of R. Takahashi, et al., *Nature Genet.* 7, 79 (1994); I. Satokata, et al., *Proc, Natl. Acad. Sci.* 87 9908 (1990); H. Lou, G. J. Cote, R. F. Gagel, *Mol. Endo.* 8, 1618 (1994), the disclosure of each hereby incorporated by reference in its entirety.

Genomic DNA from affected and normal individuals was PCR-amplified using the SEQ ID NOS: 12 and 18 and cloned into pRSVhMT2A. Constructs were transfected into the human glioblastoma cell line SNB 19 using LIPOFECTAMINE™, transfection reagent, (Gibco-BRL, Gaithersburg, Md.). RT-PCR analysis was performed, with SEQ ID NOS:12 (primer 16) and 19 (primer DS8), as described by H. Lou, G. J. Cote, R. F. Gagel, *Mol. Endo.* 8, 1618 (1994), the disclosure of which is incorporated herein by reference in its entirety. The plasmids and their cDNA products were sequenced with SEQ ID NO: 17 (primer 34al). Genomic DNA fragments were PCR-amplified with SEQ ID NOS: 17 and 12 (primers 34al and 16) and digested with NciI, as in FIG. 8. With the construct containing the mutation, no wild type splicing pattern occurred. Instead, use of three cryptic 3' splice sites was demonstrated resulting in a 7 bp addition, a 20 bp deletion, and a 30 bp deletion in the exon (FIG. 9D). A similar intronic 3' splice acceptor mutation, described in the disorder 21-hydroxylase deficiency, also resulted in lack of the wild type splicing pattern, produced several cryptic splice products, and abolished normal protein activity. Y. Higashi, et al., *Proc. Natl. Acad. Sci., USA* 85, 7486 (1988), the disclosure of which is incorporated herein by reference in its entirety.

All PCR products prepared from genomic DNA of 100 normal, unrelated individuals showed normal MspI and NciI restriction patterns, indicating that neither mutation is a common polymorphism. The data presented provides evidence that mutations in the SUR gene cause familial persistent hyperinsulinemic hypoglycemia of infancy.

Various modifications of the invention in addition to those shown and described herein will be apparent to those skilled in the art from the foregoing description. Such modifications are also intended to fall within the scope of the appended claims.

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
( A ) LENGTH: 1308 base pairs
( B ) TYPE: nucleic acid
( C ) STRANDEDNESS: single
( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| GGACCTGCAG | CAGCTGGATG | ACACCACCCA | GCTTCCACTT | CTCTCACACT | TTGCCGAAAC | 60 |
| CGTAGAAGGA | CTCACCACCA | TCCGGGCCTT | CAGGTATGAG | GCCCGGTTCC | AGCAGAAGCT | 120 |
| TCTCGAATAC | ACAGACTCCA | ACAACATTGC | TTCCCTCTTC | CTCACAGCTG | CCAACAGATG | 180 |
| GCTGGAAGTC | CGAATGGAGT | ACATCGGTGC | ATGTGTGGTG | CTCATCGCAG | CGGTGACCTC | 240 |
| CATCTCCAAC | TCCCTGCACA | GGGAGCTCTC | TGCTGGCCTG | GTGGGCCTGG | GCCTTACCTA | 300 |
| CGCCCTAATG | GTCTCCAACT | ACCTCAACTG | GATGGTGAGG | AACCTGGCAG | ACATGGAGCT | 360 |
| CCAGCTGGGG | GCTGTGAAGC | GCATCCATGG | GCTCCTGAAA | ACCGAGGCAG | AGAGCTACGA | 420 |
| GGGACTCCTG | GCACCATCGC | TGATCCCAAA | GAACTGGCCA | GACCAAGGGA | AGATCCAGAT | 480 |
| CCAGAACCTG | AGCGTGCGCT | ACGACAGCTC | CCTGAAGCCG | GTGCTGAAGC | ACGTCAATGC | 540 |
| CCTCATCTCC | CCTGGACAGA | AGATCGGGAT | CTGCGGCCGC | ACCGGCAGTG | GGAAGTCCTC | 600 |
| CTTCTCTCTT | GCCTTCTTCC | GCATGGTGGA | CACGTTCGAA | GGGCACATCA | TCATTGATGG | 660 |
| CATTGACATC | GCCAAACTGC | CGCTGCACAC | CCTGCGCTCA | CGCCTCTCCA | TCATCCTGCA | 720 |
| GGACCCCGTC | CTCTTCAGCG | GCACCATCCG | ATTTAACCTG | GACCCTGAGA | GGAAGTGCTC | 780 |
| AGATAGCACA | CTGTGGGAGG | CCCTGGAAAT | CGCCCAGCTG | AAGCTGGTGG | TGAAGGCACT | 840 |
| GCCAGGAGGC | CTCGATGCCA | TCATCACAGA | AGGCGGGGAG | AATTTCAGCC | AGGGACAGAG | 900 |
| GCAGCTGTTC | TGCCTGGCCC | GGGCCTTCGT | GAGGAAGACC | AGCATCTTCA | TCATGGACGA | 960 |
| GGCCACGGCT | TCCATTGACA | TGGCCACGGA | AAACATCCTC | CAAAAGGTGG | TGATGACAGC | 1020 |
| CTTCGCAGAC | CGCACTGTGG | TCACCATCGC | GCATCGAGTG | CACACCATCC | TGAGTGCAGA | 1080 |
| CCTGGTGATC | GTCCTGAAGC | GGGGTGCCAT | CCTTGAGTTC | GATAAGCCAG | AGAAGCTGCT | 1140 |
| CAGCCGGAAG | GACAGCGTCT | TCGCCTCCTT | CGTCCGTGCA | GACAAGTGAC | CTGCCAGAGC | 1200 |
| CCAAGTGCCA | TCCCACATTC | GGACCCTGCC | CATACCCCTG | CCTGGGTTTT | CTAACTGTAA | 1260 |
| ATCACTTGTA | AATAAATAGA | TTTGATTATT | TCCTAAAAAA | AAAAAAAA | | 1308 |

( 2 ) INFORMATION FOR SEQ ID NO:2:

( i ) SEQUENCE CHARACTERISTICS:
( A ) LENGTH: 1308 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO (i v) ANTI-SENSE: NO (i x) FEATURE:
  (A) NAME/KEY: CDS
  (B) LOCATION: 2..1186

(x i) SEQUENCE DESCRIPTION: SEQ ID NO:2:

```
G GAC CTG CAG CAG CTG GAT GAC ACC ACC CAG CTT CCA CTT CTC TCA           46
  Asp Leu Gln Gln Leu Asp Asp Thr Thr Gln Leu Pro Leu Leu Ser
  1               5                   10                  15

CAC TTT GCC GAA ACC GTA GAA GGA CTC ACC ACC ATC CGG GCC TTC AGG          94
His Phe Ala Glu Thr Val Glu Gly Leu Thr Thr Ile Arg Ala Phe Arg
                    20                  25                  30

TAT GAG GCC CGG TTC CAG CAG AAG CTT CTC GAA TAC ACA GAC TCC AAC         142
Tyr Glu Ala Arg Phe Gln Gln Lys Leu Leu Glu Tyr Thr Asp Ser Asn
                35                  40                  45

AAC ATT GCT TCC CTC TTC CTC ACA GCT GCC AAC AGA TGG CTG GAA GTC         190
Asn Ile Ala Ser Leu Phe Leu Thr Ala Ala Asn Arg Trp Leu Glu Val
            50                  55                  60

CGA ATG GAG TAC ATC GGT GCA TGT GTG GTG CTC ATC GCA GCG GTG ACC         238
Arg Met Glu Tyr Ile Gly Ala Cys Val Val Leu Ile Ala Ala Val Thr
        65                  70                  75

TCC ATC TCC AAC TCC CTG CAC AGG GAG CTC TCT GCT GGC CTG GTG GGC         286
Ser Ile Ser Asn Ser Leu His Arg Glu Leu Ser Ala Gly Leu Val Gly
80                  85                  90                      95

CTG GGC CTT ACC TAC GCC CTA ATG GTC TCC AAC TAC CTC AAC TGG ATG         334
Leu Gly Leu Thr Tyr Ala Leu Met Val Ser Asn Tyr Leu Asn Trp Met
                100                 105                 110

GTG AGG AAC CTG GCA GAC ATG GAG CTC CAG CTG GGG GCT GTG AAG CGC         382
Val Arg Asn Leu Ala Asp Met Glu Leu Gln Leu Gly Ala Val Lys Arg
            115                 120                 125

ATC CAT GGG CTC CTG AAA ACC GAG GCA GAG AGC TAC GAG GGA CTC CTG         430
Ile His Gly Leu Leu Lys Thr Glu Ala Glu Ser Tyr Glu Gly Leu Leu
        130                 135                 140

GCA CCA TCG CTG ATC CCA AAG AAC TGG CCA GAC CAA GGG AAG ATC CAG         478
Ala Pro Ser Leu Ile Pro Lys Asn Trp Pro Asp Gln Gly Lys Ile Gln
145                 150                 155

ATC CAG AAC CTG AGC GTG CGC TAC GAC AGC TCC CTG AAG CCG GTG CTG         526
Ile Gln Asn Leu Ser Val Arg Tyr Asp Ser Ser Leu Lys Pro Val Leu
160                 165                 170                 175

AAG CAC GTC AAT GCC CTC ATC TCC CCT GGA CAG AAG ATC GGG ATC TGC         574
Lys His Val Asn Ala Leu Ile Ser Pro Gly Gln Lys Ile Gly Ile Cys
                180                 185                 190

GGC CGC ACC GGC AGT GGG AAG TCC TCC TTC TCT CTT GCC TTC TTC CGC         622
Gly Arg Thr Gly Ser Gly Lys Ser Ser Phe Ser Leu Ala Phe Phe Arg
            195                 200                 205

ATG GTG GAC ACG TTC GAA GGG CAC ATC ATC ATT GAT GGC ATT GAC ATC         670
Met Val Asp Thr Phe Glu Gly His Ile Ile Ile Asp Gly Ile Asp Ile
        210                 215                 220

GCC AAA CTG CCG CTG CAC ACC CTG CGC TCA CGC CTC TCC ATC ATC CTG         718
Ala Lys Leu Pro Leu His Thr Leu Arg Ser Arg Leu Ser Ile Ile Leu
225                 230                 235

CAG GAC CCC GTC CTC TTC AGC GGC ACC ATC CGA TTT AAC CTG GAC CCT         766
Gln Asp Pro Val Leu Phe Ser Gly Thr Ile Arg Phe Asn Leu Asp Pro
240                 245                 250                 255

GAG AGG AAG TGC TCA GAT AGC ACA CTG TGG GAG GCC CTG GAA ATC GCC         814
Glu Arg Lys Cys Ser Asp Ser Thr Leu Trp Glu Ala Leu Glu Ile Ala
                260                 265                 270

CAG CTG AAG CTG GTG GTG AAG GCA CTG CCA GGA GGC CTC GAT GCC ATC         862
Gln Leu Lys Leu Val Val Lys Ala Leu Pro Gly Gly Leu Asp Ala Ile
            275                 280                 285
```

| | | | | | | | | | | | | | | | |
|---|---|---|---|---|---|---|---|---|---|---|---|---|---|---|---|
| ATC | ACA | GAA | GGC | GGG | GAG | AAT | TTC | AGC | CAG | GGA | CAG | AGG | CAG | CTG | TTC | 910
| Ile | Thr | Glu | Gly | Gly | Glu | Asn | Phe | Ser | Gln | Gly | Gln | Arg | Gln | Leu | Phe |
| | | 290 | | | | | 295 | | | | | 300 | | | |

TGC CTG GCC CGG GCC TTC GTG AGG AAG ACC AGC ATC TTC ATC ATG GAC    958
Cys Leu Ala Arg Ala Phe Val Arg Lys Thr Ser Ile Phe Ile Met Asp
    305             310                 315

GAG GCC ACG GCT TCC ATT GAC ATG GCC ACG GAA AAC ATC CTC CAA AAG   1006
Glu Ala Thr Ala Ser Ile Asp Met Ala Thr Glu Asn Ile Leu Gln Lys
320                 325                 330                 335

GTG GTG ATG ACA GCC TTC GCA GAC CGC ACT GTG GTC ACC ATC GCG CAT   1054
Val Val Met Thr Ala Phe Ala Asp Arg Thr Val Val Thr Ile Ala His
            340                 345                 350

CGA GTG CAC ACC ATC CTG AGT GCA GAC CTG GTG ATC GTC CTG AAG CGG   1102
Arg Val His Thr Ile Leu Ser Ala Asp Leu Val Ile Val Leu Lys Arg
                355                 360                 365

GGT GCC ATC CTT GAG TTC GAT AAG CCA GAG AAG CTG CTC AGC CGG AAG   1150
Gly Ala Ile Leu Glu Phe Asp Lys Pro Glu Lys Leu Leu Ser Arg Lys
        370                 375                 380

GAC AGC GTC TTC GCC TCC TTC GTC CGT GCA GAC AAG TGACCTGCCA        1196
Asp Ser Val Phe Ala Ser Phe Val Arg Ala Asp Lys
    385                 390                 395

GAGCCCAAGT GCCATCCAC ATTCGGACCC TGCCCATACC CCTGCCTGGG TTTTCTAACT   1256

GTAAATCACT TGTAAATAAA TAGATTTGAT TATTTCCTAA AAAAAAAAA AA          1308

( 2 ) INFORMATION FOR SEQ ID NO:3:

( i ) SEQUENCE CHARACTERISTICS:
        ( A ) LENGTH: 395 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

Asp Leu Gln Gln Leu Asp Asp Thr Thr Gln Leu Pro Leu Leu Ser His
 1               5                  10                  15

Phe Ala Glu Thr Val Glu Gly Leu Thr Thr Ile Arg Ala Phe Arg Tyr
                20                  25                  30

Glu Ala Arg Phe Gln Gln Lys Leu Leu Glu Tyr Thr Asp Ser Asn Asn
            35                  40                  45

Ile Ala Ser Leu Phe Leu Thr Ala Ala Asn Arg Trp Leu Glu Val Arg
        50                  55                  60

Met Glu Tyr Ile Gly Ala Cys Val Val Leu Ile Ala Ala Val Thr Ser
65                  70                  75                  80

Ile Ser Asn Ser Leu His Arg Glu Leu Ser Ala Gly Leu Val Gly Leu
                85                  90                  95

Gly Leu Thr Tyr Ala Leu Met Val Ser Asn Tyr Leu Asn Trp Met Val
            100                 105                 110

Arg Asn Leu Ala Asp Met Glu Leu Gln Leu Gly Ala Val Lys Arg Ile
        115                 120                 125

His Gly Leu Leu Lys Thr Glu Ala Glu Ser Tyr Glu Gly Leu Leu Ala
    130                 135                 140

Pro Ser Leu Ile Pro Lys Asn Trp Pro Asp Gln Gly Lys Ile Gln Ile
145                 150                 155                 160

Gln Asn Leu Ser Val Arg Tyr Asp Ser Ser Leu Lys Pro Val Leu Lys
                165                 170                 175

His Val Asn Ala Leu Ile Ser Pro Gly Gln Lys Ile Gly Ile Cys Gly
            180                 185                 190

```
Arg  Thr  Gly  Ser  Gly  Lys  Ser  Ser  Phe  Ser  Leu  Ala  Phe  Phe  Arg  Met
          195                      200                     205

Val  Asp  Thr  Phe  Glu  Gly  His  Ile  Ile  Ile  Asp  Gly  Ile  Asp  Ile  Ala
     210                      215                     220

Lys  Leu  Pro  Leu  His  Thr  Leu  Arg  Ser  Arg  Leu  Ser  Ile  Ile  Leu  Gln
225                      230                     235                          240

Asp  Pro  Val  Leu  Phe  Ser  Gly  Thr  Ile  Arg  Phe  Asn  Leu  Asp  Pro  Glu
                    245                     250                     255

Arg  Lys  Cys  Ser  Asp  Ser  Thr  Leu  Trp  Glu  Ala  Leu  Glu  Ile  Ala  Gln
               260                      265                     270

Leu  Lys  Leu  Val  Val  Lys  Ala  Leu  Pro  Gly  Gly  Leu  Asp  Ala  Ile  Ile
          275                      280                     285

Thr  Glu  Gly  Gly  Glu  Asn  Phe  Ser  Gln  Gly  Gln  Arg  Gln  Leu  Phe  Cys
     290                      295                     300

Leu  Ala  Arg  Ala  Phe  Val  Arg  Lys  Thr  Ser  Ile  Phe  Ile  Met  Asp  Glu
305                      310                     315                          320

Ala  Thr  Ala  Ser  Ile  Asp  Met  Ala  Thr  Glu  Asn  Ile  Leu  Gln  Lys  Val
               325                      330                     335

Val  Met  Thr  Ala  Phe  Ala  Asp  Arg  Thr  Val  Val  Thr  Ile  Ala  His  Arg
               340                      345                     350

Val  His  Thr  Ile  Leu  Ser  Ala  Asp  Leu  Val  Ile  Val  Leu  Lys  Arg  Gly
          355                      360                     365

Ala  Ile  Leu  Glu  Phe  Asp  Lys  Pro  Glu  Lys  Leu  Leu  Ser  Arg  Lys  Asp
          370                      375                     380

Ser  Val  Phe  Ala  Ser  Phe  Val  Arg  Ala  Asp  Lys
385                      390                     395
```

(2) INFORMATION FOR SEQ ID NO:4:

(i) SEQUENCE CHARACTERISTICS:
        (A) LENGTH: 5110 base pairs
        (B) TYPE: nucleic acid
        (C) STRANDEDNESS: single
        (D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:4:

```
CCCTTGTGAC  AGGTCAGTCT  TACGAGAATA  TGGTAACTGA  GATCATGTCA  ATGGGCTATG       60
AACGAGAACA  AGTAATTGCA  GCCCTGAGAG  CCAGCTTCAA  CAACCCTGAT  AGAGCTGTGG      120
AATATCTTCT  AATGGGAATC  CCTGGAGACT  GAGGAGTTCC  AGTACTCACA  GCCTGTGGAG      180
GAGGATCAAC  CACGGCCTGA  CTTTCGCGGC  CGCCGCGGGA  GGCGCGCGGA  GCCGGAGCCG      240
AGCCCGTGCG  CGCGCCACCA  TGCCTTTGGC  CTTCTGCGGC  ACCGAGAACC  ACTCGGCCGC      300
CTACCGGGTG  GACCAAGGCG  TCCTCAACAA  CGGCTGCTTC  GTGGACGCGC  TCAATGTGGT      360
GCCACATGTC  TTTCTGCTCT  TCATCACCTT  CCCCATCCTC  TTCATCGGAT  GGGGCAGCCA      420
GAGCTCCAAG  GTGCACATTC  ACCACAGCAC  CTGGCTCCAT  TTCCCGGGGC  ACAACCTGCG      480
CTGGATCCTG  ACCTTCATAC  TGCTCTTCGT  CCTCGTGTGT  GAGATCGCTG  AGGGTATCCT      540
GTCTGACGGG  GTGACAGAAT  CCCGCCACCT  CCACTTATAC  ATGCCAGCTG  GGATGGCATT      600
CATGGCTGCC  ATCACCTCTG  TGGTCTACTA  CCATAACATT  GAGACCTCTA  ACTTTCCCAA      660
GCTGCTGATT  GCTCTGCTCA  TCTACTGGAC  CCTGGCCTTC  ATCACGAAGA  CCATCAAGTT      720
```

```
CGTCAAGTTC  TACGACCACG  CCATTGGCTT  CTCTCAGCTG  CGCTTCTGCC  TCACGGGGCT   780
TCTGGTGATC  CTCTACGGGA  TGCTGCTGCT  TGTGGAGGTC  AATGTCATCC  GGGTGAGGAG   840
ATACGTCTTC  TTCAAGACAC  CAAGGGAAGT  AAAGCCCCCC  GAGGACCTAC  AGGACCTGGG   900
TGTGCGCTTT  CTGCAGCCCT  TCGTTAACCT  GCTATCAAAG  GGGACCTACT  GGTGGATGAA   960
TGCCTTCATC  AAGACTGCTC  ACAAGAAGCC  CATCGACCTG  CGGGCCATCG  GAAGCTGCC   1020
CATTGCCATG  AGAGCCCTCA  CCAACTACCA  GCGACTCTGC  TTGGCCTTCG  ATGCCCAGGC  1080
GCGGAAGGAC  ACACAGAGCC  AGCAGGGTGC  CCGGGCCATC  TGGAGGGCTC  TCTGTCATGC  1140
CTTTGGGAGA  CGGCTGGTCC  TCAGCAGCAC  ATTCCGTATC  CTGGCCGACC  TCCTGGGCTT  1200
TGCTGGGCCA  CTCTGCATCT  TCGGGATCGT  GGACCACCTC  GGGAAGGAGA  ACCACGTCTT  1260
CCAGCCCAAG  ACACAGTTTC  TTGGAGTTTA  CTTTGTCTCA  TCCCAAGAGT  TCCTCGGCAA  1320
TGCCTATGTC  TTGGCTGTTC  TTCTGTTCCT  TGCCCTCCTG  CTGCAAGGA  CCTTTCTACA  1380
AGCCTCGTAC  TACGTTGCCA  TTGAAACTGG  GATCAACCTG  AGAGGAGCAA  TCCAGACCAA  1440
GATTTACAAT  AAGATCATGC  ACTTGTCTAC  TTCCAACCTG  TCCATGGGGG  AAATGACTGC  1500
TGGGCAGATC  TGCAACCTGG  TGGCCATCGA  CACCAACCAG  CTCATGTGGT  TTTTCTTCTT  1560
ATGCCCAAAC  CTCTGGGCTA  TGCCGGTACA  GATCATTGTG  GGCGTGATCC  TCCTCTACTA  1620
CATCCTTGGG  GTCAGCGCCT  TGATTGGAGC  GGCTGTCATC  ATTCTGCTGG  CTCCTGTACA  1680
GTACTTTGTG  GCCACCAAGC  TGTCCCAGGC  ACAGCGGACG  ACCCTGGAAT  ATTCCAATGA  1740
GAGGCTGAAG  CAGACCAATG  AGATGCTCCG  GGGCATCAAG  TTGCTCAAGC  TCTATGCGTG  1800
GGAGAACATC  TTCTGCTCCA  GGGTGGAGAA  GACACGCAGG  AAGGAAATGA  CCAGCCTCAG  1860
GGCCTTCGCT  GTCTACACCT  CCATCTCCAT  CTTCATGAAC  ACAGCTATCC  CCATCGCTGC  1920
TGTCCTCATC  ACCTTCGTGG  GCCACGTCAG  CTTCTTCAAA  GAGTCGGACT  TCTCGCCCTC  1980
GGTGGCCTTT  GCCTCTCTCT  CTCTCTTCCA  CATCCTGGTC  ACACCGCTGT  TCCTGCTGTC  2040
TAGTGTGGTT  CGGTCCACTG  TCAAGGCCCT  GGTGAGCGTG  CAAAAGCTGA  GTGAGTTCCT  2100
GTCCAGTGCA  GAGATCCGTG  AGGAACAGTG  TGCCCCCCGA  GAGCCCGCAC  CCCAAGGCCA  2160
AGCGGGCAAG  TACCAGGCGG  TGCCCCTCAA  GGTCGTAAAC  CGCAAGCGCC  AGCCCGAGA   2220
AGAAGTCCGG  GACCTCTTGG  GCCCACTGCA  GAGGCTGACT  CCCAGCACGG  ATGGAGACGC  2280
TGACAACTTC  TGTGTCCAGA  TCATCGGAGG  CTTCTTCACC  TGGACCCCTG  ATGGAATCCC  2340
CACCCTGTCC  AACATCACCA  TCCGTATCCC  CCGAGGTCAG  CTGACCATGA  TCGTGGGGCA  2400
GGTGGGCTGT  GGCAAGTCCT  CGCTCCTTCT  GGCCACCCTG  GGGGAGATGC  AGAAGGTCTC  2460
TGGAGCTGTC  TTCTGGAACA  GCCTTCCAGA  CAGCGAGGGG  AGAAGACCCC  AGCAACCCAG  2520
AGCGGGAGAC  AGCGGCCGAT  TCGGATGCCA  GGAGCAGAGG  CCCTGTGGCT  ACGCATCTCA  2580
GAAACCATGG  CTGCTAAATG  CCACTGTGGA  GGAGAACATC  ACCTTCGAGA  GTCCCTTCAA  2640
TAAGCAACGG  TACAAGATGG  TCATCGAAGC  CTGCTCCCTG  CAGCCAGACA  TAGACATCCT  2700
GCCCCATGGA  GACCAGACTC  AGATTGGGGA  ACGAGGCATC  AACTTGAGTA  CTGGTGGTCA  2760
GCGTCCAGAT  CAGTGTAGAC  CCGAGCCCTC  TACCAGCACA  CCAATGATTG  TCTTTTTGGA  2820
TGACCCTTTC  TCGGCTCTGG  ATGTCCATCT  GAGTGACCAC  CTAATGCAGG  CTGGCATCCT  2880
CGAGCTGCTC  CGGGATGACA  AGAGGACAGT  GGTCTTGGTG  ACCCACAAGC  TACAGTACCT  2940
GCCTCATGCT  GACTGGATCA  TTGCTATGAA  GGATGGCACC  ATTCAGAGGG  AGGGACACT   3000
CAAGGACTTC  CAGAGGTCTG  AGTGCCAGCT  CTTTGAGCAT  TGGAAGACCC  TCATGAACCG  3060
GCAGGACCAA  GAGCTGGAGA  AGGAGACAGT  CATGGAGAGA  AAAGCCCCAG  AGCCATCTCA  3120
```

-continued

```
GGGCCTGCCC CGTGCCATGT CCTCAAGAGA TGGCCTTCTG CTGGATGAGG ATGAGGAGGA    3180
AGAGGAGGCA GCCGAGAGCG AGGAAGATGA CAACTTATCC TCTGTGCTGC ATCAGCGAGC    3240
CAAGATCCCA TGGCGAGCCT GCACCAAGTA TTTGTCCTCT GCTGGCATCC TGCTCCTGTC    3300
CCTGCTTGTC TTCTCCCAGC TGCTCAAGCA CATGGTCTTG GTGGCCATTG ACTACTGGCT    3360
GGCCAAGTGG ACGGACAGTG CCCTGGTCCT GAGCCCCGCC GCCAGGAACT GCTCCCTCAG    3420
CCAGGAATGT GCCCTGGACC AATCTGTCTA TGCCATGGTA TTCACCGTGC TCTGCAGCCT    3480
GGGTATCGCG CTGTGCCTTG TCACCTCTGT CACTGTGGAG TGGACGGGAC TGAAGGTGGC    3540
CAAGAGGCTG CATCGCAGCC TGCTCAACCG TATCATCCTG GCTCCCATGA GGTTCTTTGA    3600
GACCACGCCC CTGGGGAGTA TCCTGAACAG ATTTTCATCT GACTGTAACA CCATTGACCA    3660
GCATATCCCG TCCACGCTGG AGTGCCTGAG CAGATCCACC TTACTCTGTG TCTCCGCCCT    3720
GGCTGTCATC TCCTACGTCA CGCCTGTGTT CCTAGTGGCC CTCTTACCCC TCGCCGTCGT    3780
GTGCTACTTC ATCCAGAAGT ACTTCCGAGT GGCGTCCAGG GACCTGCAGC AGCTGGACGA    3840
CACAACACAG CTCCCTCTGC TCTCACACTT TGCTGAAACT GTGGAAGGAC TCACCACCAT    3900
CCGTGCCTTC AGGTACGAGG CCCGGTTCCA GCAGAAGCTC CTAGAGTACA CCGACTCCAA    3960
CAACATTGCC TCTCTCTTCC TCACAGCAGC CAACAGGTGG CTGGAAGTCC GCATGGAGTA    4020
CATCGGAGCA TGCGTGGTAC TCATCGCCGC TGCCACCTCC ATCTCCAACT CCCTACACAG    4080
GGAGCTCTCA GCCGGCCTAG TAGGCCTGGG CCTCACCTAT GCCTTGATGG TCTCCAACTA    4140
CCTCAACTGG ATGGTGAGGA ACCTGGCAGA CATGGAGATC CAACTGGGAG CTGTGAAGGG    4200
TATCCACACA CTCCTGAAAA CTGAGGCAGA GAGCTATGAG GGGCTCCTGG CACCATCGCT    4260
GATCCCCAAG AACTGGCCAG ACCAAGGGAA GATCCAAATT CAAAACCTGA GTGTACGCTA    4320
TGACAGCTCC CTGAAGCCCG TGCTGAAGCA CGTCAACGCC CTCATCTCCC AGGACAGAA    4380
GATTGGGATC TGCGGCCGCA CAGGCAGTGG AAAATCCTCC TTCTCTCTCG CCTTTTTCCG    4440
AATGGTGGAT ATGTTTGAAG GGCGTATCAT CATCGATGGC ATTGACATCG CCAAGCTGCC    4500
GCTGCACACG CTCGGCTCAC GCCTGTCTAT CATCCTACAG GACCCTGTTC TCTTCAGTGG    4560
TACCATCAGA TTCAACCTGG ACCCAGAGAA GAAATGCTCA GACAGCACGC TGTGGGAGGC    4620
TCTGGAGATC GCTCAGCTGA AGCTGGTGGT GAAGGCCCTG CCAGGAGGCC TGGATGCCAT    4680
CATCACGGAA GGAGGGGAGA ATTTTAGCCA GGGCCAGAGG CAGCTGTTCT GCCTGGCCCG    4740
GGCCTTTGTG AGGAAGACCA GCATCTTCAT CATGGATGAA GCAACTGCCT CCATCGACAT    4800
GGCTACGGAA AATATCCTCC AGAAGGTGGT GATGACAGCC TTCGCAGACC GCACCGTGGT    4860
CACCATCGCG CACCGCGTGC ACACCATCCT GAGTGCAGAC CTAGTGATGG TCCTGAAGAG    4920
GGGCGCGATC CTGGAGTTCG ACAAGCCGGA AAAGCTTCTC AGCCAGAAGG ACAGCGTCTT    4980
TGCCTCCTTT GTCCGCGCGG ACAAATGACC AGCCAGCGCC AAAGTGCCAC CCACACCTC    5040
ACCTGCTTGC CATGGATTTC TTACTGTAAA TCACTTGTAA ATAAAGAAAC TAATTCTTTG    5100
CTAAAAAAAA                                                            5110
```

( 2 ) INFORMATION FOR SEQ ID NO:5:

( i ) SEQUENCE CHARACTERISTICS:
        ( A ) LENGTH: 5110 base pairs
        ( B ) TYPE: nucleic acid
        ( C ) STRANDEDNESS: single
        ( D ) TOPOLOGY: linear ( i i ) MOLECULE TYPE: DNA (genomic)

-continued (iii) HYPOTHETICAL: NO (iv) ANTI-SENSE: NO (ix) FEATURE:
    (A) NAME/KEY: CDS
    (B) LOCATION: 260..5004

(xi) SEQUENCE DESCRIPTION: SEQ ID NO:5:

```
CCCTTGTGAC AGGTCAGTCT TACGAGAATA TGGTAACTGA GATCATGTCA ATGGGCTATG        60

AACGAGAACA AGTAATTGCA GCCCTGAGAG CCAGCTTCAA CAACCCTGAT AGAGCTGTGG       120

AATATCTTCT AATGGGAATC CCTGGAGACT GAGGAGTTCC AGTACTCACA GCCTGTGGAG       180

GAGGATCAAC CACGGCCTGA CTTTCGCGGC CGCCGCGGGA GGCGCGCGGA GCCGGAGCCG       240

AGCCCGTGCG CGCGCCACC ATG CCT TTG GCC TTC TGC GGC ACC GAG AAC CAC       292
                      Met Pro Leu Ala Phe Cys Gly Thr Glu Asn His
                        1               5                      10

TCG GCC GCC TAC CGG GTG GAC CAA GGC GTC CTC AAC AAC GGC TGC TTC        340
Ser Ala Ala Tyr Arg Val Asp Gln Gly Val Leu Asn Asn Gly Cys Phe
             15                  20                  25

GTG GAC GCG CTC AAT GTG GTG CCA CAT GTC TTT CTG CTC TTC ATC ACC        388
Val Asp Ala Leu Asn Val Val Pro His Val Phe Leu Leu Phe Ile Thr
         30                  35                  40

TTC CCC ATC CTC TTC ATC GGA TGG GGC AGC CAG AGC TCC AAG GTG CAC        436
Phe Pro Ile Leu Phe Ile Gly Trp Gly Ser Gln Ser Ser Lys Val His
     45                  50                  55

ATT CAC CAC AGC ACC TGG CTC CAT TTC CCG GGG CAC AAC CTG CGC TGG        484
Ile His His Ser Thr Trp Leu His Phe Pro Gly His Asn Leu Arg Trp
 60                  65                  70                  75

ATC CTG ACC TTC ATA CTG CTC TTC GTC CTC GTG TGT GAG ATC GCT GAG        532
Ile Leu Thr Phe Ile Leu Leu Phe Val Leu Val Cys Glu Ile Ala Glu
                     80                  85                  90

GGT ATC CTG TCT GAC GGG GTG ACA GAA TCC CGC CAC CTC CAC TTA TAC        580
Gly Ile Leu Ser Asp Gly Val Thr Glu Ser Arg His Leu His Leu Tyr
                 95                 100                 105

ATG CCA GCT GGG ATG GCA TTC ATG GCT GCC ATC ACC TCT GTG GTC TAC        628
Met Pro Ala Gly Met Ala Phe Met Ala Ala Ile Thr Ser Val Val Tyr
         110                 115                 120

TAC CAT AAC ATT GAG ACC TCT AAC TTT CCC AAG CTG CTG ATT GCT CTG        676
Tyr His Asn Ile Glu Thr Ser Asn Phe Pro Lys Leu Leu Ile Ala Leu
     125                 130                 135

CTC ATC TAC TGG ACC CTG GCC TTC ATC ACG AAG ACC ATC AAG TTC GTC        724
Leu Ile Tyr Trp Thr Leu Ala Phe Ile Thr Lys Thr Ile Lys Phe Val
140                 145                 150                 155

AAG TTC TAC GAC CAC GCC ATT GGC TTC TCT CAG CTG CGC TTC TGC CTC        772
Lys Phe Tyr Asp His Ala Ile Gly Phe Ser Gln Leu Arg Phe Cys Leu
                 160                 165                 170

ACG GGG CTT CTG GTG ATC CTC TAC GGG ATG CTG CTG CTT GTG GAG GTC        820
Thr Gly Leu Leu Val Ile Leu Tyr Gly Met Leu Leu Leu Val Glu Val
                 175                 180                 185

AAT GTC ATC CGG GTG AGG AGA TAC GTC TTC TTC AAG ACA CCA AGG GAA        868
Asn Val Ile Arg Val Arg Arg Tyr Val Phe Phe Lys Thr Pro Arg Glu
         190                 195                 200

GTA AAG CCC CCC GAG GAC CTA CAG GAC CTG GGT GTG CGC TTT CTG CAG        916
Val Lys Pro Pro Glu Asp Leu Gln Asp Leu Gly Val Arg Phe Leu Gln
     205                 210                 215

CCC TTC GTT AAC CTG CTA TCA AAG GGG ACC TAC TGG TGG ATG AAT GCC        964
Pro Phe Val Asn Leu Leu Ser Lys Gly Thr Tyr Trp Trp Met Asn Ala
 220                 225                 230                 235

TTC ATC AAG ACT GCT CAC AAG AAG CCC ATC GAC CTG CGG GCC ATC GGG       1012
Phe Ile Lys Thr Ala His Lys Lys Pro Ile Asp Leu Arg Ala Ile Gly
```

|     |     |     |     |     |     |     |     |     |     |     |     |     |     |     |     |      |
|---|---|---|---|---|---|---|---|---|---|---|---|---|---|---|---|---|
|     |     |     |     |     |     | 240 |     |     |     | 245 |     |     |     | 250 |     |      |
| AAG | CTG | CCC | ATT | GCC | ATG | AGA | GCC | CTC | ACC | AAC | TAC | CAG | CGA | CTC | TGC | 1060 |
| Lys | Leu | Pro | Ile | Ala | Met | Arg | Ala | Leu | Thr | Asn | Tyr | Gln | Arg | Leu | Cys |      |
|     |     |     | 255 |     |     |     |     | 260 |     |     |     | 265 |     |     |     |      |
| TTG | GCC | TTC | GAT | GCC | CAG | GCG | CGG | AAG | GAC | ACA | CAG | AGC | CAG | CAG | GGT | 1108 |
| Leu | Ala | Phe | Asp | Ala | Gln | Ala | Arg | Lys | Asp | Thr | Gln | Ser | Gln | Gln | Gly |      |
|     |     | 270 |     |     |     |     | 275 |     |     |     |     | 280 |     |     |     |      |
| GCC | CGG | GCC | ATC | TGG | AGG | GCT | CTC | TGT | CAT | GCC | TTT | GGG | AGA | CGG | CTG | 1156 |
| Ala | Arg | Ala | Ile | Trp | Arg | Ala | Leu | Cys | His | Ala | Phe | Gly | Arg | Arg | Leu |      |
|     | 285 |     |     |     |     | 290 |     |     |     |     | 295 |     |     |     |     |      |
| GTC | CTC | AGC | AGC | ACA | TTC | CGT | ATC | CTG | GCC | GAC | CTC | CTG | GGC | TTT | GCT | 1204 |
| Val | Leu | Ser | Ser | Thr | Phe | Arg | Ile | Leu | Ala | Asp | Leu | Leu | Gly | Phe | Ala |      |
| 300 |     |     |     |     | 305 |     |     |     |     | 310 |     |     |     |     | 315 |      |
| GGG | CCA | CTC | TGC | ATC | TTC | GGG | ATC | GTG | GAC | CAC | CTC | GGG | AAG | GAG | AAC | 1252 |
| Gly | Pro | Leu | Cys | Ile | Phe | Gly | Ile | Val | Asp | His | Leu | Gly | Lys | Glu | Asn |      |
|     |     |     |     | 320 |     |     |     |     | 325 |     |     |     |     | 330 |     |      |
| CAC | GTC | TTC | CAG | CCC | AAG | ACA | CAG | TTT | CTT | GGA | GTT | TAC | TTT | GTC | TCA | 1300 |
| His | Val | Phe | Gln | Pro | Lys | Thr | Gln | Phe | Leu | Gly | Val | Tyr | Phe | Val | Ser |      |
|     |     |     | 335 |     |     |     |     | 340 |     |     |     |     | 345 |     |     |      |
| TCC | CAA | GAG | TTC | CTC | GGC | AAT | GCC | TAT | GTC | TTG | GCT | GTT | CTT | CTG | TTC | 1348 |
| Ser | Gln | Glu | Phe | Leu | Gly | Asn | Ala | Tyr | Val | Leu | Ala | Val | Leu | Leu | Phe |      |
|     |     | 350 |     |     |     |     | 355 |     |     |     |     | 360 |     |     |     |      |
| CTT | GCC | CTC | CTG | CTG | CAA | AGG | ACC | TTT | CTA | CAA | GCC | TCG | TAC | TAC | GTT | 1396 |
| Leu | Ala | Leu | Leu | Leu | Gln | Arg | Thr | Phe | Leu | Gln | Ala | Ser | Tyr | Tyr | Val |      |
|     | 365 |     |     |     |     | 370 |     |     |     |     | 375 |     |     |     |     |      |
| GCC | ATT | GAA | ACT | GGG | ATC | AAC | CTG | AGA | GGA | GCA | ATC | CAG | ACC | AAG | ATT | 1444 |
| Ala | Ile | Glu | Thr | Gly | Ile | Asn | Leu | Arg | Gly | Ala | Ile | Gln | Thr | Lys | Ile |      |
| 380 |     |     |     |     | 385 |     |     |     |     | 390 |     |     |     |     | 395 |      |
| TAC | AAT | AAG | ATC | ATG | CAC | TTG | TCT | ACT | TCC | AAC | CTG | TCC | ATG | GGG | GAA | 1492 |
| Tyr | Asn | Lys | Ile | Met | His | Leu | Ser | Thr | Ser | Asn | Leu | Ser | Met | Gly | Glu |      |
|     |     |     |     | 400 |     |     |     |     | 405 |     |     |     |     | 410 |     |      |
| ATG | ACT | GCT | GGG | CAG | ATC | TGC | AAC | CTG | GTG | GCC | ATC | GAC | ACC | AAC | CAG | 1540 |
| Met | Thr | Ala | Gly | Gln | Ile | Cys | Asn | Leu | Val | Ala | Ile | Asp | Thr | Asn | Gln |      |
|     |     |     | 415 |     |     |     |     | 420 |     |     |     |     | 425 |     |     |      |
| CTC | ATG | TGG | TTT | TTC | TTC | TTA | TGC | CCA | AAC | CTC | TGG | GCT | ATG | CCG | GTA | 1588 |
| Leu | Met | Trp | Phe | Phe | Phe | Leu | Cys | Pro | Asn | Leu | Trp | Ala | Met | Pro | Val |      |
|     |     | 430 |     |     |     |     | 435 |     |     |     |     | 440 |     |     |     |      |
| CAG | ATC | ATT | GTG | GGC | GTG | ATC | CTC | CTC | TAC | TAC | ATC | CTT | GGG | GTC | AGC | 1636 |
| Gln | Ile | Ile | Val | Gly | Val | Ile | Leu | Leu | Tyr | Tyr | Ile | Leu | Gly | Val | Ser |      |
|     | 445 |     |     |     |     | 450 |     |     |     |     | 455 |     |     |     |     |      |
| GCC | TTG | ATT | GGA | GCG | GCT | GTC | ATC | ATT | CTG | CTG | GCT | CCT | GTA | CAG | TAC | 1684 |
| Ala | Leu | Ile | Gly | Ala | Ala | Val | Ile | Ile | Leu | Leu | Ala | Pro | Val | Gln | Tyr |      |
| 460 |     |     |     |     | 465 |     |     |     |     | 470 |     |     |     |     | 475 |      |
| TTT | GTG | GCC | ACC | AAG | CTG | TCC | CAG | GCA | CAG | CGG | ACG | ACC | CTG | GAA | TAT | 1732 |
| Phe | Val | Ala | Thr | Lys | Leu | Ser | Gln | Ala | Gln | Arg | Thr | Thr | Leu | Glu | Tyr |      |
|     |     |     |     | 480 |     |     |     |     | 485 |     |     |     |     | 490 |     |      |
| TCC | AAT | GAG | AGG | CTG | AAG | CAG | ACC | AAT | GAG | ATG | CTC | CGG | GGC | ATC | AAG | 1780 |
| Ser | Asn | Glu | Arg | Leu | Lys | Gln | Thr | Asn | Glu | Met | Leu | Arg | Gly | Ile | Lys |      |
|     |     |     | 495 |     |     |     |     | 500 |     |     |     |     | 505 |     |     |      |
| TTG | CTC | AAG | CTC | TAT | GCG | TGG | GAG | AAC | ATC | TTC | TGC | TCC | AGG | GTG | GAG | 1828 |
| Leu | Leu | Lys | Leu | Tyr | Ala | Trp | Glu | Asn | Ile | Phe | Cys | Ser | Arg | Val | Glu |      |
|     |     | 510 |     |     |     |     | 515 |     |     |     |     | 520 |     |     |     |      |
| AAG | ACA | CGC | AGG | AAG | GAA | ATG | ACC | AGC | CTC | AGG | GCC | TTC | GCT | GTC | TAC | 1876 |
| Lys | Thr | Arg | Arg | Lys | Glu | Met | Thr | Ser | Leu | Arg | Ala | Phe | Ala | Val | Tyr |      |
|     | 525 |     |     |     |     | 530 |     |     |     |     | 535 |     |     |     |     |      |
| ACC | TCC | ATC | TCC | ATC | TTC | ATG | AAC | ACA | GCT | ATC | CCC | ATC | GCT | GCT | GTC | 1924 |
| Thr | Ser | Ile | Ser | Ile | Phe | Met | Asn | Thr | Ala | Ile | Pro | Ile | Ala | Ala | Val |      |
| 540 |     |     |     |     | 545 |     |     |     |     | 550 |     |     |     |     | 555 |      |
| CTC | ATC | ACC | TTC | GTG | GGC | CAC | GTC | AGC | TTC | TTC | AAA | GAG | TCG | GAC | TTC | 1972 |
| Leu | Ile | Thr | Phe | Val | Gly | His | Val | Ser | Phe | Phe | Lys | Glu | Ser | Asp | Phe |      |

| | | | | | | | | | | | | | | | | |
|---|---|---|---|---|---|---|---|---|---|---|---|---|---|---|---|---|
| | | | | | 560 | | | | | 565 | | | | | 570 | |
| TCG | CCC | TCG | GTG | GCC | TTT | GCC | TCT | CTC | TCT | CTC | TTC | CAC | ATC | CTG | GTC | 2020 |
| Ser | Pro | Ser | Val 575 | Ala | Phe | Ala | Ser | Leu 580 | Ser | Leu | Phe | His | Ile 585 | Leu | Val | |
| ACA | CCG | CTG | TTC | CTG | CTG | TCT | AGT | GTG | GTT | CGG | TCC | ACT | GTC | AAG | GCC | 2068 |
| Thr | Pro | Leu 590 | Phe | Leu | Leu | Ser | Ser 595 | Val | Val | Arg | Ser | Thr 600 | Val | Lys | Ala | |
| CTG | GTG | AGC | GTG | CAA | AAG | CTG | AGT | GAG | TTC | CTG | TCC | AGT | GCA | GAG | ATC | 2116 |
| Leu | Val 605 | Ser | Val | Gln | Lys | Leu 610 | Ser | Glu | Phe | Leu | Ser 615 | Ser | Ala | Glu | Ile | |
| CGT | GAG | GAA | CAG | TGT | GCC | CCC | CGA | GAG | CCC | GCA | CCC | CAA | GGC | CAA | GCG | 2164 |
| Arg 620 | Glu | Glu | Gln | Cys | Ala 625 | Pro | Arg | Glu | Pro | Ala 630 | Pro | Gln | Gly | Gln | Ala 635 | |
| GGC | AAG | TAC | CAG | GCG | GTG | CCC | CTC | AAG | GTC | GTA | AAC | CGC | AAG | CGC | CCA | 2212 |
| Gly | Lys | Tyr | Gln | Ala 640 | Val | Pro | Leu | Lys | Val 645 | Val | Asn | Arg | Lys | Arg 650 | Pro | |
| GCC | CGA | GAA | GAA | GTC | CGG | GAC | CTC | TTG | GGC | CCA | CTG | CAG | AGG | CTG | ACT | 2260 |
| Ala | Arg | Glu | Glu 655 | Val | Arg | Asp | Leu | Leu 660 | Gly | Pro | Leu | Gln | Arg 665 | Leu | Thr | |
| CCC | AGC | ACG | GAT | GGA | GAC | GCT | GAC | AAC | TTC | TGT | GTC | CAG | ATC | ATC | GGA | 2308 |
| Pro | Ser | Thr | Asp 670 | Gly | Asp | Ala | Asp | Asn 675 | Phe | Cys | Val | Gln | Ile 680 | Ile | Gly | |
| GGC | TTC | TTC | ACC | TGG | ACC | CCT | GAT | GGA | ATC | CCC | ACC | CTG | TCC | AAC | ATC | 2356 |
| Gly | Phe | Phe 685 | Thr | Trp | Thr | Pro | Asp 690 | Gly | Ile | Pro | Thr | Leu 695 | Ser | Asn | Ile | |
| ACC | ATC | CGT | ATC | CCC | CGA | GGT | CAG | CTG | ACC | ATG | ATC | GTG | GGG | CAG | GTG | 2404 |
| Thr | Ile 700 | Arg | Ile | Pro | Arg 705 | Gly | Gln | Leu | Thr | Met 710 | Ile | Val | Gly | Gln | Val 715 | |
| GGC | TGT | GGC | AAG | TCC | TCG | CTC | CTT | CTG | GCC | ACC | CTG | GGG | GAG | ATG | CAG | 2452 |
| Gly | Cys | Gly | Lys | Ser 720 | Ser | Leu | Leu | Leu | Ala 725 | Thr | Leu | Gly | Glu | Met 730 | Gln | |
| AAG | GTC | TCT | GGA | GCT | GTC | TTC | TGG | AAC | AGC | CTT | CCA | GAC | AGC | GAG | GGG | 2500 |
| Lys | Val | Ser | Gly 735 | Ala | Val | Phe | Trp | Asn 740 | Ser | Leu | Pro | Asp | Ser 745 | Glu | Gly | |
| AGA | AGA | CCC | CAG | CAA | CCC | AGA | GCG | GGA | GAC | AGC | GGC | CGA | TTC | GGA | TGC | 2548 |
| Arg | Arg | Pro 750 | Gln | Gln | Pro | Arg | Ala 755 | Gly | Asp | Ser | Gly | Arg 760 | Phe | Gly | Cys | |
| CAG | GAG | CAG | AGG | CCC | TGT | GGC | TAC | GCA | TCT | CAG | AAA | CCA | TGG | CTG | CTA | 2596 |
| Gln | Glu | Gln | Arg 765 | Pro | Cys | Gly | Tyr | Ala 770 | Ser | Gln | Lys | Pro | Trp 775 | Leu | Leu | |
| AAT | GCC | ACT | GTG | GAG | GAG | AAC | ATC | ACC | TTC | GAG | AGT | CCC | TTC | AAT | AAG | 2644 |
| Asn | Ala | Thr | Val 780 | Glu | Glu | Asn | Ile | Thr 785 | Phe | Glu | Ser | Pro | Phe 790 | Asn | Lys 795 | |
| CAA | CGG | TAC | AAG | ATG | GTC | ATC | GAA | GCC | TGC | TCC | CTG | CAG | CCA | GAC | ATA | 2692 |
| Gln | Arg | Tyr | Lys | Met 800 | Val | Ile | Glu | Ala | Cys 805 | Ser | Leu | Gln | Pro | Asp 810 | Ile | |
| GAC | ATC | CTG | CCC | CAT | GGA | GAC | CAG | ACT | CAG | ATT | GGG | GAA | CGA | GGC | ATC | 2740 |
| Asp | Ile | Leu | Pro 815 | His | Gly | Asp | Gln | Thr 820 | Gln | Ile | Gly | Glu | Arg 825 | Gly | Ile | |
| AAC | TTG | AGT | ACT | GGT | GGT | CAG | CGT | CCA | GAT | CAG | TGT | AGA | CCC | GAG | CCC | 2788 |
| Asn | Leu | Ser | Thr 830 | Gly | Gly | Gln | Arg | Pro 835 | Asp | Gln | Cys | Arg | Pro 840 | Glu | Pro | |
| TCT | ACC | AGC | ACA | CCA | ATG | ATT | GTC | TTT | TTG | GAT | GAC | CCT | TTC | TCG | GCT | 2836 |
| Ser | Thr | Ser | Thr 845 | Pro | Met | Ile | Val | Phe 850 | Leu | Asp | Asp | Pro | Phe 855 | Ser | Ala | |
| CTG | GAT | GTC | CAT | CTG | AGT | GAC | CAC | CTA | ATG | CAG | GCT | GGC | ATC | CTC | GAG | 2884 |
| Leu | Asp | Val | His 860 | Leu | Ser | Asp | His | Leu 865 | Met | Gln | Ala | Gly | Ile 870 | Leu | Glu 875 | |
| CTG | CTC | CGG | GAT | GAC | AAG | AGG | ACA | GTG | GTC | TTG | GTG | ACC | CAC | AAG | CTA | 2932 |
| Leu | Leu | Arg | Asp | Asp | Lys | Arg | Thr | Val | Val | Leu | Val | Thr | His | Lys | Leu | |

```
                          880                         885                         890
CAG  TAC  CTG  CCT  CAT  GCT  GAC  TGG  ATC  ATT  GCT  ATG  AAG  GAT  GGC  ACC         2980
Gln  Tyr  Leu  Pro  His  Ala  Asp  Trp  Ile  Ile  Ala  Met  Lys  Asp  Gly  Thr
               895                      900                     905

ATT  CAG  AGG  GAG  GGG  ACA  CTC  AAG  GAC  TTC  CAG  AGG  TCT  GAG  TGC  CAG         3028
Ile  Gln  Arg  Glu  Gly  Thr  Leu  Lys  Asp  Phe  Gln  Arg  Ser  Glu  Cys  Gln
          910                      915                     920

CTC  TTT  GAG  CAT  TGG  AAG  ACC  CTC  ATG  AAC  CGG  CAG  GAC  CAA  GAG  CTG         3076
Leu  Phe  Glu  His  Trp  Lys  Thr  Leu  Met  Asn  Arg  Gln  Asp  Gln  Glu  Leu
     925                      930                     935

GAG  AAG  GAG  ACA  GTC  ATG  GAG  AGA  AAA  GCC  CCA  GAG  CCA  TCT  CAG  GGC         3124
Glu  Lys  Glu  Thr  Val  Met  Glu  Arg  Lys  Ala  Pro  Glu  Pro  Ser  Gln  Gly
940                      945                     950                          955

CTG  CCC  CGT  GCC  ATG  TCC  TCA  AGA  GAT  GGC  CTT  CTG  CTG  GAT  GAG  GAT         3172
Leu  Pro  Arg  Ala  Met  Ser  Ser  Arg  Asp  Gly  Leu  Leu  Leu  Asp  Glu  Asp
                    960                     965                          970

GAG  GAG  GAA  GAG  GAG  GCA  GCC  GAG  AGC  GAG  GAA  GAT  GAC  AAC  TTA  TCC         3220
Glu  Glu  Glu  Glu  Glu  Ala  Ala  Glu  Ser  Glu  Glu  Asp  Asp  Asn  Leu  Ser
               975                      980                     985

TCT  GTG  CTG  CAT  CAG  CGA  GCC  AAG  ATC  CCA  TGG  CGA  GCC  TGC  ACC  AAG         3268
Ser  Val  Leu  His  Gln  Arg  Ala  Lys  Ile  Pro  Trp  Arg  Ala  Cys  Thr  Lys
          990                      995                     1000

TAT  TTG  TCC  TCT  GCT  GGC  ATC  CTG  CTC  CTG  TCC  CTG  CTT  GTC  TTC  TCC         3316
Tyr  Leu  Ser  Ser  Ala  Gly  Ile  Leu  Leu  Leu  Ser  Leu  Leu  Val  Phe  Ser
     1005                     1010                    1015

CAG  CTG  CTC  AAG  CAC  ATG  GTC  TTG  GTG  GCC  ATT  GAC  TAC  TGG  CTG  GCC         3364
Gln  Leu  Leu  Lys  His  Met  Val  Leu  Val  Ala  Ile  Asp  Tyr  Trp  Leu  Ala
1020                     1025                    1030                         1035

AAG  TGG  ACG  GAC  AGT  GCC  CTG  GTC  CTG  AGC  CCC  GCC  GCC  AGG  AAC  TGC         3412
Lys  Trp  Thr  Asp  Ser  Ala  Leu  Val  Leu  Ser  Pro  Ala  Ala  Arg  Asn  Cys
                    1040                    1045                         1050

TCC  CTC  AGC  CAG  GAA  TGT  GCC  CTG  GAC  CAA  TCT  GTC  TAT  GCC  ATG  GTA         3460
Ser  Leu  Ser  Gln  Glu  Cys  Ala  Leu  Asp  Gln  Ser  Val  Tyr  Ala  Met  Val
               1055                     1060                    1065

TTC  ACC  GTG  CTC  TGC  AGC  CTG  GGT  ATC  GCG  CTG  TGC  CTT  GTC  ACC  TCT         3508
Phe  Thr  Val  Leu  Cys  Ser  Leu  Gly  Ile  Ala  Leu  Cys  Leu  Val  Thr  Ser
          1070                     1075                    1080

GTC  ACT  GTG  GAG  TGG  ACG  GGA  CTG  AAG  GTG  GCC  AAG  AGG  CTG  CAT  CGC         3556
Val  Thr  Val  Glu  Trp  Thr  Gly  Leu  Lys  Val  Ala  Lys  Arg  Leu  His  Arg
     1085                     1090                    1095

AGC  CTG  CTC  AAC  CGT  ATC  ATC  CTG  GCT  CCC  ATG  AGG  TTC  TTT  GAG  ACC         3604
Ser  Leu  Leu  Asn  Arg  Ile  Ile  Leu  Ala  Pro  Met  Arg  Phe  Phe  Glu  Thr
1100                     1105                    1110                         1115

ACG  CCC  CTG  GGG  AGT  ATC  CTG  AAC  AGA  TTT  TCA  TCT  GAC  TGT  AAC  ACC         3652
Thr  Pro  Leu  Gly  Ser  Ile  Leu  Asn  Arg  Phe  Ser  Ser  Asp  Cys  Asn  Thr
                    1120                    1125                         1130

ATT  GAC  CAG  CAT  ATC  CCG  TCC  ACG  CTG  GAG  TGC  CTG  AGC  AGA  TCC  ACC         3700
Ile  Asp  Gln  His  Ile  Pro  Ser  Thr  Leu  Glu  Cys  Leu  Ser  Arg  Ser  Thr
               1135                     1140                    1145

TTA  CTC  TGT  GTC  TCC  GCC  CTG  GCT  GTC  ATC  TCC  TAC  GTC  ACG  CCT  GTG         3748
Leu  Leu  Cys  Val  Ser  Ala  Leu  Ala  Val  Ile  Ser  Tyr  Val  Thr  Pro  Val
          1150                     1155                    1160

TTC  CTA  GTG  GCC  CTC  TTA  CCC  CTC  GCC  GTC  GTG  TGC  TAC  TTC  ATC  CAG         3796
Phe  Leu  Val  Ala  Leu  Leu  Pro  Leu  Ala  Val  Val  Cys  Tyr  Phe  Ile  Gln
     1165                     1170                    1175

AAG  TAC  TTC  CGA  GTG  GCG  TCC  AGG  GAC  CTG  CAG  CAG  CTG  GAC  GAC  ACA         3844
Lys  Tyr  Phe  Arg  Val  Ala  Ser  Arg  Asp  Leu  Gln  Gln  Leu  Asp  Asp  Thr
1180                     1185                    1190                         1195

ACA  CAG  CTC  CCT  CTG  CTC  TCA  CAC  TTT  GCT  GAA  ACT  GTG  GAA  GGA  CTC         3892
Thr  Gln  Leu  Pro  Leu  Leu  Ser  His  Phe  Ala  Glu  Thr  Val  Glu  Gly  Leu
```

|  |  |  |  |  |  |  |  |  |  |  |  |  |  |  |  |  |
|---|---|---|---|---|---|---|---|---|---|---|---|---|---|---|---|---|
|  |  |  | 1200 |  |  |  |  | 1205 |  |  |  |  | 1210 |  |  |  |
| ACC | ACC | ATC | CGT | GCC | TTC | AGG | TAC | GAG | GCC | CGG | TTC | CAG | CAG | AAG | CTC | 3940 |
| Thr | Thr | Ile | Arg | Ala | Phe | Arg | Tyr | Glu | Ala | Arg | Phe | Gln | Gln | Lys | Leu |  |
|  |  |  | 1215 |  |  |  | 1220 |  |  |  |  |  | 1225 |  |  |  |
| CTA | GAG | TAC | ACC | GAC | TCC | AAC | AAC | ATT | GCC | TCT | CTC | TTC | CTC | ACA | GCA | 3988 |
| Leu | Glu | Tyr | Thr | Asp | Ser | Asn | Asn | Ile | Ala | Ser | Leu | Phe | Leu | Thr | Ala |  |
|  | 1230 |  |  |  |  | 1235 |  |  |  |  | 1240 |  |  |  |  |  |
| GCC | AAC | AGG | TGG | CTG | GAA | GTC | CGC | ATG | GAG | TAC | ATC | GGA | GCA | TGC | GTG | 4036 |
| Ala | Asn | Arg | Trp | Leu | Glu | Val | Arg | Met | Glu | Tyr | Ile | Gly | Ala | Cys | Val |  |
|  | 1245 |  |  |  |  | 1250 |  |  |  |  | 1255 |  |  |  |  |  |
| GTA | CTC | ATC | GCC | GCT | GCC | ACC | TCC | ATC | TCC | AAC | TCC | CTA | CAC | AGG | GAG | 4084 |
| Val | Leu | Ile | Ala | Ala | Ala | Thr | Ser | Ile | Ser | Asn | Ser | Leu | His | Arg | Glu |  |
| 1260 |  |  |  |  | 1265 |  |  |  |  | 1270 |  |  |  |  | 1275 |  |
| CTC | TCA | GCC | GGC | CTA | GTA | GGC | CTG | GGC | CTC | ACC | TAT | GCC | TTG | ATG | GTC | 4132 |
| Leu | Ser | Ala | Gly | Leu | Val | Gly | Leu | Gly | Leu | Thr | Tyr | Ala | Leu | Met | Val |  |
|  |  |  |  | 1280 |  |  |  |  | 1285 |  |  |  |  | 1290 |  |  |
| TCC | AAC | TAC | CTC | AAC | TGG | ATG | GTG | AGG | AAC | CTG | GCA | GAC | ATG | GAG | ATC | 4180 |
| Ser | Asn | Tyr | Leu | Asn | Trp | Met | Val | Arg | Asn | Leu | Ala | Asp | Met | Glu | Ile |  |
|  |  |  | 1295 |  |  |  |  | 1300 |  |  |  |  | 1305 |  |  |  |
| CAA | CTG | GGA | GCT | GTG | AAG | GGT | ATC | CAC | ACA | CTC | CTG | AAA | ACT | GAG | GCA | 4228 |
| Gln | Leu | Gly | Ala | Val | Lys | Gly | Ile | His | Thr | Leu | Leu | Lys | Thr | Glu | Ala |  |
|  | 1310 |  |  |  |  |  | 1315 |  |  |  |  | 1320 |  |  |  |  |
| GAG | AGC | TAT | GAG | GGG | CTC | CTG | GCA | CCA | TCG | CTG | ATC | CCC | AAG | AAC | TGG | 4276 |
| Glu | Ser | Tyr | Glu | Gly | Leu | Leu | Ala | Pro | Ser | Leu | Ile | Pro | Lys | Asn | Trp |  |
| 1325 |  |  |  |  | 1330 |  |  |  |  | 1335 |  |  |  |  |  |  |
| CCA | GAC | CAA | GGG | AAG | ATC | CAA | ATT | CAA | AAC | CTG | AGT | GTA | CGC | TAT | GAC | 4324 |
| Pro | Asp | Gln | Gly | Lys | Ile | Gln | Ile | Gln | Asn | Leu | Ser | Val | Arg | Tyr | Asp |  |
| 1340 |  |  |  |  | 1345 |  |  |  |  | 1350 |  |  |  |  | 1355 |  |
| AGC | TCC | CTG | AAG | CCC | GTG | CTG | AAG | CAC | GTC | AAC | GCC | CTC | ATC | TCC | CCA | 4372 |
| Ser | Ser | Leu | Lys | Pro | Val | Leu | Lys | His | Val | Asn | Ala | Leu | Ile | Ser | Pro |  |
|  |  |  | 1360 |  |  |  |  | 1365 |  |  |  |  | 1370 |  |  |  |
| GGA | CAG | AAG | ATT | GGG | ATC | TGC | GGC | CGC | ACA | GGC | AGT | GGA | AAA | TCC | TCC | 4420 |
| Gly | Gln | Lys | Ile | Gly | Ile | Cys | Gly | Arg | Thr | Gly | Ser | Gly | Lys | Ser | Ser |  |
|  |  |  | 1375 |  |  |  |  | 1380 |  |  |  |  | 1385 |  |  |  |
| TTC | TCT | CTC | GCC | TTT | TTC | CGA | ATG | GTG | GAT | ATG | TTT | GAA | GGG | CGT | ATC | 4468 |
| Phe | Ser | Leu | Ala | Phe | Phe | Arg | Met | Val | Asp | Met | Phe | Glu | Gly | Arg | Ile |  |
|  |  | 1390 |  |  |  |  | 1395 |  |  |  |  | 1400 |  |  |  |  |
| ATC | ATC | GAT | GGC | ATT | GAC | ATC | GCC | AAG | CTG | CCG | CTG | CAC | ACG | CTC | GGC | 4516 |
| Ile | Ile | Asp | Gly | Ile | Asp | Ile | Ala | Lys | Leu | Pro | Leu | His | Thr | Leu | Gly |  |
|  | 1405 |  |  |  |  | 1410 |  |  |  |  | 1415 |  |  |  |  |  |
| TCA | CGC | CTG | TCT | ATC | ATC | CTA | CAG | GAC | CCT | GTT | CTC | TTC | AGT | GGT | ACC | 4564 |
| Ser | Arg | Leu | Ser | Ile | Ile | Leu | Gln | Asp | Pro | Val | Leu | Phe | Ser | Gly | Thr |  |
| 1420 |  |  |  |  | 1425 |  |  |  |  | 1430 |  |  |  |  | 1435 |  |
| ATC | AGA | TTC | AAC | CTG | GAC | CCA | GAG | AAG | AAA | TGC | TCA | GAC | AGC | ACG | CTG | 4612 |
| Ile | Arg | Phe | Asn | Leu | Asp | Pro | Glu | Lys | Lys | Cys | Ser | Asp | Ser | Thr | Leu |  |
|  |  |  |  | 1440 |  |  |  |  | 1445 |  |  |  |  | 1450 |  |  |
| TGG | GAG | GCT | CTG | GAG | ATC | GCT | CAG | CTG | AAG | CTG | GTG | GTG | AAG | GCC | CTG | 4660 |
| Trp | Glu | Ala | Leu | Glu | Ile | Ala | Gln | Leu | Lys | Leu | Val | Val | Lys | Ala | Leu |  |
|  |  |  | 1455 |  |  |  |  | 1460 |  |  |  |  | 1465 |  |  |  |
| CCA | GGA | GGC | CTG | GAT | GCC | ATC | ATC | ACG | GAA | GGA | GGG | GAG | AAT | TTT | AGC | 4708 |
| Pro | Gly | Gly | Leu | Asp | Ala | Ile | Ile | Thr | Glu | Gly | Gly | Glu | Asn | Phe | Ser |  |
|  |  |  | 1470 |  |  |  |  | 1475 |  |  |  |  | 1480 |  |  |  |
| CAG | GGC | CAG | AGG | CAG | CTG | TTC | TGC | CTG | GCC | CGG | GCC | TTT | GTG | AGG | AAG | 4756 |
| Gln | Gly | Gln | Arg | Gln | Leu | Phe | Cys | Leu | Ala | Arg | Ala | Phe | Val | Arg | Lys |  |
|  | 1485 |  |  |  |  | 1490 |  |  |  |  | 1495 |  |  |  |  |  |
| ACC | AGC | ATC | TTC | ATC | ATG | GAT | GAA | GCA | ACT | GCC | TCC | ATC | GAC | ATG | GCT | 4804 |
| Thr | Ser | Ile | Phe | Ile | Met | Asp | Glu | Ala | Thr | Ala | Ser | Ile | Asp | Met | Ala |  |
| 1500 |  |  |  |  | 1505 |  |  |  |  | 1510 |  |  |  |  | 1515 |  |
| ACG | GAA | AAT | ATC | CTC | CAG | AAG | GTG | GTG | ATG | ACA | GCC | TTC | GCA | GAC | CGC | 4852 |
| Thr | Glu | Asn | Ile | Leu | Gln | Lys | Val | Val | Met | Thr | Ala | Phe | Ala | Asp | Arg |  |

-continued

```
                           1520                              1525                              1530
ACC  GTG  GTC  ACC  ATC  GCG  CAC  CGC  GTG  CAC  ACC  ATC  CTG  AGT  GCA  GAC                4900
Thr  Val  Val  Thr  Ile  Ala  His  Arg  Val  His  Thr  Ile  Leu  Ser  Ala  Asp
               1535                    1540                         1545

CTA  GTG  ATG  GTC  CTG  AAG  AGG  GGC  GCG  ATC  CTG  GAG  TTC  GAC  AAG  CCG                4948
Leu  Val  Met  Val  Leu  Lys  Arg  Gly  Ala  Ile  Leu  Glu  Phe  Asp  Lys  Pro
               1550                    1555                         1560

GAA  AAG  CTT  CTC  AGC  CAG  AAG  GAC  AGC  GTC  TTT  GCC  TCC  TTT  GTC  CGC                4996
Glu  Lys  Leu  Leu  Ser  Gln  Lys  Asp  Ser  Val  Phe  Ala  Ser  Phe  Val  Arg
     1565                         1570                    1575

GCG  GAC  AA ATGACCAGCC  AGCGCCAAAG  TGCCACCCCA  CACCTCACCT  GCTTGCCATG                        5054
Ala  Asp
1580

GATTTCTTAC  TGTAAATCAC  TTGTAAATAA  AGAAACTAAT  TCTTTGCTAA  AAAAAA                             5110
```

( 2 ) INFORMATION FOR SEQ ID NO:6:

( i ) SEQUENCE CHARACTERISTICS:
        ( A ) LENGTH: 1581 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Pro  Leu  Ala  Phe  Cys  Gly  Thr  Glu  Asn  His  Ser  Ala  Ala  Tyr  Arg
 1                  5                        10                       15

Val  Asp  Gln  Gly  Val  Leu  Asn  Asn  Gly  Cys  Phe  Val  Asp  Ala  Leu  Asn
                    20                        25                       30

Val  Val  Pro  His  Val  Phe  Leu  Leu  Phe  Ile  Thr  Phe  Pro  Ile  Leu  Phe
               35                        40                       45

Ile  Gly  Trp  Gly  Ser  Gln  Ser  Ser  Lys  Val  His  Ile  His  His  Ser  Thr
          50                        55                       60

Trp  Leu  His  Phe  Pro  Gly  His  Asn  Leu  Arg  Trp  Ile  Leu  Thr  Phe  Ile
 65                       70                       75                            80

Leu  Leu  Phe  Val  Leu  Val  Cys  Glu  Ile  Ala  Glu  Gly  Ile  Leu  Ser  Asp
                    85                        90                       95

Gly  Val  Thr  Glu  Ser  Arg  His  Leu  His  Leu  Tyr  Met  Pro  Ala  Gly  Met
                    100                       105                      110

Ala  Phe  Met  Ala  Ala  Ile  Thr  Ser  Val  Val  Tyr  Tyr  His  Asn  Ile  Glu
               115                       120                      125

Thr  Ser  Asn  Phe  Pro  Lys  Leu  Leu  Ile  Ala  Leu  Leu  Ile  Tyr  Trp  Thr
          130                       135                      140

Leu  Ala  Phe  Ile  Thr  Lys  Thr  Ile  Lys  Phe  Val  Lys  Phe  Tyr  Asp  His
145                       150                      155                           160

Ala  Ile  Gly  Phe  Ser  Gln  Leu  Arg  Phe  Cys  Leu  Thr  Gly  Leu  Leu  Val
                    165                       170                      175

Ile  Leu  Tyr  Gly  Met  Leu  Leu  Leu  Val  Glu  Val  Asn  Val  Ile  Arg  Val
                    180                       185                      190

Arg  Arg  Tyr  Val  Phe  Phe  Lys  Thr  Pro  Arg  Glu  Val  Lys  Pro  Pro  Glu
               195                       200                      205

Asp  Leu  Gln  Asp  Leu  Gly  Val  Arg  Phe  Leu  Gln  Pro  Phe  Val  Asn  Leu
     210                       215                      220

Leu  Ser  Lys  Gly  Thr  Tyr  Trp  Trp  Met  Asn  Ala  Phe  Ile  Lys  Thr  Ala
225                       230                      235                           240

His  Lys  Lys  Pro  Ile  Asp  Leu  Arg  Ala  Ile  Gly  Lys  Leu  Pro  Ile  Ala
                    245                       250                      255
```

```
Met  Arg  Ala  Leu  Thr  Asn  Tyr  Gln  Arg  Leu  Cys  Leu  Ala  Phe  Asp  Ala
               260                 265                      270

Gln  Ala  Arg  Lys  Asp  Thr  Gln  Ser  Gln  Gln  Gly  Ala  Arg  Ala  Ile  Trp
          275                      280                      285

Arg  Ala  Leu  Cys  His  Ala  Phe  Gly  Arg  Arg  Leu  Val  Leu  Ser  Ser  Thr
     290                      295                      300

Phe  Arg  Ile  Leu  Ala  Asp  Leu  Leu  Gly  Phe  Ala  Gly  Pro  Leu  Cys  Ile
305                      310                      315                      320

Phe  Gly  Ile  Val  Asp  His  Leu  Gly  Lys  Glu  Asn  His  Val  Phe  Gln  Pro
                    325                      330                      335

Lys  Thr  Gln  Phe  Leu  Gly  Val  Tyr  Phe  Val  Ser  Ser  Gln  Glu  Phe  Leu
               340                      345                      350

Gly  Asn  Ala  Tyr  Val  Leu  Ala  Val  Leu  Leu  Phe  Leu  Ala  Leu  Leu  Leu
          355                      360                      365

Gln  Arg  Thr  Phe  Leu  Gln  Ala  Ser  Tyr  Tyr  Val  Ala  Ile  Glu  Thr  Gly
     370                      375                      380

Ile  Asn  Leu  Arg  Gly  Ala  Ile  Gln  Thr  Lys  Ile  Tyr  Asn  Lys  Ile  Met
385                      390                      395                      400

His  Leu  Ser  Thr  Ser  Asn  Leu  Ser  Met  Gly  Glu  Met  Thr  Ala  Gly  Gln
                    405                      410                      415

Ile  Cys  Asn  Leu  Val  Ala  Ile  Asp  Thr  Asn  Gln  Leu  Met  Trp  Phe  Phe
               420                      425                      430

Phe  Leu  Cys  Pro  Asn  Leu  Trp  Ala  Met  Pro  Val  Gln  Ile  Ile  Val  Gly
          435                      440                      445

Val  Ile  Leu  Leu  Tyr  Tyr  Ile  Leu  Gly  Val  Ser  Ala  Leu  Ile  Gly  Ala
     450                      455                      460

Ala  Val  Ile  Ile  Leu  Leu  Ala  Pro  Val  Gln  Tyr  Phe  Val  Ala  Thr  Lys
465                      470                      475                      480

Leu  Ser  Gln  Ala  Gln  Arg  Thr  Thr  Leu  Glu  Tyr  Ser  Asn  Glu  Arg  Leu
                    485                      490                      495

Lys  Gln  Thr  Asn  Glu  Met  Leu  Arg  Gly  Ile  Lys  Leu  Leu  Lys  Leu  Tyr
               500                      505                      510

Ala  Trp  Glu  Asn  Ile  Phe  Cys  Ser  Arg  Val  Glu  Lys  Thr  Arg  Arg  Lys
          515                      520                      525

Glu  Met  Thr  Ser  Leu  Arg  Ala  Phe  Ala  Val  Tyr  Thr  Ser  Ile  Ser  Ile
     530                      535                      540

Phe  Met  Asn  Thr  Ala  Ile  Pro  Ile  Ala  Ala  Val  Leu  Ile  Thr  Phe  Val
545                      550                      555                      560

Gly  His  Val  Ser  Phe  Phe  Lys  Glu  Ser  Asp  Phe  Ser  Pro  Ser  Val  Ala
                    565                      570                      575

Phe  Ala  Ser  Leu  Ser  Leu  Phe  His  Ile  Leu  Val  Thr  Pro  Leu  Phe  Leu
               580                      585                      590

Leu  Ser  Ser  Val  Val  Arg  Ser  Thr  Val  Lys  Ala  Leu  Val  Ser  Val  Gln
          595                      600                      605

Lys  Leu  Ser  Glu  Phe  Leu  Ser  Ser  Ala  Glu  Ile  Arg  Glu  Glu  Gln  Cys
     610                      615                      620

Ala  Pro  Arg  Glu  Pro  Ala  Pro  Gln  Gly  Gln  Ala  Gly  Lys  Tyr  Gln  Ala
625                      630                      635                      640

Val  Pro  Leu  Lys  Val  Val  Asn  Arg  Lys  Arg  Pro  Ala  Arg  Glu  Glu  Val
                    645                      650                      655

Arg  Asp  Leu  Leu  Gly  Pro  Leu  Gln  Arg  Leu  Thr  Pro  Ser  Thr  Asp  Gly
               660                      665                      670

Asp  Ala  Asp  Asn  Phe  Cys  Val  Gln  Ile  Ile  Gly  Gly  Phe  Phe  Thr  Trp
          675                      680                      685
```

```
Thr  Pro  Asp  Gly  Ile  Pro  Thr  Leu  Ser  Asn  Ile  Thr  Ile  Arg  Ile  Pro
     690                 695                 700
Arg  Gly  Gln  Leu  Thr  Met  Ile  Val  Gly  Gln  Val  Gly  Cys  Gly  Lys  Ser
705                      710                 715                           720
Ser  Leu  Leu  Leu  Ala  Thr  Leu  Gly  Glu  Met  Gln  Lys  Val  Ser  Gly  Ala
                    725                 730                 735
Val  Phe  Trp  Asn  Ser  Leu  Pro  Asp  Ser  Glu  Gly  Arg  Arg  Pro  Gln  Gln
               740                 745                           750
Pro  Arg  Ala  Gly  Asp  Ser  Gly  Arg  Phe  Gly  Cys  Gln  Glu  Gln  Arg  Pro
          755                 760                      765
Cys  Gly  Tyr  Ala  Ser  Gln  Lys  Pro  Trp  Leu  Leu  Asn  Ala  Thr  Val  Glu
     770                 775                      780
Glu  Asn  Ile  Thr  Phe  Glu  Ser  Pro  Phe  Asn  Lys  Gln  Arg  Tyr  Lys  Met
785                 790                 795                                800
Val  Ile  Glu  Ala  Cys  Ser  Leu  Gln  Pro  Asp  Ile  Asp  Ile  Leu  Pro  His
               805                 810                      815
Gly  Asp  Gln  Thr  Gln  Ile  Gly  Glu  Arg  Gly  Ile  Asn  Leu  Ser  Thr  Gly
               820                 825                      830
Gly  Gln  Arg  Pro  Asp  Gln  Cys  Arg  Pro  Glu  Pro  Ser  Thr  Ser  Thr  Pro
     835                      840                 845
Met  Ile  Val  Phe  Leu  Asp  Asp  Pro  Phe  Ser  Ala  Leu  Asp  Val  His  Leu
     850                 855                 860
Ser  Asp  His  Leu  Met  Gln  Ala  Gly  Ile  Leu  Glu  Leu  Leu  Arg  Asp  Asp
865                      870                 875                           880
Lys  Arg  Thr  Val  Val  Leu  Val  Thr  His  Lys  Leu  Gln  Tyr  Leu  Pro  His
                    885                 890                      895
Ala  Asp  Trp  Ile  Ile  Ala  Met  Lys  Asp  Gly  Thr  Ile  Gln  Arg  Glu  Gly
               900                 905                      910
Thr  Leu  Lys  Asp  Phe  Gln  Arg  Ser  Glu  Cys  Gln  Leu  Phe  Glu  His  Trp
          915                 920                      925
Lys  Thr  Leu  Met  Asn  Arg  Gln  Asp  Gln  Glu  Leu  Glu  Lys  Glu  Thr  Val
     930                      935                 940
Met  Glu  Arg  Lys  Ala  Pro  Glu  Pro  Ser  Gln  Gly  Leu  Pro  Arg  Ala  Met
945                      950                 955                           960
Ser  Ser  Arg  Asp  Gly  Leu  Leu  Leu  Asp  Glu  Asp  Glu  Glu  Glu  Glu  Glu
               965                 970                           975
Ala  Ala  Glu  Ser  Glu  Glu  Asp  Asp  Asn  Leu  Ser  Ser  Val  Leu  His  Gln
               980                 985                      990
Arg  Ala  Lys  Ile  Pro  Trp  Arg  Ala  Cys  Thr  Lys  Tyr  Leu  Ser  Ser  Ala
          995                 1000                     1005
Gly  Ile  Leu  Leu  Leu  Ser  Leu  Leu  Val  Phe  Ser  Gln  Leu  Leu  Lys  His
     1010                1015                1020
Met  Val  Leu  Val  Ala  Ile  Asp  Tyr  Trp  Leu  Ala  Lys  Trp  Thr  Asp  Ser
1025                     1030                1035                          1040
Ala  Leu  Val  Leu  Ser  Pro  Ala  Ala  Arg  Asn  Cys  Ser  Leu  Ser  Gln  Glu
                    1045                1050                     1055
Cys  Ala  Leu  Asp  Gln  Ser  Val  Tyr  Ala  Met  Val  Phe  Thr  Val  Leu  Cys
               1060                1065                     1070
Ser  Leu  Gly  Ile  Ala  Leu  Cys  Leu  Val  Thr  Ser  Val  Thr  Val  Glu  Trp
          1075                1080                     1085
Thr  Gly  Leu  Lys  Val  Ala  Lys  Arg  Leu  His  Arg  Ser  Leu  Leu  Asn  Arg
     1090                1095                     1100
Ile  Ile  Leu  Ala  Pro  Met  Arg  Phe  Phe  Glu  Thr  Thr  Pro  Leu  Gly  Ser
```

-continued

```
               1105                    1110                   1115                    1120
Ile  Leu  Asn  Arg  Phe  Ser  Ser  Asp  Cys  Asn  Thr  Ile  Asp  Gln  His  Ile
                         1125                   1130                   1135
Pro  Ser  Thr  Leu  Glu  Cys  Leu  Ser  Arg  Ser  Thr  Leu  Leu  Cys  Val  Ser
               1140                    1145                          1150
Ala  Leu  Ala  Val  Ile  Ser  Tyr  Val  Thr  Pro  Val  Phe  Leu  Val  Ala  Leu
          1155                         1160                   1165
Leu  Pro  Leu  Ala  Val  Val  Cys  Tyr  Phe  Ile  Gln  Lys  Tyr  Phe  Arg  Val
     1170                    1175                   1180
Ala  Ser  Arg  Asp  Leu  Gln  Gln  Leu  Asp  Asp  Thr  Thr  Gln  Leu  Pro  Leu
1185                    1190                    1195                         1200
Leu  Ser  His  Phe  Ala  Glu  Thr  Val  Glu  Gly  Leu  Thr  Thr  Ile  Arg  Ala
                    1205                    1210                   1215
Phe  Arg  Tyr  Glu  Ala  Arg  Phe  Gln  Gln  Lys  Leu  Leu  Glu  Tyr  Thr  Asp
                         1220                   1225                    1230
Ser  Asn  Asn  Ile  Ala  Ser  Leu  Phe  Leu  Thr  Ala  Ala  Asn  Arg  Trp  Leu
                    1235                   1240                    1245
Glu  Val  Arg  Met  Glu  Tyr  Ile  Gly  Ala  Cys  Val  Val  Leu  Ile  Ala  Ala
                    1250                    1255                   1260
Ala  Thr  Ser  Ile  Ser  Asn  Ser  Leu  His  Arg  Glu  Leu  Ser  Ala  Gly  Leu
1265                         1270                    1275                   1280
Val  Gly  Leu  Gly  Leu  Thr  Tyr  Ala  Leu  Met  Val  Ser  Asn  Tyr  Leu  Asn
                    1285                    1290                   1295
Trp  Met  Val  Arg  Asn  Leu  Ala  Asp  Met  Glu  Ile  Gln  Leu  Gly  Ala  Val
               1300                    1305                   1310
Lys  Gly  Ile  His  Thr  Leu  Leu  Lys  Thr  Glu  Ala  Glu  Ser  Tyr  Glu  Gly
          1315                         1320                   1325
Leu  Leu  Ala  Pro  Ser  Leu  Ile  Pro  Lys  Asn  Trp  Pro  Asp  Gln  Gly  Lys
     1330                    1335                    1340
Ile  Gln  Ile  Gln  Asn  Leu  Ser  Val  Arg  Tyr  Asp  Ser  Ser  Leu  Lys  Pro
1345                    1350                         1355                   1360
Val  Leu  Lys  His  Val  Asn  Ala  Leu  Ile  Ser  Pro  Gly  Gln  Lys  Ile  Gly
                         1365                    1370                   1375
Ile  Cys  Gly  Arg  Thr  Gly  Ser  Gly  Lys  Ser  Ser  Phe  Ser  Leu  Ala  Phe
                    1380                    1385                   1390
Phe  Arg  Met  Val  Asp  Met  Phe  Glu  Gly  Arg  Ile  Ile  Ile  Asp  Gly  Ile
                    1395                    1400                   1405
Asp  Ile  Ala  Lys  Leu  Pro  Leu  His  Thr  Leu  Gly  Ser  Arg  Leu  Ser  Ile
     1410                    1415                         1420
Ile  Leu  Gln  Asp  Pro  Val  Leu  Phe  Ser  Gly  Thr  Ile  Arg  Phe  Asn  Leu
1425                    1430                         1435                   1440
Asp  Pro  Glu  Lys  Lys  Cys  Ser  Asp  Ser  Thr  Leu  Trp  Glu  Ala  Leu  Glu
                         1445                   1450                    1455
Ile  Ala  Gln  Leu  Lys  Leu  Val  Val  Lys  Ala  Leu  Pro  Gly  Gly  Leu  Asp
               1460                    1465                         1470
Ala  Ile  Ile  Thr  Glu  Gly  Gly  Glu  Asn  Phe  Ser  Gln  Gly  Gln  Arg  Gln
          1475                         1480                         1485
Leu  Phe  Cys  Leu  Ala  Arg  Ala  Phe  Val  Arg  Lys  Thr  Ser  Ile  Phe  Ile
     1490                    1495                         1500
Met  Asp  Glu  Ala  Thr  Ala  Ser  Ile  Asp  Met  Ala  Thr  Glu  Asn  Ile  Leu
1505                    1510                         1515                   1520
Gln  Lys  Val  Val  Met  Thr  Ala  Phe  Ala  Asp  Arg  Thr  Val  Val  Thr  Ile
                    1525                    1530                   1535
```

| Ala | His | Arg | Val | His | Thr | Ile | Leu | Ser | Ala | Asp | Leu | Val | Met | Val | Leu |
|-----|-----|-----|-----|-----|-----|-----|-----|-----|-----|-----|-----|-----|-----|-----|-----|
|     |     |     |     | 1540 |     |     |     | 1545 |     |     |     |     | 1550 |     |     |

| Lys | Arg | Gly | Ala | Ile | Leu | Glu | Phe | Asp | Lys | Pro | Glu | Lys | Leu | Leu | Ser |
|-----|-----|-----|-----|-----|-----|-----|-----|-----|-----|-----|-----|-----|-----|-----|-----|
|     |     |     |     | 1555 |     |     |     | 1560 |     |     |     |     | 1565 |     |     |

| Gln | Lys | Asp | Ser | Val | Phe | Ala | Ser | Phe | Val | Arg | Ala | Asp |
|-----|-----|-----|-----|-----|-----|-----|-----|-----|-----|-----|-----|-----|
|     | 1570 |    |     |     |     | 1575 |    |     |     |     | 1580 |    |

( 2 ) INFORMATION FOR SEQ ID NO:7:

( i ) SEQUENCE CHARACTERISTICS:
        ( A ) LENGTH: 4877 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:7:

```
AGCCGAGCCC  GTGCGCGCGC  CGCCATGCCC  TTGGCCTTCT  GCGGTACCGA  GAACCACTCG      60
GCCGCCTACC  GGGTGGACCA  GGGCGTCCTC  AACAACGGCT  GCTTCGTGGA  CGCGCTCAAC     120
GTGGTGCCGC  ACGTTTTCCT  GCTCTTCATC  ACCTTCCCCA  TCCTCTTCAT  CGGATGGGGC     180
AGCCAGAGCT  CCAAGGTGCA  CATCCACCAC  AGCACCTGGC  TGCACTTTCC  AGGGCACAAC     240
CTGCGCTGGA  TCCTTACCTT  CATTTTGCTC  TTCGTCCTTG  TGTGTGAGAT  CGCTGAGGGC     300
ATCCTGTCTG  ATGGGGTGAC  AGAATCCCGC  CACCTCCACC  TGTACATGCC  AGCCGGGATG     360
GCGTTCATGG  CTGCCATCAC  CTCTGTAGTC  TACTATCATA  ACATCGAGAC  CTCCAACTTC     420
CCCAAGCTTT  TGATCGCTCT  GCTCATCTAT  TGGACCCTGG  CCTTCATCAC  GAAGACCATC     480
AAGTTTGTCA  AGTTCTATGA  CCACGCCATC  GGCTTCTCCC  AGCTGCGCTT  CTGCCTCACG     540
GGGCTTCTGG  TGATCCTGTA  TGGGATGTTG  CTGCTTGTGG  AGGTCAACGT  CATCAGAGTG     600
AGGAGGTACA  TCTTCTTCAA  GACGCCACGG  GAGGTGAAGC  CCCCTGAGGA  CCTGCAGGAC     660
CTGGGTGTGC  GCTTTCTGCA  GCCCTTCGTT  AACCTGCTGT  CAAAGGGGAC  CTATTGGTGG     720
ATGAATGCCT  TCATCAAGAC  GGCCCACAAG  AAGCCCATCG  ACCTGCGGGC  CATCGCGAAG     780
CTGCCCATCG  CCATGAGAGC  CCTCACCAAC  TATCAGCGCC  TCTGCGTGGC  CTTCGATGCT     840
CAGGCGCGGA  AGGACACACA  GAGCCCACAG  GGTGCCCGGG  CCATCTGGAG  GGCTCTATGC     900
CATGCCTTTG  GGAGACGCCT  GATCCTCAGC  AGCACATTCC  GCATCCTGGC  TGACCTGTTG     960
GGCTTCGCTG  GACCACTCTG  CATCTTTGGG  ATCGTGGACC  ACCTGGGGAA  GGAGAACCAC    1020
GTCTTCCAGC  CCAAGACACA  GTTTCTCGGG  GTTTACTTCG  TCTCTTCTCA  AGAGTTCCTT    1080
GGCAATGCCT  ACGTCTTGGC  CGTGCTTCTG  TTCCTTGCCC  TGCTACTGCA  AAGGACATTC    1140
CTGCAAGCCT  CATACTACGT  CGCCATTGAA  ACTGGAATTA  ACCTGAGAGG  AGCAATCCAG    1200
ACCAAGATTT  ACAATAAAAT  CATGCACATG  TCCACCTCCA  ACCTGTCAAT  GGGGGAAATG    1260
ACTGCTGGGC  AGATCTGCAA  CCTGGTGGCC  ATCGACACAA  CCAGCTCAT  GTGGTTCTTC    1320
TTTCTGTGCC  CAAACCTCTG  GACGATGCCA  GTACAGATCA  TTGTGGGCGT  GATCCTTCTC    1380
TACTACATCC  TTGGGGTCAG  TGCCTTGATT  GGAGCAGCTG  TCATCATTCT  GCTGGCTCCT    1440
GTACAGTACT  TTGTGGCCAC  CAAGCTCTCC  CAGGCACAGC  GGACGACCTT  GGAGCACTCC    1500
AACGAGAGGC  TGAAGCAGAC  CAACGAGATG  CTCCGGGGCA  TGAAGCTGCT  CAAACTGTAT    1560
GCGTGGGAGA  GCATCTTCTG  CTCCAGGGTG  GAGGTGACTC  GCAGGAAGGA  GATGACCAGC    1620
```

| | | | | | | |
|---|---|---|---|---|---|---|
| CTGAGGGCGT | TTGCTGTCTA | CACTTCCATC | TCCATCTTCA | TGAACACAGC | CATCCCCATT | 1680 |
| GCTGCCGTCC | TCATCACCTT | CGTGGGCCAC | GTCAGCTTCT | TCAAAGAGTC | GGACTTGTCA | 1740 |
| CCCTCGGTGG | CCTTTGCCTC | CCTCTCTCTC | TTCCACATCC | TGGTCACTCC | ACTGTTCCTG | 1800 |
| CTGTCTAGCG | TGGTTCGGTC | CACTGTCAAA | GCCCTGGTGA | GCGTGCAAAA | ACTGAGCGAG | 1860 |
| TTCCTGTCTA | GTGCAGAGAT | CCGTGAGGAG | CAGTGTGCCC | CCGAGAGCC | TGCACCCCAA | 1920 |
| GGCCAAGCCG | GCAAGTACCA | GGCAGTGCCC | CTCAAGGTTG | TGAACCGCAA | ACGCCCAGCC | 1980 |
| CGGGAAGAGG | TCCGGGACCT | CCTGGGCCCA | CTGCAGAGGC | TGGCCCCTAG | CATGGACGGG | 2040 |
| GATGCTGACA | ACTTCTGTGT | CCAGATCATC | GGAGGCTTCT | TCACCTGGAC | CCCTGATGGA | 2100 |
| ATCCCCACTC | TGTCCAACAT | CACCATCCGT | ATTCCCCGAG | GTCAGCTAAC | CATGATTGTG | 2160 |
| GGGCAGGTGG | GCTGCGGCAA | GTCCTCGCTC | CTCCTCGCCA | CCCTGGGGGA | GATGCAGAAG | 2220 |
| GTGTCGGGGG | CCGTCTTCTG | GAACAGCAAC | CTTCCGGACA | GCGAGGGGAG | AGGACCCCAG | 2280 |
| CAGCCCAGAG | CGGGAGACAG | CAGCTGGCTC | GGATATCAGG | AGCAGAGGCC | CCGTGGCTAC | 2340 |
| GCATCTCAGA | AACCATGGCT | GCTAAACGCC | ACCGTGGAAG | AGAACATCAC | CTTCGAGAGT | 2400 |
| CCCTTCAATC | CGCAGCGGTA | CAAGATGGTC | ATCGAAGCCT | GCTCCCTGCA | GCCGGACATA | 2460 |
| GACATCCTGC | CCCACGGAGA | CCAGACTCAG | ATTGGGGAAC | GGGGCATCAA | CCTGTCTGGT | 2520 |
| GGTCAGCGTC | CAGATCAGTG | TGGTCCAGAG | CCCTCTACCA | GCAGACCAAT | GTTCGTCTTC | 2580 |
| TTGGATGACC | CCTTCTCAGC | TTTGGATGTC | CATCTGAGTG | ACCACTGAT | GCAGGCCGGC | 2640 |
| ATCCTTGAGC | TGCTCCGGGA | TGACAAGAGG | ACAGTGGTCT | TGGTGACCCA | CAAGCTACAG | 2700 |
| TATCTGCCTC | ATGCAGACTG | GATCATTGCC | ATGAAGGATG | GGACCATTCA | GAGGGAAGGG | 2760 |
| ACGCTCAAGG | ACTTCCAGAG | GTCCGAGTGC | CAGCTCTTTG | AGCACTGGAA | GACCCTCATG | 2820 |
| AACCGGCAGG | ACCAAGAGCT | GGAGAAGGAG | ACAGTCATGG | AGAGGAAAGC | CTCAGAGCCA | 2880 |
| TCTCAGGGCC | TGCCCCGTGC | CATGTCCTCC | AGAGACGGCC | TTCTGCTGGA | TGAGGAAGAG | 2940 |
| GAGGAAGAGG | AGGCAGCCGA | AAGCGAGGAA | GATGACAACT | TATCTTCAGT | GCTGCATCAG | 3000 |
| CGAGCTAAGA | TCCCCTGGCG | AGCCTGCACT | AAGTATCTGT | CCTCTGCTGG | CATTCTGCTC | 3060 |
| CTGTCCCTGC | TTGTCTTCTC | CCAGCTGCTC | AAGCACATGG | TCTTGGTGGC | CATTGATTAT | 3120 |
| TGGCTGGCCA | AGTGGACGGA | CAGTGCCCTG | GTCCTGAGCC | CCGCTGCCAG | GAACTGTTCG | 3180 |
| CTCAGCCAGG | AATGTGACCT | GGACCAGTCT | GTCTATGCCA | TGGTATTCAC | CTTGCTCTGC | 3240 |
| AGCCTGGGTA | TCGTGCTGTG | CCTGGTCACC | TCTGTCACTG | TGGAGTGGAC | GGGACTGAAG | 3300 |
| GTGGCCAAGA | GGCTACACCG | CAGCCTGCTC | AACCGCATCA | TCCTGGCCCC | CATGAGGTTC | 3360 |
| TTTGAGACCA | CACCCCTCGG | GAGTATCCTG | AACAGATTTT | CATCCGACTG | TAACACCATT | 3420 |
| GACCAGCACA | TCCCATCCAC | GCTGGAGTGT | CTGAGCCGGT | CCACCCTGCT | GTGTGTCTCC | 3480 |
| GCCCTGACTG | TCATCTCCTA | TGTCACACCC | GTGTTCCTCG | TGGCCCTCTT | ACCCCTAGCT | 3540 |
| GTTGTGTGCT | ACTTCATTCA | GAAGTACTTC | CGAGTGGCAT | CCAGGGACCT | GCAGCAGCTG | 3600 |
| GACGACACGA | CGCAGCTCCC | GCTCGTCTCA | CACTTTGCTG | AAACTGTGGA | GGGACTCACC | 3660 |
| ACCATCCGTG | CCTTCAGGTA | CGAGGCCCGG | TTCCAGCAGA | AGCTTCTAGA | ATATACCGAC | 3720 |
| TCCAACAACA | TCGCCTCCCT | CTTCCTCACG | GCAGCCAACA | GATGGCTGGA | AGTCTGCATG | 3780 |
| GAGTACATCG | GAGCGTGCGT | GGTACTCATT | GCGGCTGCCA | CCTCCATCTC | CAACTCCCTG | 3840 |
| CACAGGGAAC | TTTCTGCTGG | CCTGGTGGGC | CTGGGCCTCA | CCTATGCCTT | GATGGTCTCC | 3900 |
| AACTACCTCA | ACTGGATGGT | GAGGAACCTG | GCGGACATGG | AGATCCAGCT | GGGGGCTGTG | 3960 |
| AAGAGGATCC | ACGCACTCCT | GAAAACCGAG | GCGGAGAGCT | ATGAGGGGCT | CCTGGCGCCG | 4020 |

-continued

| | | | | | | |
|---|---|---|---|---|---|---|
| TCGTTGATCC | CCAAGAACTG | GCCAGACCAA | GGGAAGATCC | AAATTCAGAA | CCTGAGCGTG | 4080 |
| CGCTATGACA | GCTCCCTGAA | GCCAGTGCTG | AAGCATGTCA | ACACCCTCAT | CTCCCCGGGG | 4140 |
| CAGAAGATCG | GGATCTGCGG | CCGCACAGGC | AGCGGAAGT | CCTCCTTCTC | CCTGGCCTTT | 4200 |
| TTCCGAATGG | TGGACATGTT | TGAAGGACGC | ATCATCATTG | ATGGCATCGA | CATCGCCAAG | 4260 |
| CTGCCACTTC | ACACGCTGCG | CTCACGCCTG | TCCATCATCC | TACAGGACCC | CGTCCTCTTC | 4320 |
| AGCGGCACGA | TCAGATTCAA | CCTGGACCCC | GAGAAGAAAT | GCTCAGACAG | CACACTGTGG | 4380 |
| GAGGCCCTGG | AGATCGCCCA | GCTGAAGCTG | GTAGTGAAGG | CACTGCCAGG | AGGCCTAGAT | 4440 |
| GCCATCATCA | CAGAAGGAGG | GGAGAATTTT | AGCCAGGGCC | AGAGGCAGCT | GTTCTGCCTG | 4500 |
| GCCCGGGCCT | TCGTGAGGAA | GACCAGCATC | TTCATCATGG | ATGAAGCAAC | CGCCTCCATC | 4560 |
| GACATGGCTA | CGGAGAACAT | CCTCCAGAAG | GTGGTGATGA | CAGCCTTCGC | AGACCGCACG | 4620 |
| GTGGTCACCA | TCGCGCATCG | TGTGCACACC | ATCCTGAGTG | CAGACCTGGT | GATGGTCCTC | 4680 |
| AAGAGGGGTG | CTATCCTGGA | GTTTGACAAG | CCAGAGACGC | TCCTCAGCCA | GAAGGACAGC | 4740 |
| GTGTTCGCCT | CCTTTGTCCG | TGCGGACAAG | TGACTTACCG | GAGCCAAAGT | GCCACCCCGC | 4800 |
| GCCTCGCTTG | CTTGCCTAGG | ATTTCTAACT | GCAAATCACT | TGTAAATAAA | TTAATTCTTT | 4860 |
| GCTAAAAAAA | AAAAAAA | | | | | 4877 |

( 2 ) INFORMATION FOR SEQ ID NO:8:

( i ) SEQUENCE CHARACTERISTICS:
        ( A ) LENGTH: 4877 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 25..4770

( x i ) SEQUENCE DESCRIPTION: SEQ ID NO:8:

| | | | | | | | | | | | | | |
|---|---|---|---|---|---|---|---|---|---|---|---|---|---|
| AGCCGAGCCC | GTGCGCGCGC | CGCC | ATG | CCC | TTG | GCC | TTC | TGC | GGT | ACC | GAG | | 51 |
| | | | Met | Pro | Leu | Ala | Phe | Cys | Gly | Thr | Glu | | |
| | | | 1 | | | | 5 | | | | | | |
| AAC | CAC | TCG | GCC | GCC | TAC | CGG | GTG | GAC | CAG | GGC | GTC | CTC | AAC | AAC | GGC | 99 |
| Asn | His | Ser | Ala | Ala | Tyr | Arg | Val | Asp | Gln | Gly | Val | Leu | Asn | Asn | Gly | |
| 10 | | | | | 15 | | | | 20 | | | | | | 25 | |
| TGC | TTC | GTG | GAC | GCG | CTC | AAC | GTG | GTG | CCG | CAC | GTT | TTC | CTG | CTC | TTC | 147 |
| Cys | Phe | Val | Asp | Ala | Leu | Asn | Val | Val | Pro | His | Val | Phe | Leu | Leu | Phe | |
| | | | | 30 | | | | | 35 | | | | | 40 | | |
| ATC | ACC | TTC | CCC | ATC | CTC | TTC | ATC | GGA | TGG | GGC | AGC | CAG | AGC | TCC | AAG | 195 |
| Ile | Thr | Phe | Pro | Ile | Leu | Phe | Ile | Gly | Trp | Gly | Ser | Gln | Ser | Ser | Lys | |
| | | | 45 | | | | | 50 | | | | | 55 | | | |
| GTG | CAC | ATC | CAC | CAC | AGC | ACC | TGG | CTG | CAC | TTT | CCA | GGG | CAC | AAC | CTG | 243 |
| Val | His | Ile | His | His | Ser | Thr | Trp | Leu | His | Phe | Pro | Gly | His | Asn | Leu | |
| | | | 60 | | | | 65 | | | | | 70 | | | | |
| CGC | TGG | ATC | CTT | ACC | TTC | ATT | TTG | CTC | TTC | GTC | CTT | GTG | TGT | GAG | ATC | 291 |
| Arg | Trp | Ile | Leu | Thr | Phe | Ile | Leu | Leu | Phe | Val | Leu | Val | Cys | Glu | Ile | |
| | 75 | | | | | 80 | | | | | 85 | | | | | |
| GCT | GAG | GGC | ATC | CTG | TCT | GAT | GGG | GTG | ACA | GAA | TCC | CGC | CAC | CTC | CAC | 339 |
| Ala | Glu | Gly | Ile | Leu | Ser | Asp | Gly | Val | Thr | Glu | Ser | Arg | His | Leu | His | |
| 90 | | | | | 95 | | | | 100 | | | | | 105 | | |
| CTG | TAC | ATG | CCA | GCC | GGG | ATG | GCG | TTC | ATG | GCT | GCC | ATC | ACC | TCT | GTA | 387 |

-continued

| | | | | | | | | | | | | | | | | |
|---|---|---|---|---|---|---|---|---|---|---|---|---|---|---|---|---|
| Leu | Tyr | Met | Pro | Ala | Gly | Met | Ala | Phe | Met | Ala | Ala | Ile | Thr | Ser | Val | |
| | | | 110 | | | | 115 | | | | | | | 120 | | |

| GTC | TAC | TAT | CAT | AAC | ATC | GAG | ACC | TCC | AAC | TTC | CCC | AAG | CTT | TTG | ATC | 435 |
|---|---|---|---|---|---|---|---|---|---|---|---|---|---|---|---|---|
| Val | Tyr | Tyr | His | Asn | Ile | Glu | Thr | Ser | Asn | Phe | Pro | Lys | Leu | Leu | Ile | |
| | | | 125 | | | | 130 | | | | | | 135 | | | |

| GCT | CTG | CTC | ATC | TAT | TGG | ACC | CTG | GCC | TTC | ATC | ACG | AAG | ACC | ATC | AAG | 483 |
|---|---|---|---|---|---|---|---|---|---|---|---|---|---|---|---|---|
| Ala | Leu | Leu | Ile | Tyr | Trp | Thr | Leu | Ala | Phe | Ile | Thr | Lys | Thr | Ile | Lys | |
| | | 140 | | | | | 145 | | | | | | 150 | | | |

| TTT | GTC | AAG | TTC | TAT | GAC | CAC | GCC | ATC | GGC | TTC | TCC | CAG | CTG | CGC | TTC | 531 |
|---|---|---|---|---|---|---|---|---|---|---|---|---|---|---|---|---|
| Phe | Val | Lys | Phe | Tyr | Asp | His | Ala | Ile | Gly | Phe | Ser | Gln | Leu | Arg | Phe | |
| | 155 | | | | | 160 | | | | | 165 | | | | | |

| TGC | CTC | ACG | GGG | CTT | CTG | GTG | ATC | CTG | TAT | GGG | ATG | TTG | CTG | CTT | GTG | 579 |
|---|---|---|---|---|---|---|---|---|---|---|---|---|---|---|---|---|
| Cys | Leu | Thr | Gly | Leu | Leu | Val | Ile | Leu | Tyr | Gly | Met | Leu | Leu | Leu | Val | |
| 170 | | | | | 175 | | | | | 180 | | | | | 185 | |

| GAG | GTC | AAC | GTC | ATC | AGA | GTG | AGG | AGG | TAC | ATC | TTC | TTC | AAG | ACG | CCA | 627 |
|---|---|---|---|---|---|---|---|---|---|---|---|---|---|---|---|---|
| Glu | Val | Asn | Val | Ile | Arg | Val | Arg | Arg | Tyr | Ile | Phe | Phe | Lys | Thr | Pro | |
| | | | | 190 | | | | | 195 | | | | | | 200 | |

| CGG | GAG | GTG | AAG | CCC | CCT | GAG | GAC | CTG | CAG | GAC | CTG | GGT | GTG | CGC | TTT | 675 |
|---|---|---|---|---|---|---|---|---|---|---|---|---|---|---|---|---|
| Arg | Glu | Val | Lys | Pro | Pro | Glu | Asp | Leu | Gln | Asp | Leu | Gly | Val | Arg | Phe | |
| | | | 205 | | | | | 210 | | | | | 215 | | | |

| CTG | CAG | CCC | TTC | GTT | AAC | CTG | CTG | TCA | AAG | GGG | ACC | TAT | TGG | TGG | ATG | 723 |
|---|---|---|---|---|---|---|---|---|---|---|---|---|---|---|---|---|
| Leu | Gln | Pro | Phe | Val | Asn | Leu | Leu | Ser | Lys | Gly | Thr | Tyr | Trp | Trp | Met | |
| | | 220 | | | | | 225 | | | | | 230 | | | | |

| AAT | GCC | TTC | ATC | AAG | ACG | GCC | CAC | AAG | AAG | CCC | ATC | GAC | CTG | CGG | GCC | 771 |
|---|---|---|---|---|---|---|---|---|---|---|---|---|---|---|---|---|
| Asn | Ala | Phe | Ile | Lys | Thr | Ala | His | Lys | Lys | Pro | Ile | Asp | Leu | Arg | Ala | |
| | 235 | | | | | 240 | | | | | 245 | | | | | |

| ATC | GCG | AAG | CTG | CCC | ATC | GCC | ATG | AGA | GCC | CTC | ACC | AAC | TAT | CAG | CGC | 819 |
|---|---|---|---|---|---|---|---|---|---|---|---|---|---|---|---|---|
| Ile | Ala | Lys | Leu | Pro | Ile | Ala | Met | Arg | Ala | Leu | Thr | Asn | Tyr | Gln | Arg | |
| 250 | | | | | 255 | | | | | 260 | | | | | 265 | |

| CTC | TGC | GTG | GCC | TTC | GAT | GCT | CAG | GCG | CGG | AAG | GAC | ACA | CAG | AGC | CCA | 867 |
|---|---|---|---|---|---|---|---|---|---|---|---|---|---|---|---|---|
| Leu | Cys | Val | Ala | Phe | Asp | Ala | Gln | Ala | Arg | Lys | Asp | Thr | Gln | Ser | Pro | |
| | | | | 270 | | | | | 275 | | | | | 280 | | |

| CAG | GGT | GCC | CGG | GCC | ATC | TGG | AGG | GCT | CTA | TGC | CAT | GCC | TTT | GGG | AGA | 915 |
|---|---|---|---|---|---|---|---|---|---|---|---|---|---|---|---|---|
| Gln | Gly | Ala | Arg | Ala | Ile | Trp | Arg | Ala | Leu | Cys | His | Ala | Phe | Gly | Arg | |
| | | | 285 | | | | | 290 | | | | | 295 | | | |

| CGC | CTG | ATC | CTC | AGC | AGC | ACA | TTC | CGC | ATC | CTG | GCT | GAC | CTG | TTG | GGC | 963 |
|---|---|---|---|---|---|---|---|---|---|---|---|---|---|---|---|---|
| Arg | Leu | Ile | Leu | Ser | Ser | Thr | Phe | Arg | Ile | Leu | Ala | Asp | Leu | Leu | Gly | |
| | | 300 | | | | | 305 | | | | | 310 | | | | |

| TTC | GCT | GGA | CCA | CTC | TGC | ATC | TTT | GGG | ATC | GTG | GAC | CAC | CTG | GGG | AAG | 1011 |
|---|---|---|---|---|---|---|---|---|---|---|---|---|---|---|---|---|
| Phe | Ala | Gly | Pro | Leu | Cys | Ile | Phe | Gly | Ile | Val | Asp | His | Leu | Gly | Lys | |
| | 315 | | | | | 320 | | | | | 325 | | | | | |

| GAG | AAC | CAC | GTC | TTC | CAG | CCC | AAG | ACA | CAG | TTT | CTC | GGG | GTT | TAC | TTC | 1059 |
|---|---|---|---|---|---|---|---|---|---|---|---|---|---|---|---|---|
| Glu | Asn | His | Val | Phe | Gln | Pro | Lys | Thr | Gln | Phe | Leu | Gly | Val | Tyr | Phe | |
| 330 | | | | | 335 | | | | | 340 | | | | | 345 | |

| GTC | TCT | TCT | CAA | GAG | TTC | CTT | GGC | AAT | GCC | TAC | GTC | TTG | GCC | GTG | CTT | 1107 |
|---|---|---|---|---|---|---|---|---|---|---|---|---|---|---|---|---|
| Val | Ser | Ser | Gln | Glu | Phe | Leu | Gly | Asn | Ala | Tyr | Val | Leu | Ala | Val | Leu | |
| | | | | 350 | | | | | 355 | | | | | 360 | | |

| CTG | TTC | CTT | GCC | CTG | CTA | CTG | CAA | AGG | ACA | TTC | CTG | CAA | GCC | TCA | TAC | 1155 |
|---|---|---|---|---|---|---|---|---|---|---|---|---|---|---|---|---|
| Leu | Phe | Leu | Ala | Leu | Leu | Leu | Gln | Arg | Thr | Phe | Leu | Gln | Ala | Ser | Tyr | |
| | | | 365 | | | | | 370 | | | | | 375 | | | |

| TAC | GTC | GCC | ATT | GAA | ACT | GGA | ATT | AAC | CTG | AGA | GGA | GCA | ATC | CAG | ACC | 1203 |
|---|---|---|---|---|---|---|---|---|---|---|---|---|---|---|---|---|
| Tyr | Val | Ala | Ile | Glu | Thr | Gly | Ile | Asn | Leu | Arg | Gly | Ala | Ile | Gln | Thr | |
| | | 380 | | | | | 385 | | | | | 390 | | | | |

| AAG | ATT | TAC | AAT | AAA | ATC | ATG | CAC | ATG | TCC | ACC | TCC | AAC | CTG | TCA | ATG | 1251 |
|---|---|---|---|---|---|---|---|---|---|---|---|---|---|---|---|---|
| Lys | Ile | Tyr | Asn | Lys | Ile | Met | His | Met | Ser | Thr | Ser | Asn | Leu | Ser | Met | |
| | 395 | | | | | 400 | | | | | 405 | | | | | |

| GGG | GAA | ATG | ACT | GCT | GGG | CAG | ATC | TGC | AAC | CTG | GTG | GCC | ATC | GAC | ACA | 1299 |
|---|---|---|---|---|---|---|---|---|---|---|---|---|---|---|---|---|
| Gly | Glu | Met | Thr | Ala | Gly | Gln | Ile | Cys | Asn | Leu | Val | Ala | Ile | Asp | Thr | |
| 410 | | | | 415 | | | | | 420 | | | | | 425 | | |

| AAC | CAG | CTC | ATG | TGG | TTC | TTC | TTT | CTG | TGC | CCA | AAC | CTC | TGG | ACG | ATG | 1347 |

|   |   |   |   |   |   |   |   |   |   |   |   |   |   |   |   |   |
|---|---|---|---|---|---|---|---|---|---|---|---|---|---|---|---|---|
| Asn | Gln | Leu | Met | Trp<br>430 | Phe | Phe | Phe | Leu | Cys<br>435 | Pro | Asn | Leu | Trp | Thr<br>440 | Met | |
| CCA<br>Pro | GTA<br>Val | CAG<br>Gln | ATC<br>Ile<br>445 | ATT<br>Ile | GTG<br>Val | GGC<br>Gly | GTG<br>Val | ATC<br>Ile<br>450 | CTT<br>Leu | CTC<br>Leu | TAC<br>Tyr | TAC<br>Tyr | ATC<br>Ile<br>455 | CTT<br>Leu | GGG<br>Gly | 1395 |
| GTC<br>Val | AGT<br>Ser | GCC<br>Ala<br>460 | TTG<br>Leu | ATT<br>Ile | GGA<br>Gly | GCA<br>Ala | GCT<br>Ala<br>465 | GTC<br>Val | ATC<br>Ile | ATT<br>Ile | CTG<br>Leu | CTG<br>Leu<br>470 | GCT<br>Ala | CCT<br>Pro | GTA<br>Val | 1443 |
| CAG<br>Gln | TAC<br>Tyr<br>475 | TTT<br>Phe | GTG<br>Val | GCC<br>Ala | ACC<br>Thr | AAG<br>Lys<br>480 | CTC<br>Leu | TCC<br>Ser | CAG<br>Gln | GCA<br>Ala | CAG<br>Gln<br>485 | CGG<br>Arg | ACG<br>Thr | ACC<br>Thr | TTG<br>Leu | 1491 |
| GAG<br>Glu<br>490 | CAC<br>His | TCC<br>Ser | AAC<br>Asn | GAG<br>Glu | AGG<br>Arg<br>495 | CTG<br>Leu | AAG<br>Lys | CAG<br>Gln | ACC<br>Thr | AAC<br>Asn<br>500 | GAG<br>Glu | ATG<br>Met | CTC<br>Leu | CGG<br>Arg | GGC<br>Gly<br>505 | 1539 |
| ATG<br>Met | AAG<br>Lys | CTG<br>Leu | CTC<br>Leu | AAA<br>Lys<br>510 | CTG<br>Leu | TAT<br>Tyr | GCG<br>Ala | TGG<br>Trp | GAG<br>Glu<br>515 | AGC<br>Ser | ATC<br>Ile | TTC<br>Phe | TGC<br>Cys | TCC<br>Ser<br>520 | AGG<br>Arg | 1587 |
| GTG<br>Val | GAG<br>Glu | GTG<br>Val | ACT<br>Thr<br>525 | CGC<br>Arg | AGG<br>Arg | AAG<br>Lys | GAG<br>Glu | ATG<br>Met<br>530 | ACC<br>Thr | AGC<br>Ser | CTG<br>Leu | AGG<br>Arg | GCG<br>Ala<br>535 | TTT<br>Phe | GCT<br>Ala | 1635 |
| GTC<br>Val | TAC<br>Tyr | ACT<br>Thr<br>540 | TCC<br>Ser | ATC<br>Ile | TCC<br>Ser | ATC<br>Ile | TTC<br>Phe<br>545 | ATG<br>Met | AAC<br>Asn | ACA<br>Thr | GCC<br>Ala | ATC<br>Ile<br>550 | CCC<br>Pro | ATT<br>Ile | GCT<br>Ala | 1683 |
| GCC<br>Ala | GTC<br>Val<br>555 | CTC<br>Leu | ATC<br>Ile | ACC<br>Thr | TTC<br>Phe | GTG<br>Val<br>560 | GGC<br>Gly | CAC<br>His | GTC<br>Val | AGC<br>Ser | TTC<br>Phe<br>565 | TTC<br>Phe | AAA<br>Lys | GAG<br>Glu | TCG<br>Ser | 1731 |
| GAC<br>Asp<br>570 | TTG<br>Leu | TCA<br>Ser | CCC<br>Pro | TCG<br>Ser | GTG<br>Val<br>575 | GCC<br>Ala | TTT<br>Phe | GCC<br>Ala | TCC<br>Ser | CTC<br>Leu<br>580 | TCT<br>Ser | CTC<br>Leu | TTC<br>Phe | CAC<br>His | ATC<br>Ile<br>585 | 1779 |
| CTG<br>Leu | GTC<br>Val | ACT<br>Thr | CCA<br>Pro | CTG<br>Leu<br>590 | TTC<br>Phe | CTG<br>Leu | CTG<br>Leu | TCT<br>Ser | AGC<br>Ser<br>595 | GTG<br>Val | GTT<br>Val | CGG<br>Arg | TCC<br>Ser | ACT<br>Thr<br>600 | GTC<br>Val | 1827 |
| AAA<br>Lys | GCC<br>Ala | CTG<br>Leu | GTG<br>Val<br>605 | AGC<br>Ser | GTG<br>Val | CAA<br>Gln | AAA<br>Lys | CTG<br>Leu<br>610 | AGC<br>Ser | GAG<br>Glu | TTC<br>Phe | CTG<br>Leu | TCT<br>Ser<br>615 | AGT<br>Ser | GCA<br>Ala | 1875 |
| GAG<br>Glu | ATC<br>Ile | CGT<br>Arg<br>620 | GAG<br>Glu | GAG<br>Glu | CAG<br>Gln | TGT<br>Cys | GCC<br>Ala<br>625 | CCC<br>Pro | CGA<br>Arg | GAG<br>Glu | CCT<br>Pro | GCA<br>Ala<br>630 | CCC<br>Pro | CAA<br>Gln | GGC<br>Gly | 1923 |
| CAA<br>Gln | GCC<br>Ala<br>635 | GGC<br>Gly | AAG<br>Lys | TAC<br>Tyr | CAG<br>Gln<br>640 | GCA<br>Ala | GTG<br>Val | CCC<br>Pro | CTC<br>Leu | AAG<br>Lys<br>645 | GTT<br>Val | GTG<br>Val | AAC<br>Asn | CGC<br>Arg | AAA<br>Lys | 1971 |
| CGC<br>Arg<br>650 | CCA<br>Pro | GCC<br>Ala | CGG<br>Arg | GAA<br>Glu | GAG<br>Glu<br>655 | GTC<br>Val | CGG<br>Arg | GAC<br>Asp | CTC<br>Leu | CTG<br>Leu<br>660 | GGC<br>Gly | CCA<br>Pro | CTG<br>Leu | CAG<br>Gln | AGG<br>Arg<br>665 | 2019 |
| CTG<br>Leu | GCC<br>Ala | CCT<br>Pro | AGC<br>Ser | ATG<br>Met<br>670 | GAC<br>Asp | GGG<br>Gly | GAT<br>Asp | GCT<br>Ala | GAC<br>Asp<br>675 | AAC<br>Asn | TTC<br>Phe | TGT<br>Cys | GTC<br>Val | CAG<br>Gln<br>680 | ATC<br>Ile | 2067 |
| ATC<br>Ile | GGA<br>Gly | GGC<br>Gly | TTC<br>Phe<br>685 | TTC<br>Phe | ACC<br>Thr | TGG<br>Trp | ACC<br>Thr | CCT<br>Pro<br>690 | GAT<br>Asp | GGA<br>Gly | ATC<br>Ile | CCC<br>Pro | ACT<br>Thr<br>695 | CTG<br>Leu | TCC<br>Ser | 2115 |
| AAC<br>Asn | ATC<br>Ile | ACC<br>Thr<br>700 | ATC<br>Ile | CGT<br>Arg | ATT<br>Ile | CCC<br>Pro | CGA<br>Arg<br>705 | GGT<br>Gly | CAG<br>Gln | CTA<br>Leu | ACC<br>Thr | ATG<br>Met<br>710 | ATT<br>Ile | GTG<br>Val | GGG<br>Gly | 2163 |
| CAG<br>Gln | GTG<br>Val<br>715 | GGC<br>Gly | TGC<br>Cys | GGC<br>Gly | AAG<br>Lys<br>720 | TCC<br>Ser | TCG<br>Ser | CTC<br>Leu | CTC<br>Leu | CTC<br>Leu<br>725 | GCC<br>Ala | ACC<br>Thr | CTG<br>Leu | GGG<br>Gly | GAG<br>Glu | 2211 |
| ATG<br>Met<br>730 | CAG<br>Gln | AAG<br>Lys | GTG<br>Val | TCG<br>Ser | GGG<br>Gly<br>735 | GCC<br>Ala | GTC<br>Val | TTC<br>Phe | TGG<br>Trp | AAC<br>Asn<br>740 | AGC<br>Ser | AAC<br>Asn | CTT<br>Leu | CCG<br>Pro | GAC<br>Asp<br>745 | 2259 |
| AGC<br>Ser | GAG<br>Glu | GGG<br>Gly | AGA<br>Arg | GGA<br>Gly | CCC<br>Pro | CAG<br>Gln | CAG<br>Gln | CCC<br>Pro | AGA<br>Arg | GCG<br>Ala | GGA<br>Gly | GAC<br>Asp | AGC<br>Ser | AGC<br>Ser | TGG<br>Trp | 2307 |

|     |     |     |     |     |     |     |     |     |     |     |     |     |     |     |      |
| --- | --- | --- | --- | --- | --- | --- | --- | --- | --- | --- | --- | --- | --- | --- | ---- |
| Ser | Glu | Gly | Arg<br>750 | Gly | Pro | Gln | Gln<br>755 | Pro | Arg | Ala | Gly | Asp | Ser<br>760 | Trp |      |
| CTC | GGA | TAT | CAG | GAG | CAG | AGG | CCC | CGT | GGC | TAC | GCA | TCT | CAG | AAA | CCA  | 2355 |
| Leu | Gly | Tyr<br>765 | Gln | Glu | Gln | Arg | Pro<br>770 | Arg | Gly | Tyr | Ala | Ser | Gln<br>775 | Lys | Pro  |      |
| TGG | CTG | CTA | AAC | GCC | ACC | GTG | GAA | GAG | AAC | ATC | ACC | TTC | GAG | AGT | CCC  | 2403 |
| Trp | Leu | Leu<br>780 | Asn | Ala | Thr | Val | Glu<br>785 | Glu | Asn | Ile | Thr | Phe<br>790 | Glu | Ser | Pro  |      |
| TTC | AAT | CCG | CAG | CGG | TAC | AAG | ATG | GTC | ATC | GAA | GCC | TGC | TCC | CTG | CAG  | 2451 |
| Phe | Asn<br>795 | Pro | Gln | Arg | Tyr | Lys<br>800 | Met | Val | Ile | Glu | Ala<br>805 | Cys | Ser | Leu | Gln  |      |
| CCG | GAC | ATA | GAC | ATC | CTG | CCC | CAC | GGA | GAC | CAG | ACT | CAG | ATT | GGG | GAA  | 2499 |
| Pro<br>810 | Asp | Ile | Asp | Ile | Leu<br>815 | Pro | His | Gly | Asp | Gln<br>820 | Thr | Gln | Ile | Gly | Glu<br>825 |      |
| CGG | GGC | ATC | AAC | CTG | TCT | GGT | GGT | CAG | CGT | CCA | GAT | CAG | TGT | GGT | CCA  | 2547 |
| Arg | Gly | Ile | Asn | Leu<br>830 | Ser | Gly | Gly | Gln | Arg<br>835 | Pro | Asp | Gln | Cys | Gly<br>840 | Pro |      |
| GAG | CCC | TCT | ACC | AGC | AGA | CCA | ATG | TTC | GTC | TTC | TTG | GAT | GAC | CCC | TTC  | 2595 |
| Glu | Pro | Ser | Thr<br>845 | Ser | Arg | Pro | Met | Phe<br>850 | Val | Phe | Leu | Asp | Asp<br>855 | Pro | Phe  |      |
| TCA | GCT | TTG | GAT | GTC | CAT | CTG | AGT | GAC | CAC | CTG | ATG | CAG | GCC | GGC | ATC  | 2643 |
| Ser | Ala | Leu | Asp<br>860 | Val | His | Leu | Ser<br>865 | Asp | His | Leu | Met | Gln<br>870 | Ala | Gly | Ile  |      |
| CTT | GAG | CTG | CTC | CGG | GAT | GAC | AAG | AGG | ACA | GTG | GTC | TTG | GTG | ACC | CAC  | 2691 |
| Leu | Glu<br>875 | Leu | Leu | Arg | Asp | Asp<br>880 | Lys | Arg | Thr | Val | Val<br>885 | Leu | Val | Thr | His  |      |
| AAG | CTA | CAG | TAT | CTG | CCT | CAT | GCA | GAC | TGG | ATC | ATT | GCC | ATG | AAG | GAT  | 2739 |
| Lys<br>890 | Leu | Gln | Tyr | Leu | Pro<br>895 | His | Ala | Asp | Trp | Ile<br>900 | Ile | Ala | Met | Lys | Asp<br>905 |      |
| GGG | ACC | ATT | CAG | AGG | GAA | GGG | ACG | CTC | AAG | GAC | TTC | CAG | AGG | TCC | GAG  | 2787 |
| Gly | Thr | Ile | Gln | Arg<br>910 | Glu | Gly | Thr | Leu | Lys<br>915 | Asp | Phe | Gln | Arg | Ser<br>920 | Glu |      |
| TGC | CAG | CTC | TTT | GAG | CAC | TGG | AAG | ACC | CTC | ATG | AAC | CGG | CAG | GAC | CAA  | 2835 |
| Cys | Gln | Leu | Phe<br>925 | Glu | His | Trp | Lys | Thr<br>930 | Leu | Met | Asn | Arg | Gln<br>935 | Asp | Gln  |      |
| GAG | CTG | GAG | AAG | GAG | ACA | GTC | ATG | GAG | AGG | AAA | GCC | TCA | GAG | CCA | TCT  | 2883 |
| Glu | Leu | Glu | Lys<br>940 | Glu | Thr | Val | Met | Glu<br>945 | Arg | Lys | Ala | Ser | Glu<br>950 | Pro | Ser  |      |
| CAG | GGC | CTG | CCC | CGT | GCC | ATG | TCC | TCC | AGA | GAC | GGC | CTT | CTG | CTG | GAT  | 2931 |
| Gln | Gly | Leu<br>955 | Pro | Arg | Ala | Met | Ser<br>960 | Ser | Arg | Asp | Gly | Leu<br>965 | Leu | Leu | Asp  |      |
| GAG | GAA | GAG | GAG | GAA | GAG | GAG | GCA | GCC | GAA | AGC | GAG | GAA | GAT | GAC | AAC  | 2979 |
| Glu<br>970 | Glu | Glu | Glu | Glu | Glu<br>975 | Glu | Ala | Ala | Glu | Ser<br>980 | Glu | Glu | Asp | Asp | Asn<br>985 |      |
| TTA | TCT | TCA | GTG | CTG | CAT | CAG | CGA | GCT | AAG | ATC | CCC | TGG | CGA | GCC | TGC  | 3027 |
| Leu | Ser | Ser | Val | Leu<br>990 | His | Gln | Arg | Ala | Lys<br>995 | Ile | Pro | Trp | Arg | Ala<br>1000 | Cys |      |
| ACT | AAG | TAT | CTG | TCC | TCT | GCT | GGC | ATT | CTG | CTC | CTG | TCC | CTG | CTT | GTC  | 3075 |
| Thr | Lys | Tyr | Leu<br>1005 | Ser | Ser | Ala | Gly | Ile<br>1010 | Leu | Leu | Leu | Ser | Leu<br>1015 | Leu | Val  |      |
| TTC | TCC | CAG | CTG | CTC | AAG | CAC | ATG | GTC | TTG | GTG | GCC | ATT | GAT | TAT | TGG  | 3123 |
| Phe | Ser | Gln<br>1020 | Leu | Leu | Lys | His | Met<br>1025 | Val | Leu | Val | Ala | Ile<br>1030 | Asp | Tyr | Trp  |      |
| CTG | GCC | AAG | TGG | ACG | GAC | AGT | GCC | CTG | GTC | CTG | AGC | CCC | GCT | GCC | AGG  | 3171 |
| Leu | Ala | Lys<br>1035 | Trp | Thr | Asp | Ser | Ala<br>1040 | Leu | Val | Leu | Ser | Pro<br>1045 | Ala | Ala | Arg  |      |
| AAC | TGT | TCG | CTC | AGC | CAG | GAA | TGT | GAC | CTG | GAC | CAG | TCT | GTC | TAT | GCC  | 3219 |
| Asn | Cys | Ser | Leu | Ser<br>1050 | Gln | Glu | Cys | Asp | Leu<br>1055 | Asp | Gln | Ser | Val | Tyr<br>1065 | Ala |      |
| ATG | GTA | TTC | ACC | TTG | CTC | TGC | AGC | CTG | GGT | ATC | GTG | CTG | TGC | CTG | GTC  | 3267 |

|  |  |
|---|---|
| Met Val Phe Thr Leu Leu Cys Ser Leu Gly Ile Val Leu Cys Leu Val<br>                            1070                        1075                     1080 |  |
| ACC TCT GTC ACT GTG GAG TGG ACG GGA CTG AAG GTG GCC AAG AGG CTA<br>Thr Ser Val Thr Val Glu Trp Thr Gly Leu Lys Val Ala Lys Arg Leu<br>                1085                     1090                       1095 | 3315 |
| CAC CGC AGC CTG CTC AAC CGC ATC ATC CTG GCC CCC ATG AGG TTC TTT<br>His Arg Ser Leu Leu Asn Arg Ile Ile Leu Ala Pro Met Arg Phe Phe<br>        1100                     1105                      1110 | 3363 |
| GAG ACC ACA CCC CTC GGG AGT ATC CTG AAC AGA TTT TCA TCC GAC TGT<br>Glu Thr Thr Pro Leu Gly Ser Ile Leu Asn Arg Phe Ser Ser Asp Cys<br>1115                     1120                       1125 | 3411 |
| AAC ACC ATT GAC CAG CAC ATC CCA TCC ACG CTG GAG TGT CTG AGC CGG<br>Asn Thr Ile Asp Gln His Ile Pro Ser Thr Leu Glu Cys Leu Ser Arg<br>1130                     1135                     1140                    1145 | 3459 |
| TCC ACC CTG CTG TGT GTC TCC GCC CTG ACT GTC ATC TCC TAT GTC ACA<br>Ser Thr Leu Leu Cys Val Ser Ala Leu Thr Val Ile Ser Tyr Val Thr<br>                1150                     1155                      1160 | 3507 |
| CCC GTG TTC CTC GTG GCC CTC TTA CCC CTA GCT GTT GTG TGC TAC TTC<br>Pro Val Phe Leu Val Ala Leu Leu Pro Leu Ala Val Val Cys Tyr Phe<br>                1165                     1170                      1175 | 3555 |
| ATT CAG AAG TAC TTC CGA GTG GCA TCC AGG GAC CTG CAG CAG CTG GAC<br>Ile Gln Lys Tyr Phe Arg Val Ala Ser Arg Asp Leu Gln Gln Leu Asp<br>        1180                     1185                      1190 | 3603 |
| GAC ACG ACG CAG CTC CCG CTC GTC TCA CAC TTT GCT GAA ACT GTG GAG<br>Asp Thr Thr Gln Leu Pro Leu Val Ser His Phe Ala Glu Thr Val Glu<br>        1195                     1200                      1205 | 3651 |
| GGA CTC ACC ACC ATC CGT GCC TTC AGG TAC GAG GCC CGG TTC CAG CAG<br>Gly Leu Thr Thr Ile Arg Ala Phe Arg Tyr Glu Ala Arg Phe Gln Gln<br>1210                     1215                       1220                    1225 | 3699 |
| AAG CTT CTA GAA TAT ACC GAC TCC AAC AAC ATC GCC TCC CTC TTC CTC<br>Lys Leu Leu Glu Tyr Thr Asp Ser Asn Asn Ile Ala Ser Leu Phe Leu<br>                1230                     1235                      1240 | 3747 |
| ACG GCA GCC AAC AGA TGG CTG GAA GTC TGC ATG GAG TAC ATC GGA GCG<br>Thr Ala Ala Asn Arg Trp Leu Glu Val Cys Met Glu Tyr Ile Gly Ala<br>                1245                     1250                      1255 | 3795 |
| TGC GTG GTA CTC ATT GCG GCT GCC ACC TCC ATC TCC AAC TCC CTG CAC<br>Cys Val Val Leu Ile Ala Ala Ala Thr Ser Ile Ser Asn Ser Leu His<br>        1260                     1265                      1270 | 3843 |
| AGG GAA CTT TCT GCT GGC CTG GTG GGC CTG GGC CTC ACC TAT GCC TTG<br>Arg Glu Leu Ser Ala Gly Leu Val Gly Leu Gly Leu Thr Tyr Ala Leu<br>                1275                     1280                      1285 | 3891 |
| ATG GTC TCC AAC TAC CTC AAC TGG ATG GTG AGG AAC CTG GCG GAC ATG<br>Met Val Ser Asn Tyr Leu Asn Trp Met Val Arg Asn Leu Ala Asp Met<br>1290                     1295                       1300                    1305 | 3939 |
| GAG ATC CAG CTG GGG GCT GTG AAG AGG ATC CAC GCA CTC CTG AAA ACC<br>Glu Ile Gln Leu Gly Ala Val Lys Arg Ile His Ala Leu Leu Lys Thr<br>                            1310                     1315                    1320 | 3987 |
| GAG GCG GAG AGC TAT GAG GGG CTC CTG GCG CCG TCG TTG ATC CCC AAG<br>Glu Ala Glu Ser Tyr Glu Gly Leu Leu Ala Pro Ser Leu Ile Pro Lys<br>                      1325                     1330                    1335 | 4035 |
| AAC TGG CCA GAC CAA GGG AAG ATC CAA ATT CAG AAC CTG AGC GTG CGC<br>Asn Trp Pro Asp Gln Gly Lys Ile Gln Ile Gln Asn Leu Ser Val Arg<br>                1340                     1345                      1350 | 4083 |
| TAT GAC AGC TCC CTG AAG CCA GTG CTG AAG CAT GTC AAC ACC CTC ATC<br>Tyr Asp Ser Ser Leu Lys Pro Val Leu Lys His Val Asn Thr Leu Ile<br>        1355                     1360                      1365 | 4131 |
| TCC CCG GGG CAG AAG ATC GGG ATC TGC GGC CGC ACA GGC AGC GGG AAG<br>Ser Pro Gly Gln Lys Ile Gly Ile Cys Gly Arg Thr Gly Ser Gly Lys<br>1370                     1375                       1380                    1385 | 4179 |
| TCC TCC TTC TCC CTG GCC TTT TTC CGA ATG GTG GAC ATG TTT GAA GGA | 4227 |

| | | | | | | | | | | | | | | | | |
|---|---|---|---|---|---|---|---|---|---|---|---|---|---|---|---|---|
| Ser | Ser | Phe | Ser | Leu | Ala | Phe | Phe | Arg | Met | Val | Asp | Met | Phe | Glu | Gly | |
| | | | | 1390 | | | | 1395 | | | | | | 1400 | | |

```
CGC  ATC  ATC  ATT  GAT  GGC  ATC  GAC  ATC  GCC  AAG  CTG  CCA  CTT  CAC  ACG        4275
Arg  Ile  Ile  Ile  Asp  Gly  Ile  Asp  Ile  Ala  Lys  Leu  Pro  Leu  His  Thr
              1405                1410                    1415

CTG  CGC  TCA  CGC  CTG  TCC  ATC  ATC  CTA  CAG  GAC  CCC  GTC  CTC  TTC  AGC        4323
Leu  Arg  Ser  Arg  Leu  Ser  Ile  Ile  Leu  Gln  Asp  Pro  Val  Leu  Phe  Ser
              1420                1425                    1430

GGC  ACG  ATC  AGA  TTC  AAC  CTG  GAC  CCC  GAG  AAG  AAA  TGC  TCA  GAC  AGC        4371
Gly  Thr  Ile  Arg  Phe  Asn  Leu  Asp  Pro  Glu  Lys  Lys  Cys  Ser  Asp  Ser
              1435                1440                    1445

ACA  CTG  TGG  GAG  GCC  CTG  GAG  ATC  GCC  CAG  CTG  AAG  CTG  GTA  GTG  AAG        4419
Thr  Leu  Trp  Glu  Ala  Leu  Glu  Ile  Ala  Gln  Leu  Lys  Leu  Val  Val  Lys
1450                     1455                    1460                    1465

GCA  CTG  CCA  GGA  GGC  CTA  GAT  GCC  ATC  ATC  ACA  GAA  GGA  GGG  GAG  AAT        4467
Ala  Leu  Pro  Gly  Gly  Leu  Asp  Ala  Ile  Ile  Thr  Glu  Gly  Gly  Glu  Asn
                   1470                1475                    1480

TTT  AGC  CAG  GGC  CAG  AGG  CAG  CTG  TTC  TGC  CTG  GCC  CGG  GCC  TTC  GTG        4515
Phe  Ser  Gln  Gly  Gln  Arg  Gln  Leu  Phe  Cys  Leu  Ala  Arg  Ala  Phe  Val
              1485                1490                    1495

AGG  AAG  ACC  AGC  ATC  TTC  ATC  ATG  GAT  GAA  GCA  ACC  GCC  TCC  ATC  GAC        4563
Arg  Lys  Thr  Ser  Ile  Phe  Ile  Met  Asp  Glu  Ala  Thr  Ala  Ser  Ile  Asp
              1500                1505                    1510

ATG  GCT  ACG  GAG  AAC  ATC  CTC  CAG  AAG  GTG  GTG  ATG  ACA  GCC  TTC  GCA        4611
Met  Ala  Thr  Glu  Asn  Ile  Leu  Gln  Lys  Val  Val  Met  Thr  Ala  Phe  Ala
              1515                1520                    1525

GAC  CGC  ACG  GTG  GTC  ACC  ATC  GCG  CAT  CGT  GTG  CAC  ACC  ATC  CTG  AGT        4659
Asp  Arg  Thr  Val  Val  Thr  Ile  Ala  His  Arg  Val  His  Thr  Ile  Leu  Ser
1530                     1535                    1540                    1545

GCA  GAC  CTG  GTG  ATG  GTC  CTC  AAG  AGG  GGT  GCT  ATC  CTG  GAG  TTT  GAC        4707
Ala  Asp  Leu  Val  Met  Val  Leu  Lys  Arg  Gly  Ala  Ile  Leu  Glu  Phe  Asp
                   1550                1555                    1560

AAG  CCA  GAG  ACG  CTC  CTC  AGC  CAG  AAG  GAC  AGC  GTG  TTC  GCC  TCC  TTT        4755
Lys  Pro  Glu  Thr  Leu  Leu  Ser  Gln  Lys  Asp  Ser  Val  Phe  Ala  Ser  Phe
              1565                1570                    1575

GTC  CGT  GCG  GAC  AAG  TGACTTACCG  GAGCCAAAGT  GCCACCCCGC  GCCTCGCTTG            4810
Val  Arg  Ala  Asp  Lys
              1580

CTTGCCTAGG  ATTTCTAACT  GCAAATCACT  TGTAAATAAA  TTAATTCTTT  GCTAAAAAAA              4870

AAAAAAA                                                                               4877
```

( 2 ) INFORMATION FOR SEQ ID NO:9:

( i ) SEQUENCE CHARACTERISTICS:
        ( A ) LENGTH: 1582 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Pro  Leu  Ala  Phe  Cys  Gly  Thr  Glu  Asn  His  Ser  Ala  Ala  Tyr  Arg
1                  5                   10                      15

Val  Asp  Gln  Gly  Val  Leu  Asn  Asn  Gly  Cys  Phe  Val  Asp  Ala  Leu  Asn
                   20                  25                      30

Val  Val  Pro  His  Val  Phe  Leu  Leu  Phe  Ile  Thr  Phe  Pro  Ile  Leu  Phe
              35                  40                  45

Ile  Gly  Trp  Gly  Ser  Gln  Ser  Ser  Lys  Val  His  Ile  His  His  Ser  Thr
         50                  55                  60

Trp  Leu  His  Phe  Pro  Gly  His  Asn  Leu  Arg  Trp  Ile  Leu  Thr  Phe  Ile
```

-continued

```
              65                      70                      75                      80
Leu  Leu  Phe  Val  Leu  Val  Cys  Glu  Ile  Ala  Glu  Gly  Ile  Leu  Ser  Asp
                    85                      90                      95

Gly  Val  Thr  Glu  Ser  Arg  His  Leu  His  Leu  Tyr  Met  Pro  Ala  Gly  Met
              100                     105                     110

Ala  Phe  Met  Ala  Ala  Ile  Thr  Ser  Val  Val  Tyr  Tyr  His  Asn  Ile  Glu
              115                     120                     125

Thr  Ser  Asn  Phe  Pro  Lys  Leu  Leu  Ile  Ala  Leu  Leu  Ile  Tyr  Trp  Thr
              130                     135                     140

Leu  Ala  Phe  Ile  Thr  Lys  Thr  Ile  Lys  Phe  Val  Lys  Phe  Tyr  Asp  His
145                     150                     155                     160

Ala  Ile  Gly  Phe  Ser  Gln  Leu  Arg  Phe  Cys  Leu  Thr  Gly  Leu  Leu  Val
              165                     170                     175

Ile  Leu  Tyr  Gly  Met  Leu  Leu  Leu  Val  Glu  Val  Asn  Val  Ile  Arg  Val
              180                     185                     190

Arg  Arg  Tyr  Ile  Phe  Phe  Lys  Thr  Pro  Arg  Glu  Val  Lys  Pro  Pro  Glu
              195                     200                     205

Asp  Leu  Gln  Asp  Leu  Gly  Val  Arg  Phe  Leu  Gln  Pro  Phe  Val  Asn  Leu
210                     215                     220

Leu  Ser  Lys  Gly  Thr  Tyr  Trp  Trp  Met  Asn  Ala  Phe  Ile  Lys  Thr  Ala
225                     230                     235                     240

His  Lys  Lys  Pro  Ile  Asp  Leu  Arg  Ala  Ile  Ala  Lys  Leu  Pro  Ile  Ala
              245                     250                     255

Met  Arg  Ala  Leu  Thr  Asn  Tyr  Gln  Arg  Leu  Cys  Val  Ala  Phe  Asp  Ala
              260                     265                     270

Gln  Ala  Arg  Lys  Asp  Thr  Gln  Ser  Pro  Gln  Gly  Ala  Arg  Ala  Ile  Trp
              275                     280                     285

Arg  Ala  Leu  Cys  His  Ala  Phe  Gly  Arg  Arg  Leu  Ile  Leu  Ser  Ser  Thr
290                     295                     300

Phe  Arg  Ile  Leu  Ala  Asp  Leu  Leu  Gly  Phe  Ala  Gly  Pro  Leu  Cys  Ile
305                     310                     315                     320

Phe  Gly  Ile  Val  Asp  His  Leu  Gly  Lys  Glu  Asn  His  Val  Phe  Gln  Pro
              325                     330                     335

Lys  Thr  Gln  Phe  Leu  Gly  Val  Tyr  Phe  Val  Ser  Ser  Gln  Glu  Phe  Leu
              340                     345                     350

Gly  Asn  Ala  Tyr  Val  Leu  Ala  Val  Leu  Leu  Phe  Leu  Ala  Leu  Leu  Leu
              355                     360                     365

Gln  Arg  Thr  Phe  Leu  Gln  Ala  Ser  Tyr  Tyr  Val  Ala  Ile  Glu  Thr  Gly
              370                     375                     380

Ile  Asn  Leu  Arg  Gly  Ala  Ile  Gln  Thr  Lys  Ile  Tyr  Asn  Lys  Ile  Met
385                     390                     395                     400

His  Met  Ser  Thr  Ser  Asn  Leu  Ser  Met  Gly  Glu  Met  Thr  Ala  Gly  Gln
                    405                     410                     415

Ile  Cys  Asn  Leu  Val  Ala  Ile  Asp  Thr  Asn  Gln  Leu  Met  Trp  Phe  Phe
              420                     425                     430

Phe  Leu  Cys  Pro  Asn  Leu  Trp  Thr  Met  Pro  Val  Gln  Ile  Ile  Val  Gly
              435                     440                     445

Val  Ile  Leu  Leu  Tyr  Tyr  Ile  Leu  Gly  Val  Ser  Ala  Leu  Ile  Gly  Ala
              450                     455                     460

Ala  Val  Ile  Ile  Leu  Leu  Ala  Pro  Val  Gln  Tyr  Phe  Val  Ala  Thr  Lys
465                     470                     475                     480

Leu  Ser  Gln  Ala  Gln  Arg  Thr  Thr  Leu  Glu  His  Ser  Asn  Glu  Arg  Leu
              485                     490                     495
```

| Lys | Gln | Thr | Asn | Glu | Met | Leu | Arg | Gly | Met | Lys | Leu | Leu | Lys | Leu | Tyr |
|---|---|---|---|---|---|---|---|---|---|---|---|---|---|---|---|
| | | | 500 | | | | 505 | | | | 510 | | | | |

| Ala | Trp | Glu | Ser | Ile | Phe | Cys | Ser | Arg | Val | Glu | Val | Thr | Arg | Arg | Lys |
|---|---|---|---|---|---|---|---|---|---|---|---|---|---|---|---|
| | | 515 | | | | 520 | | | | 525 | | | | | |

| Glu | Met | Thr | Ser | Leu | Arg | Ala | Phe | Ala | Val | Tyr | Thr | Ser | Ile | Ser | Ile |
|---|---|---|---|---|---|---|---|---|---|---|---|---|---|---|---|
| | 530 | | | | 535 | | | | | 540 | | | | | |

| Phe | Met | Asn | Thr | Ala | Ile | Pro | Ile | Ala | Ala | Val | Leu | Ile | Thr | Phe | Val |
|---|---|---|---|---|---|---|---|---|---|---|---|---|---|---|---|
| 545 | | | | 550 | | | | 555 | | | | | | | 560 |

| Gly | His | Val | Ser | Phe | Phe | Lys | Glu | Ser | Asp | Leu | Ser | Pro | Ser | Val | Ala |
|---|---|---|---|---|---|---|---|---|---|---|---|---|---|---|---|
| | | | | 565 | | | | 570 | | | | | 575 | | |

| Phe | Ala | Ser | Leu | Ser | Leu | Phe | His | Ile | Leu | Val | Thr | Pro | Leu | Phe | Leu |
|---|---|---|---|---|---|---|---|---|---|---|---|---|---|---|---|
| | | | 580 | | | | 585 | | | | | 590 | | | |

| Leu | Ser | Ser | Val | Val | Arg | Ser | Thr | Val | Lys | Ala | Leu | Val | Ser | Val | Gln |
|---|---|---|---|---|---|---|---|---|---|---|---|---|---|---|---|
| | 595 | | | | | 600 | | | | | 605 | | | | |

| Lys | Leu | Ser | Glu | Phe | Leu | Ser | Ser | Ala | Glu | Ile | Arg | Glu | Glu | Gln | Cys |
|---|---|---|---|---|---|---|---|---|---|---|---|---|---|---|---|
| 610 | | | | | 615 | | | | | 620 | | | | | |

| Ala | Pro | Arg | Glu | Pro | Ala | Pro | Gln | Gly | Gln | Ala | Gly | Lys | Tyr | Gln | Ala |
|---|---|---|---|---|---|---|---|---|---|---|---|---|---|---|---|
| 625 | | | | | 630 | | | | 635 | | | | | | 640 |

| Val | Pro | Leu | Lys | Val | Asn | Arg | Lys | Arg | Pro | Ala | Arg | Glu | Val |
|---|---|---|---|---|---|---|---|---|---|---|---|---|---|
| | | | | 645 | | | | 650 | | | | 655 | |

| Arg | Asp | Leu | Leu | Gly | Pro | Leu | Gln | Arg | Leu | Ala | Pro | Ser | Met | Asp | Gly |
|---|---|---|---|---|---|---|---|---|---|---|---|---|---|---|---|
| | | | 660 | | | | 665 | | | | | 670 | | | |

| Asp | Ala | Asp | Asn | Phe | Cys | Val | Gln | Ile | Ile | Gly | Gly | Phe | Phe | Thr | Trp |
|---|---|---|---|---|---|---|---|---|---|---|---|---|---|---|---|
| | | 675 | | | | | 680 | | | | | 685 | | | |

| Thr | Pro | Asp | Gly | Ile | Pro | Thr | Leu | Ser | Asn | Ile | Thr | Ile | Arg | Ile | Pro |
|---|---|---|---|---|---|---|---|---|---|---|---|---|---|---|---|
| | 690 | | | | | 695 | | | | 700 | | | | | |

| Arg | Gly | Gln | Leu | Thr | Met | Ile | Val | Gly | Gln | Val | Gly | Cys | Gly | Lys | Ser |
|---|---|---|---|---|---|---|---|---|---|---|---|---|---|---|---|
| 705 | | | | | 710 | | | | 715 | | | | | | 720 |

| Ser | Leu | Leu | Leu | Ala | Thr | Leu | Gly | Glu | Met | Gln | Lys | Val | Ser | Gly | Ala |
|---|---|---|---|---|---|---|---|---|---|---|---|---|---|---|---|
| | | | | 725 | | | | 730 | | | | | 735 | | |

| Val | Phe | Trp | Asn | Ser | Asn | Leu | Pro | Asp | Ser | Glu | Gly | Arg | Gly | Pro | Gln |
|---|---|---|---|---|---|---|---|---|---|---|---|---|---|---|---|
| | | | 740 | | | | 745 | | | | | 750 | | | |

| Gln | Pro | Arg | Ala | Gly | Asp | Ser | Ser | Trp | Leu | Gly | Tyr | Gln | Glu | Gln | Arg |
|---|---|---|---|---|---|---|---|---|---|---|---|---|---|---|---|
| | | 755 | | | | 760 | | | | | 765 | | | | |

| Pro | Arg | Gly | Tyr | Ala | Ser | Gln | Lys | Pro | Trp | Leu | Leu | Asn | Ala | Thr | Val |
|---|---|---|---|---|---|---|---|---|---|---|---|---|---|---|---|
| | 770 | | | | | 775 | | | | 780 | | | | | |

| Glu | Glu | Asn | Ile | Thr | Phe | Glu | Ser | Pro | Phe | Asn | Pro | Gln | Arg | Tyr | Lys |
|---|---|---|---|---|---|---|---|---|---|---|---|---|---|---|---|
| 785 | | | | | 790 | | | | 795 | | | | | | 800 |

| Met | Val | Ile | Glu | Ala | Cys | Ser | Leu | Gln | Pro | Asp | Ile | Asp | Ile | Leu | Pro |
|---|---|---|---|---|---|---|---|---|---|---|---|---|---|---|---|
| | | | | 805 | | | | 810 | | | | | | 815 | |

| His | Gly | Asp | Gln | Thr | Gln | Ile | Gly | Glu | Arg | Gly | Ile | Asn | Leu | Ser | Gly |
|---|---|---|---|---|---|---|---|---|---|---|---|---|---|---|---|
| | | | 820 | | | | | 825 | | | | | 830 | | |

| Gly | Gln | Arg | Pro | Asp | Gln | Cys | Gly | Pro | Glu | Pro | Ser | Thr | Ser | Arg | Pro |
|---|---|---|---|---|---|---|---|---|---|---|---|---|---|---|---|
| | | 835 | | | | | 840 | | | | | 845 | | | |

| Met | Phe | Val | Phe | Leu | Asp | Asp | Pro | Phe | Ser | Ala | Leu | Asp | Val | His | Leu |
|---|---|---|---|---|---|---|---|---|---|---|---|---|---|---|---|
| | 850 | | | | | 855 | | | | 860 | | | | | |

| Ser | Asp | His | Leu | Met | Gln | Ala | Gly | Ile | Leu | Glu | Leu | Leu | Arg | Asp | Asp |
|---|---|---|---|---|---|---|---|---|---|---|---|---|---|---|---|
| 865 | | | | | 870 | | | | | 875 | | | | | 880 |

| Lys | Arg | Thr | Val | Val | Leu | Val | Thr | His | Lys | Leu | Gln | Tyr | Leu | Pro | His |
|---|---|---|---|---|---|---|---|---|---|---|---|---|---|---|---|
| | | | | 885 | | | | | 890 | | | | | 895 | |

| Ala | Asp | Trp | Ile | Ile | Ala | Met | Lys | Asp | Gly | Thr | Ile | Gln | Arg | Glu | Gly |
|---|---|---|---|---|---|---|---|---|---|---|---|---|---|---|---|
| | | | 900 | | | | | 905 | | | | | 910 | | |

| Thr | Leu | Lys | Asp | Phe | Gln | Arg | Ser | Glu | Cys | Gln | Leu | Phe | Glu | His | Trp |
|---|---|---|---|---|---|---|---|---|---|---|---|---|---|---|---|
| | | 915 | | | | | 920 | | | | | 925 | | | |

```
Lys  Thr  Leu  Met  Asn  Arg  Gln  Asp  Gln  Glu  Leu  Glu  Lys  Glu  Thr  Val
     930                 935                 940

Met  Glu  Arg  Lys  Ala  Ser  Glu  Pro  Ser  Gln  Gly  Leu  Pro  Arg  Ala  Met
945                      950                 955                           960

Ser  Ser  Arg  Asp  Gly  Leu  Leu  Leu  Asp  Glu  Glu  Glu  Glu  Glu  Glu  Glu
               965                 970                      975

Ala  Ala  Glu  Ser  Glu  Glu  Asp  Asp  Asn  Leu  Ser  Ser  Val  Leu  His  Gln
               980                 985                           990

Arg  Ala  Lys  Ile  Pro  Trp  Arg  Ala  Cys  Thr  Lys  Tyr  Leu  Ser  Ser  Ala
          995                      1000                1005

Gly  Ile  Leu  Leu  Leu  Ser  Leu  Leu  Val  Phe  Ser  Gln  Leu  Leu  Lys  His
          1010                1015                1020

Met  Val  Leu  Val  Ala  Ile  Asp  Tyr  Trp  Leu  Ala  Lys  Trp  Thr  Asp  Ser
1025                1030                1035                          1040

Ala  Leu  Val  Leu  Ser  Pro  Ala  Ala  Arg  Asn  Cys  Ser  Leu  Ser  Gln  Glu
               1045                1050                1055

Cys  Asp  Leu  Asp  Gln  Ser  Val  Tyr  Ala  Met  Val  Phe  Thr  Leu  Leu  Cys
               1060                1065                1070

Ser  Leu  Gly  Ile  Val  Leu  Cys  Leu  Val  Thr  Ser  Val  Thr  Val  Glu  Trp
               1075                1080                1085

Thr  Gly  Leu  Lys  Val  Ala  Lys  Arg  Leu  His  Arg  Ser  Leu  Leu  Asn  Arg
          1090                1095                1100

Ile  Ile  Leu  Ala  Pro  Met  Arg  Phe  Phe  Glu  Thr  Thr  Pro  Leu  Gly  Ser
1105                1110                1115                          1120

Ile  Leu  Asn  Arg  Phe  Ser  Ser  Asp  Cys  Asn  Thr  Ile  Asp  Gln  His  Ile
               1125                1130                1135

Pro  Ser  Thr  Leu  Glu  Cys  Leu  Ser  Arg  Ser  Thr  Leu  Leu  Cys  Val  Ser
               1140                1145                1150

Ala  Leu  Thr  Val  Ile  Ser  Tyr  Val  Thr  Pro  Val  Phe  Leu  Val  Ala  Leu
          1155                1160                1165

Leu  Pro  Leu  Ala  Val  Val  Cys  Tyr  Phe  Ile  Gln  Lys  Tyr  Phe  Arg  Val
     1170                1175                1180

Ala  Ser  Arg  Asp  Leu  Gln  Gln  Leu  Asp  Asp  Thr  Thr  Gln  Leu  Pro  Leu
1185                1190                1195                          1200

Val  Ser  His  Phe  Ala  Glu  Thr  Val  Glu  Gly  Leu  Thr  Thr  Ile  Arg  Ala
               1205                1210                1215

Phe  Arg  Tyr  Glu  Ala  Arg  Phe  Gln  Gln  Lys  Leu  Leu  Glu  Tyr  Thr  Asp
               1220                1225                1230

Ser  Asn  Asn  Ile  Ala  Ser  Leu  Phe  Leu  Thr  Ala  Ala  Asn  Arg  Trp  Leu
               1235                1240                1245

Glu  Val  Cys  Met  Glu  Tyr  Ile  Gly  Ala  Cys  Val  Val  Leu  Ile  Ala  Ala
     1250                1255                1260

Ala  Thr  Ser  Ile  Ser  Asn  Ser  Leu  His  Arg  Glu  Leu  Ser  Ala  Gly  Leu
1265                1270                1275                          1280

Val  Gly  Leu  Gly  Leu  Thr  Tyr  Ala  Leu  Met  Val  Ser  Asn  Tyr  Leu  Asn
               1285                1290                1295

Trp  Met  Val  Arg  Asn  Leu  Ala  Asp  Met  Glu  Ile  Gln  Leu  Gly  Ala  Val
               1300                1305                1310

Lys  Arg  Ile  His  Ala  Leu  Leu  Lys  Thr  Glu  Ala  Glu  Ser  Tyr  Glu  Gly
          1315                1320                1325

Leu  Leu  Ala  Pro  Ser  Leu  Ile  Pro  Lys  Asn  Trp  Pro  Asp  Gln  Gly  Lys
          1330                1335                1340

Ile  Gln  Ile  Gln  Asn  Leu  Ser  Val  Arg  Tyr  Asp  Ser  Ser  Leu  Lys  Pro
```

|   | 1345 | | | | | 1350 | | | | | 1355 | | | | | 1360 |
| --- | --- | --- | --- | --- | --- | --- | --- | --- | --- | --- | --- | --- | --- | --- | --- | --- |

Val Leu Lys His Val Asn Thr Leu Ile Ser Pro Gly Gln Lys Ile Gly
             1365                  1370                1375

Ile Cys Gly Arg Thr Gly Ser Gly Lys Ser Ser Phe Ser Leu Ala Phe
         1380                   1385               1390

Phe Arg Met Val Asp Met Phe Glu Gly Arg Ile Ile Ile Asp Gly Ile
         1395                   1400               1405

Asp Ile Ala Lys Leu Pro Leu His Thr Leu Arg Ser Arg Leu Ser Ile
1410                   1415               1420

Ile Leu Gln Asp Pro Val Leu Phe Ser Gly Thr Ile Arg Phe Asn Leu
1425                   1430               1435               1440

Asp Pro Glu Lys Lys Cys Ser Asp Ser Thr Leu Trp Glu Ala Leu Glu
         1445                   1450               1455

Ile Ala Gln Leu Lys Leu Val Val Lys Ala Leu Pro Gly Gly Leu Asp
         1460                   1465               1470

Ala Ile Ile Thr Glu Gly Gly Glu Asn Phe Ser Gln Gly Gln Arg Gln
         1475                   1480               1485

Leu Phe Cys Leu Ala Arg Ala Phe Val Arg Lys Thr Ser Ile Phe Ile
         1490                   1495               1500

Met Asp Glu Ala Thr Ala Ser Ile Asp Met Ala Thr Glu Asn Ile Leu
1505                   1510               1515               1520

Gln Lys Val Val Met Thr Ala Phe Ala Asp Arg Thr Val Val Thr Ile
                  1525               1530               1535

Ala His Arg Val His Thr Ile Leu Ser Ala Asp Leu Val Met Val Leu
                 1540                1545               1550

Lys Arg Gly Ala Ile Leu Glu Phe Asp Lys Pro Glu Thr Leu Leu Ser
         1555                   1560               1565

Gln Lys Asp Ser Val Phe Ala Ser Phe Val Arg Ala Asp Lys
1570                   1575               1580

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: Amino acid ( x i ) SEQUENCE DESCRIPTION: SEQ ID NO:10:

Met Pro Leu Ala Phe Cys Gly Thr
 1               5

( 2 ) INFORMATION FOR SEQ ID NO:11:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: Amino acid ( x i ) SEQUENCE DESCRIPTION: SEQ ID NO:11:

Asn His Ser Ala Ala Tyr Arg Val Asp Gln Gly
 1               5

( 2 ) INFORMATION FOR SEQ ID NO:12:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (ii) MOLECULE TYPE: nucleic acids (iii) HYPOTHETICAL: NO (iv) ANTI-SENSE: NO (xi) SEQUENCE DESCRIPTION: SEQ ID NO:12:

CACGCTCAGG TTCTGGAT 18

(2) INFORMATION FOR SEQ ID NO:13:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: nucleic acids (iii) HYPOTHETICAL: NO (iv) ANTI-SENSE: YES (xi) SEQUENCE DESCRIPTION: SEQ ID NO:13:

TCAACTGGAT GGTGAGGA 18

(2) INFORMATION FOR SEQ ID NO:14:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: nucleic acid (iii) HYPOTHETICAL: NO (iv) ANTI-SENSE: NO (xi) SEQUENCE DESCRIPTION: SEQ ID NO:14:

TGACATCGCC AAACTGC 17

(2) INFORMATION FOR SEQ ID NO:15:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: nucleic acid (iii) HYPOTHETICAL: NO (iv) ANTI-SENSE: YES (xi) SEQUENCE DESCRIPTION: SEQ ID NO:15:

TCCTGGCAGT GCCTTCA 17

(2) INFORMATION FOR SEQ ID NO:16:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: nucleic acid ( i i i ) HYPOTHETICAL: NO ( i v ) ANTI-SENSE: YES ( x i ) SEQUENCE DESCRIPTION: SEQ ID NO:16:

TCCTCTCAGG GTCCAGGTTA 20

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:17:

ACAAGGAGCC TGGGGAT 17

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: YES ( x i ) SEQUENCE DESCRIPTION: SEQ ID NO:18:

TGCATGGGTC CCAGTGA 17

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:19:

TTGACCATTC ACCACATTGG TGTGC 25

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: YES ( x i ) SEQUENCE DESCRIPTION: SEQ ID NO:20:

TCCTGGCAGT GCCTTCA                                                                                                17

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

Met Pro Leu Ala Phe Cys Gly Thr
1               5

( 2 ) INFORMATION FOR SEQ ID NO:22:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

Asn His Ser Ala Ala Tyr Arg Val Asp Gln Gly
1               5                   10

( 2 ) INFORMATION FOR SEQ ID NO:23:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Nucleic Acid ( x i ) SEQUENCE DESCRIPTION: SEQ ID NO:23:

GAGAGAAGCT TNTGNGGNGA NAANCA                                                                      26

( 2 ) INFORMATION FOR SEQ ID NO:24:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: Nucleic Acid ( x i ) SEQUENCE DESCRIPTION: SEQ ID NO:24:

GAGAGAGAAT TCCNTGNTCN ACNCNNTA                                                                    28

( 2 ) INFORMATION FOR SEQ ID NO:25:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Nucleic Acid ( x i ) SEQUENCE DESCRIPTION: SEQ ID NO:25:

TTTTGCGGGA CGGAGAATCA CTCGGCCGCC TACCGCGTCG ACCAAGG                                                47

( 2 ) INFORMATION FOR SEQ ID NO:26:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: Nucleic Acid ( x i ) SEQUENCE DESCRIPTION: SEQ ID NO:26:

```
GCCNCCAUG                                                                                          9
```

( 2 ) INFORMATION FOR SEQ ID NO:27:

( i ) SEQUENCE CHARACTERISTICS:
        ( A ) LENGTH: 4635 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( i x ) FEATURE:
        ( A ) NAME/KEY: CDS
        ( B ) LOCATION: 37..4533

( x i ) SEQUENCE DESCRIPTION: SEQ ID NO:27:

```
GCGCGGAGCC  GGAGCCGAGC  CCGTGCGCGC  GCCACC  ATG  CCT  TTG  GCC  TTC  TGC        54
                                            Met  Pro  Leu  Ala  Phe  Cys
                                             1                    5

GGC  ACC  GAG  AAC  CAC  TCG  GCC  GCC  TAC  CGG  GTG  GAC  CAA  GGC  GTC  CTC  102
Gly  Thr  Glu  Asn  His  Ser  Ala  Ala  Tyr  Arg  Val  Asp  Gln  Gly  Val  Leu
               10                      15                      20

AAC  AAC  GGC  TGC  TTC  GTG  GAC  GCG  CTC  AAT  GTG  GTG  CCA  CAT  GTC  TTT  150
Asn  Asn  Gly  Cys  Phe  Val  Asp  Ala  Leu  Asn  Val  Val  Pro  His  Val  Phe
               25                      30                      35

CTG  CTC  TTC  ATC  ACC  TTC  CCC  ATC  CTC  TTC  ATC  GGA  TGG  GGC  AGC  CAG  198
Leu  Leu  Phe  Ile  Thr  Phe  Pro  Ile  Leu  Phe  Ile  Gly  Trp  Gly  Ser  Gln
     40                      45                      50

AGC  TCC  AAG  GTG  CAC  ATT  CAC  CAC  AGC  ACC  TGG  CTC  CAT  TTC  CCG  GGG  246
Ser  Ser  Lys  Val  His  Ile  His  His  Ser  Thr  Trp  Leu  His  Phe  Pro  Gly
55                       60                      65                       70

CAC  AAC  CTG  CGC  TGG  ATC  CTG  ACC  TTC  ATA  CTG  CTC  TTC  GTC  CTC  GTG  294
His  Asn  Leu  Arg  Trp  Ile  Leu  Thr  Phe  Ile  Leu  Leu  Phe  Val  Leu  Val
                    75                      80                      85

TGT  GAG  ATC  GCT  GAG  GGT  ATC  CTG  TCT  GAC  GGG  GTG  ACA  GAA  TCC  CGC  342
Cys  Glu  Ile  Ala  Glu  Gly  Ile  Leu  Ser  Asp  Gly  Val  Thr  Glu  Ser  Arg
               90                      95                      100

CAC  CTC  CAC  TTA  TAC  ATG  CCA  GCT  GGG  ATG  GCA  TTC  ATG  GCT  GCC  ATC  390
His  Leu  His  Leu  Tyr  Met  Pro  Ala  Gly  Met  Ala  Phe  Met  Ala  Ala  Ile
          105                     110                     115

ACC  TCT  GTG  GTC  TAC  TAC  CAT  AAC  ATT  GAG  ACC  TCT  AAC  TTT  CCC  AAG  438
Thr  Ser  Val  Val  Tyr  Tyr  His  Asn  Ile  Glu  Thr  Ser  Asn  Phe  Pro  Lys
     120                     125                     130

CTG  CTG  ATT  GCT  CTG  CTC  ATC  TAC  TGG  ACC  CTG  GCC  TTC  ATC  ACG  AAG  486
Leu  Leu  Ile  Ala  Leu  Leu  Ile  Tyr  Trp  Thr  Leu  Ala  Phe  Ile  Thr  Lys
135                     140                     145                     150

ACC  ATC  AAG  TTC  GTC  AAG  TTC  TAC  GAC  CAC  GCC  ATT  GGC  TTC  TCT  CAG  534
Thr  Ile  Lys  Phe  Val  Lys  Phe  Tyr  Asp  His  Ala  Ile  Gly  Phe  Ser  Gln
```

|  |  |  |  |  |  |  |  |  |  |  |  |  |  |  |  |  |
|---|---|---|---|---|---|---|---|---|---|---|---|---|---|---|---|---|
|  |  |  |  | 155 |  |  |  | 160 |  |  |  |  |  | 165 |  |  |
| CTG | CGC | TTC | TGC | CTC | ACG | GGG | CTT | CTG | GTG | ATC | CTC | TAC | GGG | ATG | CTG | 582 |
| Leu | Arg | Phe | Cys 170 | Leu | Thr | Gly | Leu | Leu 175 | Val | Ile | Leu | Tyr | Gly 180 | Met | Leu |  |
| CTG | CTT | GTG | GAG | GTC | AAT | GTC | ATC | CGG | GTG | AGG | AGA | TAC | GTC | TTC | TTC | 630 |
| Leu | Leu | Val 185 | Glu | Val | Asn | Val | Ile 190 | Arg | Val | Arg | Arg | Tyr 195 | Val | Phe | Phe |  |
| AAG | ACA | CCA | AGG | GAA | GTA | AAG | CCC | CCC | GAG | GAC | CTA | CAG | GAC | CTG | GGT | 678 |
| Lys | Thr 200 | Pro | Arg | Glu | Val | Lys 205 | Pro | Pro | Glu | Asp | Leu 210 | Gln | Asp | Leu | Gly |  |
| GTG | CGC | TTT | CTG | CAG | CCC | TTC | GTT | AAC | CTG | CTA | TCA | AAG | GGG | ACC | TAC | 726 |
| Val 215 | Arg | Phe | Leu | Gln 220 | Pro | Phe | Val | Asn | Leu 225 | Leu | Ser | Lys | Gly | Thr 230 | Tyr |  |
| TGG | TGG | ATG | AAT | GCC | TTC | ATC | AAG | ACT | GCT | CAC | AAG | AAG | CCC | ATC | GAC | 774 |
| Trp | Trp | Met | Asn 235 | Ala | Phe | Ile | Lys | Thr 240 | Ala | His | Lys | Lys | Pro 245 | Ile | Asp |  |
| CTG | CGG | GCC | ATC | GGG | AAG | CTG | CCC | ATT | GCC | ATG | AGA | GCC | CTC | ACC | AAC | 822 |
| Leu | Arg | Ala | Ile 250 | Gly | Lys | Leu | Pro | Ile 255 | Ala | Met | Arg | Ala | Leu 260 | Thr | Asn |  |
| TAC | CAG | CGA | CTC | TGC | TTG | GCC | TTC | GAT | GCC | CAG | GCG | CGG | AAG | GAC | ACA | 870 |
| Tyr | Gln | Arg 265 | Leu | Cys | Leu | Ala | Phe 270 | Asp | Ala | Gln | Ala | Arg 275 | Lys | Asp | Thr |  |
| CAG | AGC | CAG | CAG | GGT | GCC | CGG | GCC | ATC | TGG | AGG | GCT | CTC | TGT | CAT | GCC | 918 |
| Gln | Ser 280 | Gln | Gln | Gly | Ala | Arg 285 | Ala | Ile | Trp | Arg | Ala 290 | Leu | Cys | His | Ala |  |
| TTT | GGG | AGA | CGG | CTG | GTC | CTC | AGC | AGC | ACA | TTC | CGT | ATC | CTG | GCC | GAC | 966 |
| Phe 295 | Gly | Arg | Arg | Leu | Val 300 | Leu | Ser | Ser | Thr | Phe 305 | Arg | Ile | Leu | Ala | Asp 310 |  |
| CTC | CTG | GGC | TTT | GCT | GGG | CCA | CTC | TGC | ATC | TTC | GGG | ATC | GTG | GAC | CAC | 1014 |
| Leu | Leu | Gly | Phe | Ala 315 | Gly | Pro | Leu | Cys | Ile 320 | Phe | Gly | Ile | Val | Asp 325 | His |  |
| CTC | GGG | AAG | GAG | AAC | CAC | GTC | TTC | CAG | CCC | AAG | ACA | CAG | TTT | CTT | GGA | 1062 |
| Leu | Gly | Lys | Glu 330 | Asn | His | Val | Phe | Gln 335 | Pro | Lys | Thr | Gln | Phe 340 | Leu | Gly |  |
| GTT | TAC | TTT | GTC | TCA | TCC | CAA | GAG | TTC | CTC | GGC | AAT | GCC | TAT | GTC | TTG | 1110 |
| Val | Tyr | Phe 345 | Val | Ser | Ser | Gln | Glu 350 | Phe | Leu | Gly | Asn | Ala 355 | Tyr | Val | Leu |  |
| GCT | GTT | CTT | CTG | TTC | CTT | GCC | CTC | CTG | CAA | AGG | ACC | TTT | CTA | CAA | | 1158 |
| Ala | Val | Leu 360 | Leu | Phe | Leu | Ala | Leu 365 | Leu | Leu | Gln | Arg | Thr 370 | Phe | Leu | Gln |  |
| GCC | TCG | TAC | TAC | GTT | GCC | ATT | GAA | ACT | GGG | ATC | AAC | CTG | AGA | GGA | GCA | 1206 |
| Ala | Ser | Tyr 375 | Tyr | Val | Ala | Ile | Glu 380 | Thr | Gly | Ile | Asn | Leu 385 | Arg | Gly | Ala 390 |  |
| ATC | CAG | ACC | AAG | ATT | TAC | AAT | AAG | ATC | ATG | CAC | TTG | TCT | ACT | TCC | AAC | 1254 |
| Ile | Gln | Thr | Lys | Ile 395 | Tyr | Asn | Lys | Ile | Met 400 | His | Leu | Ser | Thr | Ser 405 | Asn |  |
| CTG | TCC | ATG | GGG | GAA | ATG | ACT | GCT | GGG | CAG | ATC | TGC | AAC | CTG | GTG | GCC | 1302 |
| Leu | Ser | Met | Gly 410 | Glu | Met | Thr | Ala | Gln 415 | Ile | Cys | Asn | Leu | Val 420 | Ala |  |  |
| ATC | GAC | ACC | AAC | CAG | CTC | ATG | TGG | TTT | TTC | TTC | TTA | TGC | CCA | AAC | CTC | 1350 |
| Ile | Asp | Thr | Asn 425 | Gln | Leu | Met | Trp | Phe 430 | Phe | Phe | Leu | Cys | Pro 435 | Asn | Leu |  |
| TGG | GCT | ATG | CCG | GTA | CAG | ATC | ATT | GTG | GGC | GTG | ATC | CTC | CTC | TAC | TAC | 1398 |
| Trp | Ala | Met 440 | Pro | Val | Gln | Ile | Ile 445 | Val | Gly | Val | Ile | Leu 450 | Leu | Tyr | Tyr |  |
| ATC | CTT | GGG | GTC | AGC | GCC | TTG | ATT | GGA | GCG | GCT | GTC | ATC | ATT | CTG | CTG | 1446 |
| Ile | Leu | Gly | Val 455 | Ser | Ala | Leu | Ile | Gly 460 | Ala | Ala | Val | Ile | Ile 465 | Leu | Leu 470 |  |
| GCT | CCT | GTA | CAG | TAC | TTT | GTG | GCC | ACC | AAG | CTG | TCC | CAG | GCA | CAG | CGG | 1494 |
| Ala | Pro | Val | Gln | Tyr | Phe | Val | Ala | Thr | Lys | Leu | Ser | Gln | Ala | Gln | Arg |  |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 475 |     |     |     |     | 480 |     |     |     |     | 485 |     |      |
| ACG | ACC | CTG | GAA | TAT | TCC | AAT | GAG | AGG | CTG | AAG | CAG | ACC | AAT | GAG | ATG | 1542 |
| Thr | Thr | Leu | Glu | Tyr | Ser | Asn | Glu | Arg | Leu | Lys | Gln | Thr | Asn | Glu | Met |      |
|     |     |     | 490 |     |     |     |     | 495 |     |     |     | 500 |     |     |     |      |
| CTC | CGG | GGC | ATC | AAG | TTG | CTC | AAG | CTC | TAT | GCG | TGG | GAG | AAC | ATC | TTC | 1590 |
| Leu | Arg | Gly | Ile | Lys | Leu | Leu | Lys | Leu | Tyr | Ala | Trp | Glu | Asn | Ile | Phe |      |
|     |     | 505 |     |     |     |     | 510 |     |     |     |     | 515 |     |     |     |      |
| TGC | TCC | AGG | GTG | GAG | AAG | ACA | CGC | AGG | AAG | GAA | ATG | ACC | AGC | CTC | AGG | 1638 |
| Cys | Ser | Arg | Val | Glu | Lys | Thr | Arg | Arg | Lys | Glu | Met | Thr | Ser | Leu | Arg |      |
|     | 520 |     |     |     |     | 525 |     |     |     |     | 530 |     |     |     |     |      |
| GCC | TTC | GCT | GTC | TAC | ACC | TCC | ATC | TCC | ATC | TTC | ATG | AAC | ACA | GCT | ATC | 1686 |
| Ala | Phe | Ala | Val | Tyr | Thr | Ser | Ile | Ser | Ile | Phe | Met | Asn | Thr | Ala | Ile |      |
| 535 |     |     |     |     | 540 |     |     |     |     | 545 |     |     |     |     | 550 |      |
| CCC | ATC | GCT | GCT | GTC | CTC | ATC | ACC | TTC | GTG | GGC | CAC | GTC | AGC | TTC | TTC | 1734 |
| Pro | Ile | Ala | Ala | Val | Leu | Ile | Thr | Phe | Val | Gly | His | Val | Ser | Phe | Phe |      |
|     |     |     |     | 555 |     |     |     |     | 560 |     |     |     |     | 565 |     |      |
| AAA | GAG | TCG | GAC | TTC | TCG | CCC | TCG | GTG | GCC | TTT | GCC | TCT | CTC | TCT | CTC | 1782 |
| Lys | Glu | Ser | Asp | Phe | Ser | Pro | Ser | Val | Ala | Phe | Ala | Ser | Leu | Ser | Leu |      |
|     |     |     | 570 |     |     |     |     | 575 |     |     |     |     | 580 |     |     |      |
| TTC | CAC | ATC | CTG | GTC | ACA | CCG | CTG | TTC | CTG | CTG | TCT | AGT | GTG | GTT | CGG | 1830 |
| Phe | His | Ile | Leu | Val | Thr | Pro | Leu | Phe | Leu | Leu | Ser | Ser | Val | Val | Arg |      |
|     |     | 585 |     |     |     |     | 590 |     |     |     |     | 595 |     |     |     |      |
| TCC | ACT | GTC | AAG | GCC | CTG | GTG | AGC | GTG | CAA | AAG | CTG | AGT | GAG | TTC | CTG | 1878 |
| Ser | Thr | Val | Lys | Ala | Leu | Val | Ser | Val | Gln | Lys | Leu | Ser | Glu | Phe | Leu |      |
|     | 600 |     |     |     |     | 605 |     |     |     |     | 610 |     |     |     |     |      |
| TCC | AGT | GCA | GAG | ATC | CGT | GAG | GAA | CAG | TGT | GCC | CCC | CGA | GAG | CCC | GCA | 1926 |
| Ser | Ser | Ala | Glu | Ile | Arg | Glu | Glu | Gln | Cys | Ala | Pro | Arg | Glu | Pro | Ala |      |
| 615 |     |     |     |     | 620 |     |     |     |     | 625 |     |     |     |     | 630 |      |
| CCC | CAA | GGC | CAA | GCG | GGC | AAG | TAC | CAG | GCG | GTG | CCC | CTC | AAG | GTC | GTA | 1974 |
| Pro | Gln | Gly | Gln | Ala | Gly | Lys | Tyr | Gln | Ala | Val | Pro | Leu | Lys | Val | Val |      |
|     |     |     |     | 635 |     |     |     |     | 640 |     |     |     |     | 645 |     |      |
| AAC | CGC | AAG | CGC | CCA | GCC | CGA | GAA | GAA | GTC | CGG | GAC | CTC | TTG | GGC | CCA | 2022 |
| Asn | Arg | Lys | Arg | Pro | Ala | Arg | Glu | Glu | Val | Arg | Asp | Leu | Leu | Gly | Pro |      |
|     |     |     | 650 |     |     |     |     | 655 |     |     |     |     | 660 |     |     |      |
| CTG | CAG | AGG | CTG | ACT | CCC | AGC | ACG | GAT | GGA | GAC | GCT | GAC | AAC | TTC | TGT | 2070 |
| Leu | Gln | Arg | Leu | Thr | Pro | Ser | Thr | Asp | Gly | Asp | Ala | Asp | Asn | Phe | Cys |      |
|     |     | 665 |     |     |     |     | 670 |     |     |     |     | 675 |     |     |     |      |
| GTC | CAG | ATC | ATC | GGA | GGC | TTC | TTC | ACC | TGG | ACC | CCT | GAT | GGA | ATC | CCC | 2118 |
| Val | Gln | Ile | Ile | Gly | Gly | Phe | Phe | Thr | Trp | Thr | Pro | Asp | Gly | Ile | Pro |      |
|     | 680 |     |     |     |     | 685 |     |     |     |     | 690 |     |     |     |     |      |
| ACC | CTG | TCC | AAC | ATC | ACC | ATC | CGT | ATC | CCC | CGA | GGT | CAG | CTG | ACC | ATG | 2166 |
| Thr | Leu | Ser | Asn | Ile | Thr | Ile | Arg | Ile | Pro | Arg | Gly | Gln | Leu | Thr | Met |      |
| 695 |     |     |     |     | 700 |     |     |     |     | 705 |     |     |     |     | 710 |      |
| ATC | GTG | GGG | CAG | GTG | GGC | TGT | GGC | AAG | TCC | TCG | CTC | CTT | CTG | GCC | ACC | 2214 |
| Ile | Val | Gly | Gln | Val | Gly | Cys | Gly | Lys | Ser | Ser | Leu | Leu | Leu | Ala | Thr |      |
|     |     |     |     | 715 |     |     |     |     | 720 |     |     |     |     | 725 |     |      |
| CTG | GGG | GAG | ATG | CAG | AAG | GTC | TCT | GGA | GCT | GTC | TTC | TGG | AAC | AGC | CTT | 2262 |
| Leu | Gly | Glu | Met | Gln | Lys | Val | Ser | Gly | Ala | Val | Phe | Trp | Asn | Ser | Leu |      |
|     |     |     | 730 |     |     |     |     | 735 |     |     |     |     | 740 |     |     |      |
| CCA | GAC | AGC | GAG | GGG | AGA | AGA | CCC | CAG | CAA | CCC | AGA | GCG | GGA | GAC | AGC | 2310 |
| Pro | Asp | Ser | Glu | Gly | Arg | Arg | Pro | Gln | Gln | Pro | Arg | Ala | Gly | Asp | Ser |      |
|     |     | 745 |     |     |     |     | 750 |     |     |     |     | 755 |     |     |     |      |
| GGC | CGA | TTC | GGA | TGC | CAG | GAG | CAG | AGG | CCC | TGT | GGC | TAC | GCA | TCT | CAG | 2358 |
| Gly | Arg | Phe | Gly | Cys | Gln | Glu | Gln | Arg | Pro | Cys | Gly | Tyr | Ala | Ser | Gln |      |
|     | 760 |     |     |     |     | 765 |     |     |     |     | 770 |     |     |     |     |      |
| AAA | CCA | TGG | CTG | CTA | AAT | GCC | ACT | GTG | GAG | GAG | AAC | ATC | ACC | TTC | GAG | 2406 |
| Lys | Pro | Trp | Leu | Leu | Asn | Ala | Thr | Val | Glu | Glu | Asn | Ile | Thr | Phe | Glu |      |
| 775 |     |     |     |     | 780 |     |     |     |     | 785 |     |     |     |     | 790 |      |
| AGT | CCC | TTC | AAT | AAG | CAA | CGG | TAC | AAG | ATG | GTC | ATC | GAA | GCC | TGC | TCC | 2454 |
| Ser | Pro | Phe | Asn | Lys | Gln | Arg | Tyr | Lys | Met | Val | Ile | Glu | Ala | Cys | Ser |      |

-continued

```
                      795                           800                           805
CTG  CAG  CCA  GAC  ATA  GAC  ATC  CTG  CCC  CAT  GGA  GAC  CAG  ACT  CAG  ATT    2502
Leu  Gln  Pro  Asp  Ile  Asp  Ile  Leu  Pro  His  Gly  Asp  Gln  Thr  Gln  Ile
                    810                           815                           820

GGG  GAA  CGA  GGC  ATC  AAC  TTG  AGT  ACT  GGT  GGT  CAG  CGT  CCA  GAT  CAG    2550
Gly  Glu  Arg  Gly  Ile  Asn  Leu  Ser  Thr  Gly  Gly  Gln  Arg  Pro  Asp  Gln
               825                           830                           835

TGT  AGA  CCC  GAG  CCC  TCT  ACC  AGC  ACA  CCA  ATG  ATT  GTC  TTT  TTG  GAT    2598
Cys  Arg  Pro  Glu  Pro  Ser  Thr  Ser  Thr  Pro  Met  Ile  Val  Phe  Leu  Asp
          840                           845                           850

GAC  CCT  TTC  TCG  GCT  CTG  GAT  GTC  CAT  CTG  AGT  GAC  CAC  CTA  ATG  CAG    2646
Asp  Pro  Phe  Ser  Ala  Leu  Asp  Val  His  Leu  Ser  Asp  His  Leu  Met  Gln
     855                           860                           865                870

GCT  GGC  ATC  CTC  GAG  CTG  CTC  CGG  GAT  GAC  AAG  AGG  ACA  GTG  GTC  TTG    2694
Ala  Gly  Ile  Leu  Glu  Leu  Leu  Arg  Asp  Asp  Lys  Arg  Thr  Val  Val  Leu
                         875                           880                      885

GTG  ACC  CAC  AAG  CTA  CAG  TAC  CTG  CCT  CAT  GCT  GAC  TGG  ATC  ATT  GCT    2742
Val  Thr  His  Lys  Leu  Gln  Tyr  Leu  Pro  His  Ala  Asp  Trp  Ile  Ile  Ala
                    890                           895                           900

ATG  AAG  GAT  GGC  ACC  ATT  CAG  AGG  GAG  GGG  ACA  CTC  AAG  GAC  TTC  CAG    2790
Met  Lys  Asp  Gly  Thr  Ile  Gln  Arg  Glu  Gly  Thr  Leu  Lys  Asp  Phe  Gln
          905                           910                           915

AGG  TCT  GAG  TGC  CAG  CTC  TTT  GAG  CAT  TGG  AAG  ACC  CTC  ATG  AAC  CGG    2838
Arg  Ser  Glu  Cys  Gln  Leu  Phe  Glu  His  Trp  Lys  Thr  Leu  Met  Asn  Arg
     920                           925                           930

CAG  GAC  CAA  GAG  CTG  GAG  AAG  GAG  ACA  GTC  ATG  GAG  AGA  AAA  GCC  CCA    2886
Gln  Asp  Gln  Glu  Leu  Glu  Lys  Glu  Thr  Val  Met  Glu  Arg  Lys  Ala  Pro
935                           940                           945                950

GAG  CCA  TCT  CAG  GGC  CTG  CCC  CGT  GCC  ATG  TCC  TCA  AGA  GAT  GGC  CTT    2934
Glu  Pro  Ser  Gln  Gly  Leu  Pro  Arg  Ala  Met  Ser  Ser  Arg  Asp  Gly  Leu
                    955                           960                           965

CTG  CTG  GAT  GAG  GAT  GAG  GAG  GAA  GAG  GAG  GCA  GCC  GAG  AGC  GAG  GAA    2982
Leu  Leu  Asp  Glu  Asp  Glu  Glu  Glu  Glu  Glu  Ala  Ala  Glu  Ser  Glu  Glu
               970                           975                           980

GAT  GAC  AAC  TTA  TCC  TCT  GTG  CTG  CAT  CAG  CGA  GCC  AAG  ATC  CCA  TGG    3030
Asp  Asp  Asn  Leu  Ser  Ser  Val  Leu  His  Gln  Arg  Ala  Lys  Ile  Pro  Trp
          985                           990                           995

CGA  GCC  TGC  ACC  AAG  TAT  TTG  TCC  TCT  GCT  GGC  ATC  CTG  CTC  CTG  TCC    3078
Arg  Ala  Cys  Thr  Lys  Tyr  Leu  Ser  Ser  Ala  Gly  Ile  Leu  Leu  Leu  Ser
     1000                          1005                          1010

CTG  CTT  GTC  TTC  TCC  CAG  CTG  CTC  AAG  CAC  ATG  GTC  TTG  GTG  GCC  ATT    3126
Leu  Leu  Val  Phe  Ser  Gln  Leu  Leu  Lys  His  Met  Val  Leu  Val  Ala  Ile
1015                          1020                          1025                1030

GAC  TAC  TGG  CTG  GCC  AAG  TGG  ACG  GAC  AGT  GCC  CTG  GTC  CTG  AGC  CCC    3174
Asp  Tyr  Trp  Leu  Ala  Lys  Trp  Thr  Asp  Ser  Ala  Leu  Val  Leu  Ser  Pro
                    1035                          1040                          1045

GCC  GCC  AGG  AAC  TGT  TCC  CTC  AGC  CAG  GAA  TGT  GCC  CTG  GAC  CAA  TCT    3222
Ala  Ala  Arg  Asn  Cys  Ser  Leu  Ser  Gln  Glu  Cys  Ala  Leu  Asp  Gln  Ser
               1050                          1055                          1060

GTC  TAT  GCC  ATG  GTA  TTC  ACC  GTG  CTC  TGC  AGC  CTG  GGT  ATC  GCG  CTG    3270
Val  Tyr  Ala  Met  Val  Phe  Thr  Val  Leu  Cys  Ser  Leu  Gly  Ile  Ala  Leu
          1065                          1070                          1075

TGC  CTT  GTC  ACC  TCT  GTC  ACT  GTG  GAG  TGG  ACG  GGA  CTG  AAG  GTG  GCC    3318
Cys  Leu  Val  Thr  Ser  Val  Thr  Val  Glu  Trp  Thr  Gly  Leu  Lys  Val  Ala
     1080                          1085                          1090

AAG  AGG  CTG  CAT  CGC  AGC  CTG  CTC  AAC  CGT  ATC  ATC  CTG  GCT  CCC  ATG    3366
Lys  Arg  Leu  His  Arg  Ser  Leu  Leu  Asn  Arg  Ile  Ile  Leu  Ala  Pro  Met
1095                          1100                          1105                1110

AGG  TTC  TTT  GAG  ACC  ACG  CCC  CTG  GGG  AGT  ATC  CTG  AAC  AGA  TTT  TCA    3414
Arg  Phe  Phe  Glu  Thr  Thr  Pro  Leu  Gly  Ser  Ile  Leu  Asn  Arg  Phe  Ser
```

|  |  |  |  |  |  |  |  |  |  |  |  |  |  |  |  |  |
|---|---|---|---|---|---|---|---|---|---|---|---|---|---|---|---|---|
|  |  |  |  | 1115 |  |  |  |  | 1120 |  |  |  |  | 1125 |  |  |
| TCT | GAC | TGT | AAC | ACC | ATT | GAC | CAG | CAT | ATC | CCG | TCC | ACG | CTG | GAG | TGC | 3462 |
| Ser | Asp | Cys | Asn 1130 | Thr | Ile | Asp | Gln | His 1135 | Ile | Pro | Ser | Thr | Leu 1140 | Glu | Cys |  |
| CTG | AGC | AGA | TCC | ACC | TTA | CTC | TGT | GTC | TCC | GCC | CTG | GCT | GTC | ATC | TCC | 3510 |
| Leu | Ser | Arg | Ser 1145 | Thr | Leu | Leu | Cys | Val 1150 | Ser | Ala | Leu | Ala | Val 1155 | Ile | Ser |  |
| TAC | GTC | ACG | CCT | GTG | TTC | CTA | GTG | GCC | CTC | TTA | CCC | CTC | GCC | GTC | GTG | 3558 |
| Tyr | Val | Thr | Pro 1160 | Val | Phe | Leu | Val | Ala 1165 | Leu | Leu | Pro | Leu | Ala 1170 | Val | Val |  |
| TGC | TAC | TTC | ATC | CAG | AAG | TAC | TTC | CGA | GTG | GCG | TCC | AGG | GAC | CTG | CAG | 3606 |
| Cys 1175 | Tyr | Phe | Ile | Gln | Lys 1180 | Tyr | Phe | Arg | Val | Ala 1185 | Ser | Arg | Asp | Leu | Gln 1190 |  |
| CAG | CTG | GAC | GAC | ACA | ACA | CAG | CTC | CCT | CTG | CTC | TCA | CAC | TTT | GCT | GAA | 3654 |
| Gln | Leu | Asp | Asp | Thr 1195 | Thr | Gln | Leu | Pro | Leu 1200 | Leu | Ser | His | Phe | Ala 1205 | Glu |  |
| ACT | GTG | GAA | GGA | CTC | ACC | ACC | ATC | CGT | GCC | TTC | AGG | TAC | GAG | GCC | CGG | 3702 |
| Thr | Val | Glu | Gly | Leu 1210 | Thr | Thr | Ile | Arg | Ala 1215 | Phe | Arg | Tyr | Glu | Ala 1220 | Arg |  |
| TTC | CAG | CAG | AAG | CTC | CTA | GAG | TAC | ACC | GAC | TCC | AAC | AAC | ATT | GCC | TCT | 3750 |
| Phe | Gln | Gln | Lys 1225 | Leu | Leu | Glu | Tyr | Thr 1230 | Asp | Ser | Asn | Asn | Ile 1235 | Ala | Ser |  |
| CTC | TTC | CTC | ACA | GCA | GCC | AAC | AGG | TGG | CTG | GAA | GTC | CGC | ATG | GAG | TAC | 3798 |
| Leu | Phe | Leu | Thr 1240 | Ala | Ala | Asn | Arg | Trp 1245 | Leu | Glu | Val | Arg | Met 1250 | Glu | Tyr |  |
| ATC | GGA | GCA | TGC | GTG | GTA | CTC | ATC | GCC | GCT | GCC | ACC | TCC | ATC | TCC | AAC | 3846 |
| Ile 1255 | Gly | Ala | Cys | Val | Val 1260 | Leu | Ile | Ala | Ala | Ala 1265 | Thr | Ser | Ile | Ser | Asn 1270 |  |
| TCC | CTA | CAC | AGG | GAG | CTC | TCA | GCC | GGC | CTA | GTA | GGC | CTG | GGC | CTC | ACC | 3894 |
| Ser | Leu | His | Arg | Glu 1275 | Leu | Ser | Ala | Gly | Leu 1280 | Val | Gly | Leu | Gly | Leu 1285 | Thr |  |
| TAT | GCC | TTG | ATG | ATT | GGG | ATC | TGC | GGC | CGC | ACA | GGC | AGT | GGA | AAA | TCC | 3942 |
| Tyr | Ala | Leu | Met | Ile 1290 | Gly | Ile | Cys | Gly | Arg 1295 | Thr | Gly | Ser | Gly | Lys 1300 | Ser |  |
| TCC | TTC | TCT | CTC | GCC | TTT | TTC | CGA | ATG | GTG | GAT | ATG | TTT | GAA | GGG | CGT | 3990 |
| Ser | Phe | Ser | Leu 1305 | Ala | Phe | Phe | Arg | Met 1310 | Val | Asp | Met | Phe | Glu 1315 | Gly | Arg |  |
| ATC | ATC | ATC | GAT | GGC | ATT | GAC | ATC | GCC | AAG | CTG | CCG | CTG | CAC | ACG | CTC | 4038 |
| Ile | Ile | Ile | Asp 1320 | Gly | Ile | Asp | Ile | Ala 1325 | Lys | Leu | Pro | Leu | His 1330 | Thr | Leu |  |
| CGC | TCA | CGC | CTG | TCT | ATC | ATC | CTA | CAG | GAC | CCT | GTT | CTC | TTC | AGT | GGT | 4086 |
| Arg 1335 | Ser | Arg | Leu | Ser | Ile 1340 | Ile | Leu | Gln | Asp | Pro 1345 | Val | Leu | Phe | Ser | Gly 1350 |  |
| ACC | ATC | AGA | TTC | AAC | CTG | GAC | CCA | GAG | AAG | AAA | TGC | TCA | GAC | AGC | ACG | 4134 |
| Thr | Ile | Arg | Phe | Asn 1355 | Leu | Asp | Pro | Glu | Lys 1360 | Lys | Cys | Ser | Asp | Ser 1365 | Thr |  |
| CTG | TGG | GAG | GCT | CTG | GAG | ATC | GCT | CAG | CTG | AAG | CTG | GTG | GTG | AAG | GCC | 4182 |
| Leu | Trp | Glu | Ala | Leu 1370 | Glu | Ile | Ala | Gln | Leu 1375 | Lys | Leu | Val | Val | Lys 1380 | Ala |  |
| CTG | CCA | GGA | GGC | CTG | GAT | GCC | ATC | ATC | ACG | GAA | GGA | GGG | GAG | AAT | TTT | 4230 |
| Leu | Pro | Gly | Gly 1385 | Leu | Asp | Ala | Ile | Ile 1390 | Thr | Glu | Gly | Gly | Glu 1395 | Asn | Phe |  |
| AGC | CAG | GGC | CAG | AGG | CAG | CTG | TTC | TGC | CTG | GCC | CGG | GCC | TTT | GTG | AGG | 4278 |
| Ser | Gln | Gly | Gln | Arg 1400 | Gln | Leu | Phe | Cys | Leu 1405 | Ala | Arg | Ala | Phe | Val 1410 | Arg |  |
| AAG | ACC | AGC | ATC | TTC | ATC | ATG | GAT | GAA | GCA | ACT | GCC | TCC | ATC | GAC | ATG | 4326 |
| Lys 1415 | Thr | Ser | Ile | Phe | Ile 1420 | Met | Asp | Glu | Ala | Thr 1425 | Ala | Ser | Ile | Asp | Met 1430 |  |
| GCT | ACG | GAA | AAT | ATC | CTC | CAG | AAG | GTG | GTG | ATG | ACA | GCC | TTC | GCA | GAC | 4374 |
| Ala | Thr | Glu | Asn | Ile | Leu | Gln | Lys | Val | Val | Met | Thr | Ala | Phe | Ala | Asp |  |

```
                           1 4 3 5                        1 4 4 0                        1 4 4 5
CGC  ACC  GTG  GTC  ACC  ATC  GCG  CAC  CGC  GTG  CAC  ACC  ATC  CTG  AGT  GCA              4 4 2 2
Arg  Thr  Val  Val  Thr  Ile  Ala  His  Arg  Val  His  Thr  Ile  Leu  Ser  Ala
          1 4 5 0                        1 4 5 5                        1 4 6 0

GAC  CTA  GTG  ATG  GTC  CTG  AAG  AGG  GGC  GCG  ATC  CTG  GAG  TTC  GAC  AAG              4 4 7 0
Asp  Leu  Val  Met  Val  Leu  Lys  Arg  Gly  Ala  Ile  Leu  Glu  Phe  Asp  Lys
          1 4 6 5                        1 4 7 0                        1 4 7 5

CCG  GAA  AAG  CTT  CTC  AGC  CAG  AAG  GAC  AGC  GTC  TTT  GCC  TCC  TTT  GTC              4 5 1 8
Pro  Glu  Lys  Leu  Leu  Ser  Gln  Lys  Asp  Ser  Val  Phe  Ala  Ser  Phe  Val
          1 4 8 0                        1 4 8 5                        1 4 9 0

CGC  GCG  GAC  AAA  TGACCAGCCA  GCGCCAAAGT  GCCACCCCAC  ACCTCACCTG                          4 5 7 0
Arg  Ala  Asp  Lys
1 4 9 5

CTTGCCATGG  ATTTCTTACT  GTAAATCACT  TGTAAATAAA  GAAACTAATT  CTTTGCTAAA                       4 6 3 0

AAAAA                                                                                        4 6 3 5
```

( 2 ) INFORMATION FOR SEQ ID NO:28:

( i ) SEQUENCE CHARACTERISTICS:
        ( A ) LENGTH: 1498 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Met  Pro  Leu  Ala  Phe  Cys  Gly  Thr  Glu  Asn  His  Ser  Ala  Ala  Tyr  Arg
 1              5                       1 0                      1 5

Val  Asp  Gln  Gly  Val  Leu  Asn  Asn  Gly  Cys  Phe  Val  Asp  Ala  Leu  Asn
               2 0                      2 5                      3 0

Val  Val  Pro  His  Val  Phe  Leu  Leu  Phe  Ile  Thr  Phe  Pro  Ile  Leu  Phe
               3 5                      4 0                      4 5

Ile  Gly  Trp  Gly  Ser  Gln  Ser  Ser  Lys  Val  His  Ile  His  His  Ser  Thr
          5 0                      5 5                      6 0

Trp  Leu  His  Phe  Pro  Gly  His  Asn  Leu  Arg  Trp  Ile  Leu  Thr  Phe  Ile
6 5                                7 0                      7 5                      8 0

Leu  Leu  Phe  Val  Leu  Val  Cys  Glu  Ile  Ala  Glu  Gly  Ile  Leu  Ser  Asp
                    8 5                      9 0                      9 5

Gly  Val  Thr  Glu  Ser  Arg  His  Leu  His  Leu  Tyr  Met  Pro  Ala  Gly  Met
               1 0 0                     1 0 5                     1 1 0

Ala  Phe  Met  Ala  Ala  Ile  Thr  Ser  Val  Val  Tyr  Tyr  His  Asn  Ile  Glu
               1 1 5                     1 2 0                     1 2 5

Thr  Ser  Asn  Phe  Pro  Lys  Leu  Leu  Ile  Ala  Leu  Leu  Ile  Tyr  Trp  Thr
          1 3 0                     1 3 5                     1 4 0

Leu  Ala  Phe  Ile  Thr  Lys  Thr  Ile  Lys  Phe  Val  Lys  Phe  Tyr  Asp  His
1 4 5                               1 5 0                     1 5 5                     1 6 0

Ala  Ile  Gly  Phe  Ser  Gln  Leu  Arg  Phe  Cys  Leu  Thr  Gly  Leu  Leu  Val
                    1 6 5                     1 7 0                     1 7 5

Ile  Leu  Tyr  Gly  Met  Leu  Leu  Leu  Val  Glu  Val  Asn  Val  Ile  Arg  Val
               1 8 0                     1 8 5                     1 9 0

Arg  Arg  Tyr  Val  Phe  Phe  Lys  Thr  Pro  Arg  Glu  Val  Lys  Pro  Pro  Glu
               1 9 5                     2 0 0                     2 0 5

Asp  Leu  Gln  Asp  Leu  Gly  Val  Arg  Phe  Leu  Gln  Pro  Phe  Val  Asn  Leu
          2 1 0                     2 1 5                     2 2 0

Leu  Ser  Lys  Gly  Thr  Tyr  Trp  Trp  Met  Asn  Ala  Phe  Ile  Lys  Thr  Ala
2 2 5                               2 3 0                     2 3 5                     2 4 0

His  Lys  Lys  Pro  Ile  Asp  Leu  Arg  Ala  Ile  Gly  Lys  Leu  Pro  Ile  Ala
```

-continued

|     |     |     | 245 |     |     |     | 250 |     |     |     | 255 |     |
|-----|-----|-----|-----|-----|-----|-----|-----|-----|-----|-----|-----|-----|

Met Arg Ala Leu Thr Asn Tyr Gln Leu Cys Leu Ala Phe Asp Ala
            260                 265             270
Gln Ala Arg Lys Asp Thr Gln Ser Gln Gln Gly Ala Arg Ala Ile Trp
        275                 280                 285
Arg Ala Leu Cys His Ala Phe Gly Arg Arg Leu Val Leu Ser Ser Thr
        290             295                 300
Phe Arg Ile Leu Ala Asp Leu Leu Gly Phe Ala Gly Pro Leu Cys Ile
305                 310             315                 320
Phe Gly Ile Val Asp His Leu Gly Lys Glu Asn His Val Phe Gln Pro
                325             330                 335
Lys Thr Gln Phe Leu Gly Val Tyr Phe Val Ser Ser Gln Glu Phe Leu
            340             345                 350
Gly Asn Ala Tyr Val Leu Ala Val Leu Leu Phe Leu Ala Leu Leu Leu
        355             360             365
Gln Arg Thr Phe Leu Gln Ala Ser Tyr Tyr Val Ala Ile Glu Thr Gly
    370             375             380
Ile Asn Leu Arg Gly Ala Ile Gln Thr Lys Ile Tyr Asn Lys Ile Met
385             390             395                 400
His Leu Ser Thr Ser Asn Leu Ser Met Gly Glu Met Thr Ala Gly Gln
            405             410             415
Ile Cys Asn Leu Val Ala Ile Asp Thr Asn Gln Leu Met Trp Phe Phe
        420             425             430
Phe Leu Cys Pro Asn Leu Trp Ala Met Pro Val Gln Ile Ile Val Gly
        435             440             445
Val Ile Leu Leu Tyr Tyr Ile Leu Gly Val Ser Ala Leu Ile Gly Ala
    450             455             460
Ala Val Ile Ile Leu Leu Ala Pro Val Gln Tyr Phe Val Ala Thr Lys
465             470             475                 480
Leu Ser Gln Ala Gln Arg Thr Thr Leu Glu Tyr Ser Asn Glu Arg Leu
            485             490             495
Lys Gln Thr Asn Glu Met Leu Arg Gly Ile Lys Leu Leu Lys Leu Tyr
            500             505             510
Ala Trp Glu Asn Ile Phe Cys Ser Arg Val Glu Lys Thr Arg Arg Lys
        515             520             525
Glu Met Thr Ser Leu Arg Ala Phe Ala Val Tyr Thr Ser Ile Ser Ile
    530             535             540
Phe Met Asn Thr Ala Ile Pro Ile Ala Ala Val Leu Ile Thr Phe Val
545             550             555             560
Gly His Val Ser Phe Phe Lys Glu Ser Asp Phe Ser Pro Ser Val Ala
            565             570             575
Phe Ala Ser Leu Ser Leu Phe His Ile Leu Val Thr Pro Leu Phe Leu
            580             585             590
Leu Ser Ser Val Val Arg Ser Thr Val Lys Ala Leu Val Ser Val Gln
        595             600             605
Lys Leu Ser Glu Phe Leu Ser Ser Ala Glu Ile Arg Glu Glu Gln Cys
    610             615             620
Ala Pro Arg Glu Pro Ala Pro Gln Gly Gln Ala Gly Lys Tyr Gln Ala
625             630             635             640
Val Pro Leu Lys Val Val Asn Arg Lys Arg Pro Ala Arg Glu Glu Val
            645             650             655
Arg Asp Leu Leu Gly Pro Leu Gln Arg Leu Thr Pro Ser Thr Asp Gly
            660             665             670

```
Asp Ala Asp Asn Phe Cys Val Gln Ile Ile Gly Gly Phe Phe Thr Trp
            675             680             685

Thr Pro Asp Gly Ile Pro Thr Leu Ser Asn Ile Thr Ile Arg Ile Pro
        690             695             700

Arg Gly Gln Leu Thr Met Ile Val Gly Gln Val Gly Cys Gly Lys Ser
705             710             715             720

Ser Leu Leu Leu Ala Thr Leu Gly Glu Met Gln Lys Val Ser Gly Ala
                725             730             735

Val Phe Trp Asn Ser Leu Pro Asp Ser Glu Gly Arg Arg Pro Gln Gln
            740             745             750

Pro Arg Ala Gly Asp Ser Gly Arg Phe Gly Cys Gln Glu Gln Arg Pro
        755             760             765

Cys Gly Tyr Ala Ser Gln Lys Pro Trp Leu Leu Asn Ala Thr Val Glu
    770             775             780

Glu Asn Ile Thr Phe Glu Ser Pro Phe Asn Lys Gln Arg Tyr Lys Met
785             790             795             800

Val Ile Glu Ala Cys Ser Leu Gln Pro Asp Ile Asp Ile Leu Pro His
            805             810             815

Gly Asp Gln Thr Gln Ile Gly Glu Arg Gly Ile Asn Leu Ser Thr Gly
            820             825             830

Gly Gln Arg Pro Asp Gln Cys Arg Pro Glu Pro Ser Thr Ser Thr Pro
        835             840             845

Met Ile Val Phe Leu Asp Asp Pro Phe Ser Ala Leu Asp Val His Leu
850             855             860

Ser Asp His Leu Met Gln Ala Gly Ile Leu Glu Leu Leu Arg Asp Asp
865             870             875             880

Lys Arg Thr Val Val Leu Val Thr His Lys Leu Gln Tyr Leu Pro His
                885             890             895

Ala Asp Trp Ile Ile Ala Met Lys Asp Gly Thr Ile Gln Arg Glu Gly
            900             905             910

Thr Leu Lys Asp Phe Gln Arg Ser Glu Cys Gln Leu Phe Glu His Trp
        915             920             925

Lys Thr Leu Met Asn Arg Gln Asp Gln Glu Leu Glu Lys Glu Thr Val
    930             935             940

Met Glu Arg Lys Ala Pro Glu Pro Ser Gln Gly Leu Pro Arg Ala Met
945             950             955             960

Ser Ser Arg Asp Gly Leu Leu Leu Asp Glu Asp Glu Glu Glu Glu Glu
            965             970             975

Ala Ala Glu Ser Glu Glu Asp Asp Asn Leu Ser Ser Val Leu His Gln
            980             985             990

Arg Ala Lys Ile Pro Trp Arg Ala Cys Thr Lys Tyr Leu Ser Ser Ala
        995             1000            1005

Gly Ile Leu Leu Leu Ser Leu Leu Val Phe Ser Gln Leu Leu Lys His
    1010            1015            1020

Met Val Leu Val Ala Ile Asp Tyr Trp Leu Ala Lys Trp Thr Asp Ser
1025            1030            1035            1040

Ala Leu Val Leu Ser Pro Ala Ala Arg Asn Cys Ser Leu Ser Gln Glu
                1045            1050            1055

Cys Ala Leu Asp Gln Ser Val Tyr Ala Met Val Phe Thr Val Leu Cys
            1060            1065            1070

Ser Leu Gly Ile Ala Leu Cys Leu Val Thr Ser Val Thr Val Glu Trp
            1075            1080            1085

Thr Gly Leu Lys Val Ala Lys Arg Leu His Arg Ser Leu Leu Asn Arg
        1090            1095            1100
```

Ile Ile Leu Ala Pro Met Arg Phe Phe Glu Thr Thr Pro Leu Gly Ser
1105                1110                1115                1120

Ile Leu Asn Arg Phe Ser Ser Asp Cys Asn Thr Ile Asp Gln His Ile
            1125                1130                1135

Pro Ser Thr Leu Glu Cys Leu Ser Arg Ser Thr Leu Leu Cys Val Ser
            1140                1145                1150

Ala Leu Ala Val Ile Ser Tyr Val Thr Pro Val Phe Leu Val Ala Leu
            1155                1160                1165

Leu Pro Leu Ala Val Val Cys Tyr Phe Ile Gln Lys Tyr Phe Arg Val
1170                1175                1180

Ala Ser Arg Asp Leu Gln Gln Leu Asp Asp Thr Thr Gln Leu Pro Leu
1185                1190                1195                1200

Leu Ser His Phe Ala Glu Thr Val Glu Gly Leu Thr Thr Ile Arg Ala
                1205                1210                1215

Phe Arg Tyr Glu Ala Arg Phe Gln Gln Lys Leu Leu Glu Tyr Thr Asp
            1220                1225                1230

Ser Asn Asn Ile Ala Ser Leu Phe Leu Thr Ala Ala Asn Arg Trp Leu
            1235                1240                1245

Glu Val Arg Met Glu Tyr Ile Gly Ala Cys Val Val Leu Ile Ala Ala
    1250                1255                1260

Ala Thr Ser Ile Ser Asn Ser Leu His Arg Glu Leu Ser Ala Gly Leu
1265                1270                1275                1280

Val Gly Leu Gly Leu Thr Tyr Ala Leu Met Ile Gly Ile Cys Gly Arg
                1285                1290                1295

Thr Gly Ser Gly Lys Ser Ser Phe Ser Leu Ala Phe Phe Arg Met Val
                1300                1305                1310

Asp Met Phe Glu Gly Arg Ile Ile Ile Asp Gly Ile Asp Ile Ala Lys
            1315                1320                1325

Leu Pro Leu His Thr Leu Arg Ser Arg Leu Ser Ile Ile Leu Gln Asp
            1330                1335                1340

Pro Val Leu Phe Ser Gly Thr Ile Arg Phe Asn Leu Asp Pro Glu Lys
1345                1350                1355                1360

Lys Cys Ser Asp Ser Thr Leu Trp Glu Ala Leu Glu Ile Ala Gln Leu
                1365                1370                1375

Lys Leu Val Val Lys Ala Leu Pro Gly Gly Leu Asp Ala Ile Ile Thr
                1380                1385                1390

Glu Gly Gly Glu Asn Phe Ser Gln Gly Gln Arg Gln Leu Phe Cys Leu
                1395                1400                1405

Ala Arg Ala Phe Val Arg Lys Thr Ser Ile Phe Ile Met Asp Glu Ala
            1410                1415                1420

Thr Ala Ser Ile Asp Met Ala Thr Glu Asn Ile Leu Gln Lys Val Val
1425                1430                1435                1440

Met Thr Ala Phe Ala Asp Arg Thr Val Val Thr Ile Ala His Arg Val
                1445                1450                1455

His Thr Ile Leu Ser Ala Asp Leu Val Met Val Leu Lys Arg Gly Ala
            1460                1465                1470

Ile Leu Glu Phe Asp Lys Pro Glu Lys Leu Leu Ser Gln Lys Asp Ser
            1475                1480                1485

Val Phe Ala Ser Phe Val Arg Ala Asp Lys
    1490                1495

( 2 ) INFORMATION FOR SEQ ID NO:29:

( i ) SEQUENCE CHARACTERISTICS:

(A) LENGTH: 1498 amino acids
(B) TYPE: amino acid
(D) TOPOLOGY: linear (ii) MOLECULE TYPE: protein (xi) SEQUENCE DESCRIPTION: SEQ ID NO:29:

```
Met Pro Leu Ala Phe Cys Gly Thr Glu Asn His Ser Ala Ala Tyr Arg
 1               5                  10                  15

Val Asp Gln Gly Val Leu Asn Asn Gly Cys Phe Val Asp Ala Leu Asn
                20                  25                  30

Val Val Pro His Val Phe Leu Leu Phe Ile Thr Phe Pro Ile Leu Phe
            35                  40                  45

Ile Gly Trp Gly Ser Gln Ser Ser Lys Val His Ile His Ser Thr
        50                  55                  60

Trp Leu His Phe Pro Gly His Asn Leu Arg Trp Ile Leu Thr Phe Ile
 65                  70                  75                  80

Leu Leu Phe Val Leu Val Cys Glu Ile Ala Glu Gly Ile Leu Ser Asp
                85                  90                  95

Gly Val Thr Glu Ser Arg His Leu His Leu Tyr Met Pro Ala Gly Met
                100                 105                 110

Ala Phe Met Ala Ala Ile Thr Ser Val Val Tyr Tyr His Asn Ile Glu
            115                 120                 125

Thr Ser Asn Phe Pro Lys Leu Leu Ile Ala Leu Leu Ile Tyr Trp Thr
    130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Leu Val Glu Val Asn Val Ile Arg Val
            180                 185                 190

Arg Arg Tyr Ile Phe Phe Lys Thr Pro Arg Glu Val Lys Pro Pro Glu
        195                 200                 205

Asp Leu Gln Asp Leu Gly Val Arg Phe Leu Gln Pro Phe Val Asn Leu
    210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Ala Lys Leu Pro Ile Ala
                245                 250                 255

Met Arg Ala Leu Thr Asn Tyr Gln Arg Leu Cys Val Ala Phe Asp Ala
            260                 265                 270

Gln Ala Arg Lys Asp Thr Gln Ser Pro Gln Gly Ala Arg Ala Ile Trp
        275                 280                 285

Arg Ala Leu Cys His Ala Phe Gly Arg Arg Leu Ile Leu Ser Ser Thr
    290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

Gly Asn Ala Tyr Val Leu Ala Val Leu Leu Phe Leu Ala Leu Leu Leu
        355                 360                 365

Gln Arg Thr Phe Leu Gln Ala Ser Tyr Tyr Val Ala Ile Glu Thr Gly
    370                 375                 380
```

```
Ile  Asn  Leu  Arg  Gly  Ala  Ile  Gln  Thr  Lys  Ile  Tyr  Asn  Lys  Ile  Met
385                      390                 395                           400

His  Met  Ser  Thr  Ser  Asn  Leu  Ser  Met  Gly  Glu  Met  Thr  Ala  Gly  Gln
                    405                 410                      415

Ile  Cys  Asn  Leu  Val  Ala  Ile  Asp  Thr  Asn  Gln  Leu  Met  Trp  Phe  Phe
               420                 425                           430

Phe  Leu  Cys  Pro  Asn  Leu  Trp  Thr  Met  Pro  Val  Gln  Ile  Ile  Val  Gly
          435                      440                      445

Val  Ile  Leu  Leu  Tyr  Tyr  Ile  Leu  Gly  Val  Ser  Ala  Leu  Ile  Gly  Ala
          450                 455                 460

Ala  Val  Ile  Ile  Leu  Leu  Ala  Pro  Val  Gln  Tyr  Phe  Val  Ala  Thr  Lys
465                      470                 475                           480

Leu  Ser  Gln  Ala  Gln  Arg  Thr  Thr  Leu  Glu  His  Ser  Asn  Glu  Arg  Leu
                    485                 490                           495

Lys  Gln  Thr  Asn  Glu  Met  Leu  Arg  Gly  Met  Lys  Leu  Leu  Lys  Leu  Tyr
               500                 505                      510

Ala  Trp  Glu  Ser  Ile  Phe  Cys  Ser  Arg  Val  Glu  Val  Thr  Arg  Arg  Lys
          515                      520                      525

Glu  Met  Thr  Ser  Leu  Arg  Ala  Phe  Ala  Val  Tyr  Thr  Ser  Ile  Ser  Ile
     530                      535                      540

Phe  Met  Asn  Thr  Ala  Ile  Pro  Ile  Ala  Ala  Val  Leu  Ile  Thr  Phe  Val
545                      550                 555                           560

Gly  His  Val  Ser  Phe  Phe  Lys  Glu  Ser  Asp  Leu  Ser  Pro  Ser  Val  Ala
                    565                 570                      575

Phe  Ala  Ser  Leu  Ser  Leu  Phe  His  Ile  Leu  Val  Thr  Pro  Leu  Phe  Leu
               580                 585                      590

Leu  Ser  Ser  Val  Val  Arg  Ser  Thr  Val  Lys  Ala  Leu  Val  Ser  Val  Gln
          595                      600                      605

Lys  Leu  Ser  Glu  Phe  Leu  Ser  Ser  Ala  Glu  Ile  Arg  Glu  Glu  Gln  Cys
610                      615                      620

Ala  Pro  Arg  Glu  Pro  Ala  Pro  Gln  Gly  Gln  Ala  Gly  Lys  Tyr  Gln  Ala
625                      630                 635                           640

Val  Pro  Leu  Lys  Val  Val  Asn  Arg  Lys  Arg  Pro  Ala  Arg  Glu  Glu  Val
               645                      650                      655

Arg  Asp  Leu  Leu  Gly  Pro  Leu  Gln  Arg  Leu  Ala  Pro  Ser  Met  Asp  Gly
               660                      665                      670

Asp  Ala  Asp  Asn  Phe  Cys  Val  Gln  Ile  Ile  Gly  Gly  Phe  Phe  Thr  Trp
          675                      680                 685

Thr  Pro  Asp  Gly  Ile  Pro  Thr  Leu  Ser  Asn  Ile  Thr  Ile  Arg  Ile  Pro
     690                      695                 700

Arg  Gly  Gln  Leu  Thr  Met  Ile  Val  Gly  Gln  Val  Gly  Cys  Gly  Lys  Ser
705                      710                 715                           720

Ser  Leu  Leu  Leu  Ala  Thr  Leu  Gly  Glu  Met  Gln  Lys  Val  Ser  Gly  Ala
                    725                 730                           735

Val  Phe  Trp  Asn  Ser  Asn  Leu  Pro  Asp  Ser  Glu  Gly  Arg  Gly  Pro  Gln
               740                 745                      750

Gln  Pro  Arg  Ala  Gly  Asp  Ser  Ser  Trp  Leu  Gly  Tyr  Gln  Glu  Gln  Arg
          755                      760                      765

Pro  Arg  Gly  Tyr  Ala  Ser  Gln  Lys  Pro  Trp  Leu  Leu  Asn  Ala  Thr  Val
     770                      775                      780

Glu  Glu  Asn  Ile  Thr  Phe  Glu  Ser  Pro  Phe  Asn  Pro  Gln  Arg  Tyr  Lys
785                      790                      795                      800

Met  Val  Ile  Glu  Ala  Cys  Ser  Leu  Gln  Pro  Asp  Ile  Asp  Ile  Leu  Pro
                    805                      810                      815
```

-continued

```
His  Gly  Asp  Gln  Thr  Gln  Ile  Gly  Glu  Arg  Gly  Ile  Asn  Leu  Ser  Gly
               820                      825                     830

Gly  Gln  Arg  Pro  Asp  Gln  Cys  Gly  Pro  Glu  Pro  Ser  Thr  Ser  Arg  Pro
               835                      840                     845

Met  Phe  Val  Phe  Leu  Asp  Asp  Pro  Phe  Ser  Ala  Leu  Asp  Val  His  Leu
850                           855                     860

Ser  Asp  His  Leu  Met  Gln  Ala  Gly  Ile  Leu  Glu  Leu  Leu  Arg  Asp  Asp
865                      870                     875                          880

Lys  Arg  Thr  Val  Val  Leu  Val  Thr  His  Lys  Leu  Gln  Tyr  Leu  Pro  His
                    885                      890                     895

Ala  Asp  Trp  Ile  Ile  Ala  Met  Lys  Asp  Gly  Thr  Ile  Gln  Arg  Glu  Gly
               900                      905                     910

Thr  Leu  Lys  Asp  Phe  Gln  Arg  Ser  Glu  Cys  Gln  Leu  Phe  Glu  His  Trp
               915                      920                     925

Lys  Thr  Leu  Met  Asn  Arg  Gln  Asp  Gln  Glu  Leu  Glu  Lys  Glu  Thr  Val
          930                      935                     940

Met  Glu  Arg  Lys  Ala  Ser  Glu  Pro  Ser  Gln  Gly  Leu  Pro  Arg  Ala  Met
945                      950                     955                          960

Ser  Ser  Arg  Asp  Gly  Leu  Leu  Leu  Asp  Glu  Glu  Glu  Glu  Glu  Glu  Glu
               965                      970                     975

Ala  Ala  Glu  Ser  Glu  Glu  Asp  Asp  Asn  Leu  Ser  Ser  Val  Leu  His  Gln
               980                      985                     990

Arg  Ala  Lys  Ile  Pro  Trp  Arg  Ala  Cys  Thr  Lys  Tyr  Leu  Ser  Ser  Ala
               995                      1000                    1005

Gly  Ile  Leu  Leu  Leu  Ser  Leu  Leu  Val  Phe  Ser  Gln  Leu  Leu  Lys  His
               1010                     1015                    1020

Met  Val  Leu  Val  Ala  Ile  Asp  Tyr  Trp  Leu  Ala  Lys  Trp  Thr  Asp  Ser
1025                     1030                    1035                         1040

Ala  Leu  Val  Leu  Ser  Pro  Ala  Ala  Arg  Asn  Cys  Ser  Leu  Ser  Gln  Glu
               1045                     1050                    1055

Cys  Asp  Leu  Asp  Gln  Ser  Val  Tyr  Ala  Met  Val  Phe  Thr  Leu  Leu  Cys
               1060                     1065                    1070

Ser  Leu  Gly  Ile  Val  Leu  Cys  Leu  Val  Thr  Ser  Val  Thr  Val  Glu  Trp
               1075                     1080                    1085

Thr  Gly  Leu  Lys  Val  Ala  Lys  Arg  Leu  His  Arg  Ser  Leu  Leu  Asn  Arg
               1090                     1095                    1100

Ile  Ile  Leu  Ala  Pro  Met  Arg  Phe  Phe  Glu  Thr  Thr  Pro  Leu  Gly  Ser
1105                     1110                    1115                         1120

Ile  Leu  Asn  Arg  Phe  Ser  Ser  Asp  Cys  Asn  Thr  Ile  Asp  Gln  His  Ile
               1125                     1130                    1135

Pro  Ser  Thr  Leu  Glu  Cys  Leu  Ser  Arg  Ser  Thr  Leu  Leu  Cys  Val  Ser
               1140                     1145                    1150

Ala  Leu  Thr  Val  Ile  Ser  Tyr  Val  Thr  Pro  Val  Phe  Leu  Val  Ala  Leu
               1155                     1160                    1165

Leu  Pro  Leu  Ala  Val  Val  Cys  Tyr  Phe  Ile  Gln  Lys  Tyr  Phe  Arg  Val
               1170                     1175                    1180

Ala  Ser  Arg  Asp  Leu  Gln  Gln  Leu  Asp  Asp  Thr  Thr  Gln  Leu  Pro  Leu
1185                     1190                    1195                         1200

Val  Ser  His  Phe  Ala  Glu  Thr  Val  Glu  Gly  Leu  Thr  Thr  Ile  Arg  Ala
               1205                     1210                    1215

Phe  Arg  Tyr  Glu  Ala  Arg  Phe  Gln  Gln  Lys  Leu  Leu  Glu  Tyr  Thr  Asp
               1220                     1225                    1230

Ser  Asn  Asn  Ile  Ala  Ser  Leu  Phe  Leu  Thr  Ala  Ala  Asn  Arg  Trp  Leu
```

```
                    1235                          1240                          1245
         Glu  Val  Cys  Met  Glu  Tyr  Ile  Gly  Ala  Cys  Val  Val  Leu  Ile  Ala  Ala
                    1250                          1255                     1260

Ala  Thr  Ser  Ile  Ser  Asn  Ser  Leu  His  Arg  Glu  Leu  Ser  Ala  Gly  Leu
         1265                          1270                     1275                          1280

Val  Gly  Leu  Gly  Leu  Thr  Tyr  Ala  Leu  Met  Ile  Gly  Ile  Cys  Gly  Arg
                              1285                          1290                     1295

Thr  Ala  Ser  Gly  Lys  Ser  Ser  Phe  Ser  Leu  Ala  Phe  Phe  Arg  Met  Val
                         1300                          1305                     1310

Asp  Met  Phe  Glu  Gly  Arg  Ile  Ile  Ile  Asp  Gly  Ile  Asp  Ile  Ala  Lys
                    1315                          1320                     1325

Leu  Pro  Leu  His  Thr  Leu  Arg  Ser  Arg  Leu  Ser  Ile  Ile  Leu  Gln  Asp
              1330                          1335                     1340

Pro  Val  Leu  Phe  Ser  Gly  Thr  Ile  Arg  Phe  Asn  Leu  Asp  Pro  Glu  Lys
         1345                          1350                          1355                     1360

Lys  Cys  Ser  Asp  Ser  Thr  Leu  Trp  Glu  Ala  Leu  Glu  Ile  Ala  Gln  Leu
                              1365                          1370                          1375

Lys  Leu  Val  Val  Lys  Ala  Leu  Pro  Gly  Gly  Leu  Asp  Ala  Ile  Ile  Thr
                         1380                          1385                     1390

Glu  Gly  Gly  Glu  Asn  Phe  Ser  Gln  Gly  Gln  Arg  Gln  Leu  Phe  Cys  Leu
                         1395                          1400                     1405

Ala  Arg  Ala  Phe  Val  Arg  Lys  Thr  Ser  Ile  Phe  Ile  Met  Asp  Glu  Ala
              1410                          1415                     1420

Thr  Ala  Ser  Ile  Asp  Met  Ala  Thr  Glu  Asn  Ile  Leu  Gln  Lys  Val  Val
         1425                          1430                          1435                          1440

Met  Thr  Ala  Phe  Ala  Asp  Arg  Thr  Val  Val  Thr  Ile  Ala  His  Arg  Val
                              1445                          1450                     1455

His  Thr  Ile  Leu  Ser  Ala  Asp  Leu  Val  Met  Val  Leu  Lys  Arg  Gly  Ala
                         1460                          1465                     1470

Ile  Leu  Glu  Phe  Asp  Lys  Pro  Glu  Thr  Leu  Leu  Ser  Gln  Lys  Asp  Ser
                    1475                          1480                     1485

Val  Phe  Ala  Ser  Phe  Val  Arg  Ala  Asp  Lys
                                   1490                     1495
```

( 2 ) INFORMATION FOR SEQ ID NO:30:

( i ) SEQUENCE CHARACTERISTICS:
        ( A ) LENGTH: 2294 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:30:

```
GATGACCCCT  TCTCAGCTTT  GGATGTCCAT  CTGAGTGACC  ACCTGATGCA  GGCCGGCATC    60

CTTGAGCTGC  TCCGGGATGA  CAAGAGGACA  GTGGTCTTGG  TGACCCACAA  GCTACAGTAT   120

CTGCCTCATG  CAGACTGGAT  CATTGCCATG  AAGGATGGGA  CCATTCAGAG  GGAAGGGACG   180

CTCAAGGACT  TCCAGAGGTC  CGAGTGCCAG  CTCTTTGAGC  ACTGGAAGAC  CCTCATGAAC   240

CGGCAGGACC  AAGAGCTGGA  GAAGGAGACA  GTCATGGAGA  GGAAAGCCTC  AGAGCCATCT   300

CAGGGCCTGC  CCCGTGCCAT  GTCCTCCAGA  GACGGCCTTC  TGCTGGATGA  GGAAGAGGAG   360

GAAGAGGAGG  CAGCCGAAAG  CGAGGAAGAT  GACAACTTAT  CTTCAGTGCT  GCATCAGCGA   420
```

```
GCTAAGATCC CCTGGCGAGC CTGCACTAAG TATCTGTCCT CTGCTGGCAT TCTGCTCCTG      480

TCCCTGCTTG TCTTCTCCCA GCTGCTCAAG CACATGGTCT TGGTGGCCAT TGATTATTGG      540

CTGGCCAAGT GGACGGACAG TGCCCTGGTC CTGAGCCCCG CTGCCAGGAA CTGTTCGCTC      600

AGCCAGGAAT GTGACCTGGA CCAGTCTGTC TATGCCATGG TATTCACCTT GCTCTGCAGC      660

CTGGGTATCG TGCTGTGCCT GGTCACCTCT GTCACTGTGG AGTGGACGGG ACTGAAGGTG      720

GCCAAGAGGC TACACCGCAG CCTGCTCAAC CGCATCATCC TGGCCCCCAT GAGGTTCTTT      780

GAGACCACAC CCCTCGGGAG TATCCTGAAC AGATTTTCAT CCGACTGTAA CACCATTGAC      840

CAGCACATCC CATCCACGCT GGAGTGTCTG AGCCGGTCCA CCCTGCTGTG TGTCTCCGCC      900

CTGACTGTCA TCTCCTATGT CACACCCGTG TTCCTCGTGG CCCTCTTACC CCTAGCTGTT      960

GTGTGCTACT TCATTCAGAA GTACTTCCGA GTGGCATCCA GGGACCTGCA GCAGCTGGAC     1020

GACACGACGC AGCTCCCGCT CGTCTCACAC TTTGCTGAAA CTGTGGAGGG ACTCACCACC     1080

ATCCGTGCCT TCAGGTACGA GGCCCGGTTC CAGCAGAAGC TTCTAGAATA TACCGACTCC     1140

AACAACATCG CCTCCCTCTT CCTCACGGCA GCCAACAGAT GGCTGGAAGT CTGCATGGAG     1200

TACATCGGAG CGTGCGTGGT ACTCATTGCG GCTGCCACCT CCATCTCCAA CTCCCTGCAC     1260

AGGGAACTTT CTGCTGGCCT GGTGGGCCTG GGCCTCACCT ATGCCTTGAT GGTCTCCAAC     1320

TACCTCAACT GGATGGTGAG GAACCTGGCG GACATGGAGA TCCAGCTGGG GGCTGTGAAG     1380

AGGATCCACG CACTCCTGAA AACCGAGGCG GAGAGCTATG AGGGGCTCCT GGCGCCGTCG     1440

TTGATCCCCA AGAACTGGCC AGACCAAGGG AAGATCCAAA TTCAGAACCT GAGCGTGCGC     1500

TATGACAGCT CCCTGAAGCC AGTGCTGAAG CATGTCAACA CCCTCATCTC CCCGGGGCAG     1560

AAGATCGGGA TCTGCGGCCG CACAGGCAGC GGGAAGTCCT CCTTCTCCCT GGCCTTTTTC     1620

CGAATGGTGG ACATGTTTGA AGGACGCATC ATCATTGATG GCATCGACAT CGCCAAGCTG     1680

CCACTTCACA CGCTGCGCTC ACGCCTGTCC ATCATCCTAC AGGACCCCGT CCTCTTCAGC     1740

GGCACGATCA GATTCAACCT GGACCCCGAG AAGAAATGCT CAGACAGCAC ACTGTGGGAG     1800

GCCCTGGAGA TCGCCCAGCT GAAGCTGGTA GTGAAGGCAC TGCCAGGAGG CCTAGATGCC     1860

ATCATCACAG AAGGAGGGGA GAATTTTAGC CAGGGCCAGA GGCAGCTGTT CTGCCTGGCC     1920

CGGGCCTTCG TGAGGAAGAC CAGCATCTTC ATCATGGATG AAGCAACCGC CTCCATCGAC     1980

ATGGCTACGG AGAACATCCT CCAGAAGGTG GTGATGACAG CCTTCGCAGA CCGCACGGTG     2040

GTCACCATCG CGCATCGTGT GCACACCATC CTGAGTGCAG ACCTGGTGAT GGTCCTCAAG     2100

AGGGGTGCTA TCCTGGAGTT TGACAAGCCA GAGACGCTCC TCAGCCAGAA GGACAGCGTG     2160

TTCGCCTCCT TTGTCCGTGC GGACAAGTGA CTTACCGGAG CCAAAGTGCC ACCCCGCGCC     2220

TCGCTTGCTT GCCTAGGATT TCTAACTGCA AATCACTTGT AAATAAATTA ATTCTTTGCT     2280

AAAAAAAAAA AAAA                                                       2294
```

( 2 ) INFORMATION FOR SEQ ID NO:31:

( i ) SEQUENCE CHARACTERISTICS:
        ( A ) LENGTH: 195 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:31:

| | | | | | |
|---|---|---|---|---|---|
| CCATGCCTGG | TGGCTGAGCC | CAGCCCAGCC | CCCAGCACCA | TCGCTGATCC | CAAAGAACTG | 60 |
| GCCAGACCAA | GGGAAGATCC | AGATCCAGAA | CCTGAGCGTG | CGCTACGACA | GCTCCCTGAA | 120 |
| GCCGGTGCTG | AAGCACGTCA | ATGCCCTCAT | CTCCCCTGGA | CAGAAGGTCA | GTGCACGGGC | 180 |
| CCAACCCAAT | GCTGC | | | | | 195 |

( 2 ) INFORMATION FOR SEQ ID NO:32:

( i ) SEQUENCE CHARACTERISTICS:
        ( A ) LENGTH: 2454 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:32:

| | | | | | |
|---|---|---|---|---|---|
| CTGCTCTCTG | CAGCCAGACA | TCGACATCCT | GCCCCATGGA | GACCAGACCC | AGATTGGGGA | 60 |
| ACGGGGCATC | AACCTGTCTG | GTGGTCAACG | CCAGCGAATC | AGTGTGGCCC | GAGCCCTCTA | 120 |
| CCAGCACGCC | AACGTTGTCT | TCTTGGATGA | CCCCTTCTCA | GCTCTGGATA | TCCATCTGAG | 180 |
| TGACCACTTA | ATGCAGGCCG | GCATCCTTGA | GCTGCTCCGG | GACGACAAGA | GGACAGTGGT | 240 |
| CTTAGTGACC | CACAAGCTAC | AGTACCTGCC | CCATGCAGAC | TGGATCATTG | CCATGAAGGA | 300 |
| TGGCACCATC | CAGAGGGAGG | GTACCCTCAA | GGACTTCCAG | AGGTCTGAAT | GCCAGCTCTT | 360 |
| TGAGCACTGG | AAGACCCTCA | TGAACCGACA | GGACCAAGAG | CTGGAGAAGG | AGACTGTCAC | 420 |
| AGAGAGAAAA | GCCACAGAGC | CACCCCAGGG | CCTATCTCGT | GCCATGTCCT | CGAGGGATGG | 480 |
| CCTTCTGCAG | GATGAGGAAG | AGGAGGAAGA | GGAGGCAGCT | GAGAGCGAGG | AGGATGACAA | 540 |
| CCTGTCGTCC | ATGCTGCACC | AGCGTGCTGA | GATCCCATGG | CGAGCCTGCG | CCAAGTACCT | 600 |
| GTCCTCCGCC | GGCATCCTGC | TCCTGTCGTT | GCTGGTCTTC | TCACAGCTGC | TCAAGCACAT | 660 |
| GGTCCTGGTG | CCATCGACT | ACTGGCTGGC | CAAGTGGACC | GACAGCGCCC | TGACCCTGAC | 720 |
| CCCTGCAGCC | AGGAACTGCT | CCCTCAGCCA | GGAGTGCACC | CTCGACCAGA | CTGTCTATGC | 780 |
| CATGGTGTTC | ACGGTGCTCT | GCAGCCTGGG | CATTGTGCTG | TGCCTCGTCA | CGTCTGTCAC | 840 |
| TGTGGAGTGG | ACAGGGCTGA | AGGTGGCCAA | GAGACTGCAC | CGCAGCCTGC | TAAACCGGAT | 900 |
| CATCCTAGCC | CCCATGAGGT | TTTTTGAGAC | CACTCCCCTT | GGGAGCATCC | TGAACAGATT | 960 |
| TTCATCTGAC | TGTAACACCA | TCGACCAGCA | CATCCCATCC | ACGCTGGAGT | GCCTGAGCCG | 1020 |
| CTCCACCCTG | CTCTGTGTCT | CAGCCCTGGC | CGTCATCTCC | TATGTCACAC | CTGTGTTCCT | 1080 |
| CGTGGCCCTC | CTTCCCCTGG | CCATCGTGTG | CTACTTCATC | CAGAAGTACT | TCCGGGTGGC | 1140 |
| GTCCAGGGAC | CTGCAGCAGC | TGGATGACAC | CACCCAGCTT | CCACTTCTCT | CACACTTTGC | 1200 |
| CGAAACCGTA | GAAGGACTCA | CCACCATCCG | GGCCTTCAGG | TATGAGGCCC | GGTTCCAGCA | 1260 |
| GAAGCTTCTC | GAATACACAG | ACTCCAACAA | CATTGCTTCC | CTCTTCCTCA | CAGCTGCCAA | 1320 |
| CAGATGGCTG | GAAGTCCGAA | TGGAGTACAT | CGGTGCATGT | GTGGTGCTCA | TCGCAGCGGT | 1380 |
| GACCTCCATC | TCCAACTCCC | TGCACAGGGA | GCTCTCTGCT | GGCCTGGTGG | GCCTGGGCCT | 1440 |
| TACCTACGCC | CTAATGGTCT | CCAACTACCT | CAACTGGATG | GTGAGGAACC | TGGCAGACAT | 1500 |
| GGAGCTCCAG | CTGGGGGCTG | TGAAGCGCAT | CCATGGGCTC | CTGAAAACCG | AGGCAGAGAG | 1560 |
| CTACGAGGGA | CTCCTGGCAC | CATCGCTGAT | CCCAAAGAAC | TGGCCAGACC | AAGGGAAGAT | 1620 |

| | | | | | | |
|---|---|---|---|---|---|---|
|CCAGATCCAG|AACCTGAGCG|TGCGCTACGA|CAGCTCCCTG|AAGCCGGTGC|TGAAGCACGT|1680|
|CAATGCCCTC|ATCTCCCCTG|GACAGAAGAT|CGGGATCTGC|GGCCGCACCG|GCAGTGGGAA|1740|
|GTCCTCCTTC|TCTCTTGCCT|TCTTCCGCAT|GGTGGACACG|TTCGAAGGGC|ACATCATCAT|1800|
|TGATGGCATT|GACATCGCCA|AACTGCCGCT|GCACACCCTG|CGCTCACGCC|TCTCCATCAT|1860|
|CCTGCAGGAC|CCCGTCCTCT|TCAGCGGCAC|CATCCGATTT|AACCTGGACC|CTGAGAGGAA|1920|
|GTGCTCAGAT|AGCACACTGT|GGGAGGCCCT|GGAAATCGCC|CAGCTGAAGC|TGGTGGTGAA|1980|
|GGCACTGCCA|GGAGGCCTCG|ATGCCATCAT|CACAGAAGGC|GGGGAGAATT|TCAGCCAGGG|2040|
|ACAGAGGCAG|CTGTTCTGCC|TGGCCCGGGC|CTTCGTGAGG|AAGACCAGCA|TCTTCATCAT|2100|
|GGACGAGGCC|ACGGCTTCCA|TTGACATGGC|CACGGAAAAC|ATCCTCCAAA|AGGTGGTGAT|2160|
|GACAGCCTTC|GCAGACCGCA|CTGTGGTCAC|CATCGCGCAT|CGAGTGCACA|CCATCCTGAG|2220|
|TGCAGACCTG|GTGATCGTCC|TGAAGCGGGG|TGCCATCCTT|GAGTTCGATA|AGCCAGAGAA|2280|
|GCTGCTCAGC|CGGAAGGACA|GCGTCTTCGC|CTCCTTCGTC|CGTGCAGACA|AGTGACCTGC|2340|
|CAGAGCCCAA|GTGCCATCCC|ACATTCGGAC|CCTGCCCATA|CCCCTGCCTG|GGTTTTCTAA|2400|
|CTGTAAATCA|CTTGTAAATA|AATAGATTTG|ATTATTTCCT|AAAAAAAAAA|AAAA|2454|

( 2 ) INFORMATION FOR SEQ ID NO:33:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:33:

Pro Leu Ala Phe Ser Gly Thr Glu Xaa His Ser Ala Ala Tyr Arg Val
 1               5                  10                  15
Asp Gln Gly Val
        20

( 2 ) INFORMATION FOR SEQ ID NO:34:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:34:

Pro Leu Ala Phe Xaa Gly Thr Glu Asn His Ser Ala Ala Tyr Arg Val
 1               5                  10                  15
Asp Gln Gly Val Leu Asn Asn Gly
        20

( 2 ) INFORMATION FOR SEQ ID NO:35:

( i ) SEQUENCE CHARACTERISTICS:
        ( A ) LENGTH: 19 amino acids
        ( B ) TYPE: amino acid
        ( D ) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:35:

```
Pro Leu Ala Phe Ser Gly Thr Glu Xaa His Ser Ala Ala Tyr Arg Val
 1               5                  10                  15
Asp Gln Gly
```

(2) INFORMATION FOR SEQ ID NO:36:

(i) SEQUENCE CHARACTERISTICS:
        (A) LENGTH: 20 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:36:

```
Xaa Leu Ala Phe Cys Gly Thr Glu Xaa His Ser Ala Ala Tyr Arg Val
 1               5                  10                  15
Asp Gln Gly Val
            20
```

(2) INFORMATION FOR SEQ ID NO:37:

(i) SEQUENCE CHARACTERISTICS:
        (A) LENGTH: 30 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:37:

```
Pro Leu Ala Phe Cys Gly Thr Glu Xaa His Ser Ala Ala Tyr Arg Val
 1               5                  10                  15
Asp Gln Gly Val Leu Asn Asn Gly Cys Phe Val Asp Ser Tyr
            20              25                  30
```

(2) INFORMATION FOR SEQ ID NO:38:

(i) SEQUENCE CHARACTERISTICS:
        (A) LENGTH: 25 amino acids
        (B) TYPE: amino acid
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:38:

```
Pro Leu Ala Phe Cys Gly Thr Glu Xaa His Ser Ala Ala Tyr Arg Val
 1               5                  10                  15
Asp Gln Gly Val Leu Asn Asn Gly Pro
            20              25
```

( 2 ) INFORMATION FOR SEQ ID NO:39:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:39:

```
Pro Leu Ala Phe Cys Gly Thr Glu Xaa His Ser Ala Ala Tyr Arg Val
 1               5                  10                  15
Asp Gln Gly Val Leu Asn Asn Gly Cys
             20                  25
```

( 2 ) INFORMATION FOR SEQ ID NO:40:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:40:

```
Phe Glu Gly His Ile Arg Phe Asn
 1               5
```

( 2 ) INFORMATION FOR SEQ ID NO:41:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:41:

TTCGAAGGGC ACATCCGATT TAAC    24

( 2 ) INFORMATION FOR SEQ ID NO:42:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:42:

```
Phe Glu Asp Leu Thr
 1               5
```

( 2 ) INFORMATION FOR SEQ ID NO:43:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:43:

TTCGAAGATT TAACC       15

( 2 ) INFORMATION FOR SEQ ID NO:44:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:44:

TTCGAAGATT TAACC       15

( 2 ) INFORMATION FOR SEQ ID NO:45:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:45:

GATC       4

( 2 ) INFORMATION FOR SEQ ID NO:46:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:46:

CCATCCRGTG AGCC       14

( 2 ) INFORMATION FOR SEQ ID NO:47:

( i ) SEQUENCE CHARACTERISTICS:
        ( A ) LENGTH: 14 base pairs

```
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:47:

CAGCCCRGCC CCCA                                                                              1 4

( 2 ) INFORMATION FOR SEQ ID NO:48:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: nucleic acid ( i i i ) HYPOTHETICAL: NO ( i v ) ANTI-SENSE: NO ( x i ) SEQUENCE DESCRIPTION: SEQ ID NO:48:

CCGGCCCCCA GCACCATCGC TGATCCCAAA GAACTGGCCA GACCAA                                            4 6

( 2 ) INFORMATION FOR SEQ ID NO:49:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:49:

Ala  Pro  Ser  Leu  Ile  Pro  Lys  Asn  Trp  Pro  Asp  Gln
  1              5                        1 0
```

What is claimed is:

1. A method of screening for persistent hyperinsulinemic hypoglycemia of infancy comprising obtaining a sample comprising patient nucleic acids from a patient tissue sample;

amplifying nucleic acids encoding sulfonylurea receptor or a portion thereof from said patient nucleic acids to produce a test fragment;

obtaining a sample comprising control nucleic acids from a control tissue sample;

amplifying control nucleic acids encoding wild type sulfonylurea receptor to produce a control fragment;

comparing the test fragment with the control fragment to detect the presence of a sequence difference in the test fragment, wherein a difference in said test fragment may indicate persistent hyperinsulinemic hypoglycemia of infancy.

2. The method of claim 1 wherein a sequence difference results in a restriction digest pattern alteration.

3. The method of claim 1 wherein a sequence difference is a nucleic acid transition.

4. The method of claim 3 wherein said nucleic acid transition is a G to A transition at nucleic acid position 750 of SEQ ID NO: 26.

5. The method of claim 3 wherein a nucleic acid transition results at position 27 of SEQ ID NO: 31.

6. The method of claim 1 wherein amplification is performed using a primer pair, wherein on primer has the sequence of SEQ ID NO: 18 and said test fragment is digested with MspI to produce digested test fragments of about 304 base pairs and about 123 base pairs.

7. The method of claim 1 wherein amplification is performed using a pair wherein one primer has the sequence of SEQ ID NO: 18 and said test fragment is digested with NciI to produce a digested test fragment of about 146 base pairs.

8. The method of claim 1 wherein said amplification step comprises performing the polymerase chain reaction.

9. The method of claim 8 wherein the polymerase chain reaction comprises using a pair of primers, wherein one primer within said pair is selected from the group consisting of SEQ ID NOS: 16–24.

10. The method of claim 8 wherein said polymerase chain reaction comprises the use of two primers, a first primer selected from the group consisting of SEQ ID NOS: 13, 14, 17, and 19, and a second primer selected from the group consisting of SEQ ID NOS: 12, 15, 16, 18, and 20.

11. The method of claim 1 wherein said tissue sample is selected from the group consisting of pancreatic tissue, blood, serum, saliva, sputum, mucus, bone marrow, urine, lymph, and a tear.

12. A method of screening for persistent hyperinsulinemic hypoglycemia of infancy comprising
obtaining a sample comprising patient genomic DNA from a patient tissue sample;
amplifying DNA encoding sulfonylurea receptor or a portion thereof from said patient genomic DNA to produce a test fragment;
obtaining a sample comprising control nucleic acids from a control tissue sample;
amplifying control DNA encoding wild type sulfonylurea receptor to produce a control fragment;
digesting said test fragment and said control fragment with MspI to produce digested test fragments and digested control fragments;
comparing the digested test fragments with the digested control fragments to detect digested test fragments of about 304 base pairs and about 123 base pairs compared to said digested control fragments, wherein the presence of digested test fragments of about 304 base pairs and about 123 base pairs indicates persistent hyperinsulinemic hypoglycemia of infancy.

13. A method of detecting persistent hyperinsulinemic hypoglycemia of infancy comprising
obtaining a sample comprising patient genomic DNA from a patient tissue sample;
amplifying DNA encoding sulfonylurea receptor or a portion thereof from said patient genomic DNA to produce a test fragment;
obtaining a sample comprising control nucleic acids from a control tissue sample;
amplifying control DNA encoding wild type sulfonylurea receptor to produce a control fragment;
comparing the test fragment with the control fragment to detect a test fragment having G to A transition corresponding to nucleic acid position 750 of SEQ ID NO: 1, wherein the presence of said G to A transition in the test fragment indicates hyperinsulinemic hypoglycemia of infancy.

14. A method of screening for persistent hyperinsulinemic hypoglycemia of infancy comprising
obtaining a sample comprising patient genomic DNA from a patient tissue sample;
amplifying DNA encoding sulfonylurea receptor or a portion thereof from said patient genomic DNA to produce a test fragment;
obtaining a sample comprising control nucleic acids from a control tissue sample;
amplifying control DNA encoding wild type sulfonylurea receptor to produce a control fragment;
digesting said test fragment and said control fragment with NciI to produce a digested test fragment and a digested control fragment;
comparing the digested test fragment with the digested control fragment to detect a digested test fragment of about 146 base pairs compared to the digested control fragment, wherein the presence of digested test fragment of about 146 base pairs indicates persistent hyperinsulinemic hypoglycemia of infancy.

15. A method of claim 13 or 14, wherein said amplification step comprises performing the polymerase chain reaction.

16. A diagnostic kit for detecting persistent hyperinsulinemic hypoglycemia of infancy comprising in one or more containers a pair of primers, wherein one primer within said pair is complementary to a region of nucleic acids encoding the sulfonylurea receptor, wherein said one primer specifically hybridizes to said nucleic acids, wherein one of said pair of primers is selected from the group consisting of SEQ ID NOS: 12–20, a probe which specifically hybridizes to the amplified product, and a means for visualizing amplified DNA, and optionally including one or more size markers, and positive and negative controls.

17. The diagnostic kit of claim 16 wherein said means for visualizing amplified DNA is selected from the group consisting of a DNA binding fluorescent stain, $^{32}$P, and biotin.

18. An isolated nucleic acid molecule selected from the group consisting of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

* * * * *